US012569517B2

(12) United States Patent (10) Patent No.: US 12,569,517 B2
Pettine et al. (45) Date of Patent: Mar. 10, 2026

(54) METHOD FOR TREATING OSTEOARTHRITIS WITH MESENCHYMAL STEM CELL EXOSOMES

(71) Applicant: Direct Biologics, LLC, Austin, TX (US)

(72) Inventors: Kenneth Allen Pettine, Fort Collins, CO (US); Timothy Alexander Moseley, Carlsbad, CA (US)

(73) Assignee: Direct Biologics, LLC, Austin, TX (US)

( * ) Notice: Subject to any disclaimer, the term of this patent is extended or adjusted under 35 U.S.C. 154(b) by 1118 days.

(21) Appl. No.: 17/429,553

(22) PCT Filed: Feb. 7, 2020

(86) PCT No.: PCT/US2020/017341
§ 371 (c)(1),
(2) Date: Aug. 9, 2021

(87) PCT Pub. No.: WO2020/163803
PCT Pub. Date: Aug. 13, 2020

(65) Prior Publication Data
US 2022/0125848 A1 Apr. 28, 2022

Related U.S. Application Data

(60) Provisional application No. 62/908,853, filed on Oct. 1, 2019, provisional application No. 62/802,310, filed on Feb. 7, 2019.

(51) Int. Cl.
*A61K 35/12* (2015.01)
*A61K 9/00* (2006.01)
(Continued)

(52) U.S. Cl.
CPC ............ *A61K 35/26* (2013.01); *A61K 9/0014* (2013.01); *A61K 9/0019* (2013.01); *A61K 35/28* (2013.01); *A61P 19/02* (2018.01); *A61P 29/00* (2018.01)

(58) Field of Classification Search
CPC .............................................. A61K 2035/122
See application file for complete search history.

(56) References Cited

U.S. PATENT DOCUMENTS 3,610,795 A 10/1971 Antoine et al.
4,897,355 A 1/1990 Eppstein et al.
(Continued)

FOREIGN PATENT DOCUMENTS

AU 2004203482 A1 8/2004
CA 2880404 A1 2/2014
(Continued)

OTHER PUBLICATIONS

Pourakbari et al., "The potential of exosomes in the therapy of the cartilage and bone complications; emphasis on osteoarthritis," Life Sciences 236(116861):1-8, Sep. 2019.*
(Continued)

*Primary Examiner* — Rosanne Kosson
(74) *Attorney, Agent, or Firm* — Wilson Sonsini Goodrich & Rosati

(57) ABSTRACT

Disclosed herein are methods for treating osteoarthritis may be a one-step arthroscopic procedure and may include detaching synovial mesenchymal stem cells (MSCs) from the synovium using a brush device; covering articular cartilage in an affected joint with a scaffold; and placing concentrated MSC exosomes into the affected joint to stimulate differentiation of synovial MSCs into articular cartilage cells.

20 Claims, 5 Drawing Sheets

(51) Int. Cl.

| | | |
|---|---|---|
| *A61K 35/26* | (2015.01) | |
| *A61K 35/28* | (2015.01) | |
| *A61P 19/02* | (2006.01) | |
| *A61P 29/00* | (2006.01) | |

(56) References Cited

U.S. PATENT DOCUMENTS

| | | | |
|---|---|---|---|
| 5,135,917 | A | 8/1992 | Burch et al. |
| 5,712,163 | A | 1/1998 | Parenteau et al. |
| 6,410,588 | B1 | 6/2002 | Feldmann et al. |
| 7,029,666 | B2 | 4/2006 | Bruder et al. |
| 8,021,882 | B2 | 9/2011 | Johnstone et al. |
| 8,057,789 | B2 | 11/2011 | Hariri |
| 8,372,797 | B2 | 2/2013 | Ichim |
| 8,703,710 | B2 | 4/2014 | Dzau et al. |
| 8,778,416 | B2 | 7/2014 | Cohen |
| 9,408,874 | B2 | 8/2016 | Pettine |
| 9,744,130 | B2 | 8/2017 | Lipp et al. |
| 9,822,359 | B1 | 11/2017 | Cooper et al. |
| 9,856,455 | B2 | 1/2018 | March et al. |
| 9,980,984 | B2 | 5/2018 | Pettine |
| 10,456,425 | B2 | 10/2019 | Herrera Sanchez et al. |
| 10,744,160 | B2 | 8/2020 | Sokolov et al. |
| 10,881,693 | B2 | 1/2021 | Alford |
| 11,376,283 | B2 | 7/2022 | Sokolov et al. |
| 11,529,306 | B2 | 12/2022 | Yi et al. |
| 12,233,092 | B2 | 2/2025 | Aricha et al. |
| 2004/0248970 | A1 | 12/2004 | Webster et al. |
| 2007/0254827 | A1 | 11/2007 | Sutton et al. |
| 2008/0241112 | A1 | 10/2008 | Westenfelder |
| 2009/0177487 | A1 | 7/2009 | Eerkes |
| 2010/0178274 | A1 | 7/2010 | Sekiya et al. |
| 2011/0003008 | A1 | 1/2011 | Lim |
| 2011/0014251 | A1 | 1/2011 | Ray |
| 2012/0064049 | A1 | 3/2012 | Hunziker |
| 2013/0115198 | A1 | 5/2013 | Hoffmann et al. |
| 2013/0195899 | A1 | 8/2013 | Ichim et al. |
| 2013/0210725 | A1 | 8/2013 | Naughton et al. |
| 2013/0236427 | A1 | 9/2013 | Pernock |
| 2014/0004601 | A1 | 1/2014 | Lim |
| 2014/0065240 | A1 | 3/2014 | Mitsialis et al. |
| 2014/0220053 | A1 | 8/2014 | Muraca et al. |
| 2015/0086513 | A1 | 3/2015 | Savkovic et al. |
| 2015/0125950 | A1 | 5/2015 | Lim et al. |
| 2016/0113967 | A1 | 4/2016 | Hedrick et al. |
| 2016/0263160 | A1 | 9/2016 | Nolta et al. |
| 2016/0281045 | A1 | 9/2016 | McCall et al. |
| 2017/0051359 | A1 | 2/2017 | Pegtel et al. |
| 2017/0055561 | A1 | 3/2017 | Naughton et al. |
| 2017/0107488 | A1 | 4/2017 | Petcavich |
| 2017/0166864 | A1 | 6/2017 | Kihm et al. |
| 2017/0189449 | A1 | 7/2017 | Lim |
| 2017/0304368 | A1 | 10/2017 | Marban et al. |
| 2018/0100149 | A1 | 4/2018 | Marbán et al. |
| 2018/0214489 | A1 | 8/2018 | Riordan |
| 2018/0242590 | A1 | 8/2018 | Friedman |
| 2018/0264043 | A1 | 9/2018 | Pettine et al. |
| 2018/0282762 | A1 | 10/2018 | Gori |
| 2018/0318356 | A1 | 11/2018 | Pettine et al. |
| 2018/0338866 | A1 | 11/2018 | Kharazmi |
| 2019/0000886 | A1 | 1/2019 | Ross |
| 2019/0015331 | A1 | 1/2019 | Elliman et al. |
| 2019/0046574 | A1 | 2/2019 | Wang et al. |
| 2019/0046576 | A1 | 2/2019 | Gangaraju et al. |
| 2019/0133922 | A1 | 5/2019 | Kang et al. |
| 2019/0195863 | A1 | 6/2019 | Brivanlou et al. |
| 2019/0209665 | A1 | 7/2019 | Pluchino et al. |
| 2019/0269739 | A1 | 9/2019 | Brodie et al. |
| 2019/0328792 | A1 | 10/2019 | Traweger et al. |
| 2019/0330594 | A1 | 10/2019 | You et al. |
| 2020/0030253 | A1 | 1/2020 | Kharazmi |
| 2020/0316226 | A1 | 10/2020 | Marban et al. |
| 2020/0325452 | A1 | 10/2020 | Alford |
| 2021/0000882 | A1 | 1/2021 | Coronado |
| 2021/0030807 | A1 | 2/2021 | Aricha et al. |
| 2021/0038652 | A1 | 2/2021 | Naughton et al. |
| 2021/0128627 | A1 | 5/2021 | Aricha et al. |
| 2021/0169939 | A1 | 6/2021 | Ilagan et al. |
| 2021/0196759 | A1 | 7/2021 | Moseley et al. |
| 2021/0228643 | A1 | 7/2021 | Bobis-Wozowicz et al. |
| 2021/0254056 | A1 | 8/2021 | Liu et al. |
| 2021/0267892 | A1 | 9/2021 | Machluf et al. |
| 2021/0299036 | A1 | 9/2021 | Naughton |
| 2021/0348114 | A1 | 11/2021 | Hudson et al. |
| 2021/0363525 | A1 | 11/2021 | Saetrom et al. |
| 2021/0369617 | A1 | 12/2021 | Alford |
| 2022/0000932 | A1 | 1/2022 | Zhang et al. |
| 2022/0079987 | A1 | 3/2022 | Pettine |
| 2022/0079990 | A1 | 3/2022 | Moseley et al. |
| 2022/0096560 | A1 | 3/2022 | Mitsialis et al. |
| 2022/0110970 | A1 | 4/2022 | Jhan et al. |
| 2022/0136011 | A1 | 5/2022 | Kalluri |
| 2022/0136053 | A1 | 5/2022 | Pettine et al. |
| 2022/0151934 | A1 | 5/2022 | Ridall et al. |
| 2022/0152151 | A1 | 5/2022 | Pettine |
| 2022/0175843 | A1 | 6/2022 | Westenfelder et al. |
| 2022/0195384 | A1 | 6/2022 | Kim et al. |
| 2022/0195390 | A1 | 6/2022 | Uzan et al. |
| 2022/0202871 | A1 | 6/2022 | Pettine |
| 2022/0218755 | A1 | 7/2022 | Ilagan et al. |
| 2022/0249699 | A1 | 8/2022 | Guild et al. |
| 2022/0257661 | A1 | 8/2022 | Pettine et al. |
| 2022/0264872 | A1 | 8/2022 | March et al. |
| 2022/0273725 | A1 | 9/2022 | Ochiya |
| 2022/0387518 | A1 | 12/2022 | Mishra et al. |
| 2023/0000954 | A1 | 1/2023 | Alford et al. |
| 2023/0002476 | A1 | 1/2023 | Alford et al. |
| 2023/0013636 | A1 | 1/2023 | Kalluri |
| 2023/0105667 | A1 | 4/2023 | Brodie |
| 2023/0142496 | A1 | 5/2023 | Cheng |
| 2023/0143893 | A1 | 5/2023 | Bird et al. |
| 2023/0159932 | A1 | 5/2023 | Pettine et al. |
| 2023/0172990 | A1 | 6/2023 | Ohneda et al. |
| 2023/0181649 | A1 | 6/2023 | Hariri et al. |
| 2023/0190818 | A1 | 6/2023 | Jurga |
| 2023/0226267 | A1 | 7/2023 | Madelska |
| 2023/0248773 | A1 | 8/2023 | Jurga |
| 2023/0257712 | A1 | 8/2023 | Jurga |
| 2023/0310507 | A1 | 10/2023 | Lebovits et al. |
| 2023/0313191 | A1 | 10/2023 | Hicok et al. |

FOREIGN PATENT DOCUMENTS

| | | |
|---|---|---|
| CN | 104622904 A | 5/2015 |
| CN | 108042572 A | 5/2018 |
| CN | 108498452 A | 9/2018 |
| CN | 111150743 A | 5/2020 |
| CN | 109718392 B | 11/2021 |
| EP | 2582791 A2 | 4/2013 |
| EP | 2687219 A1 | 1/2014 |
| EP | 2296672 B1 | 9/2015 |
| EP | 2683389 B1 | 5/2017 |
| EP | 2877187 B1 | 6/2019 |
| EP | 3492585 A1 | 6/2019 |
| EP | 3668319 A1 | 6/2020 |
| EP | 3672606 A1 | 7/2020 |
| EP | 3723773 A1 | 10/2020 |
| EP | 3402489 B1 | 6/2021 |
| EP | 3920889 A1 | 12/2021 |
| EP | 3952892 A1 | 2/2022 |
| EP | 4003305 A1 | 6/2022 |
| EP | 4069826 A1 | 10/2022 |
| EP | 4132546 A2 | 2/2023 |
| EP | 4181935 A1 | 5/2023 |
| JP | 2008544957 A | 12/2008 |
| JP | 2011513217 A | 4/2011 |
| JP | 2014500249 A | 1/2014 |
| JP | 2016065106 A | 4/2016 |
| JP | 2017180553 A | 10/2017 |
| JP | 2018538132 A | 12/2018 |
| JP | WO2019235362 A1 | 7/2021 |
| JP | 2022516607 A | 3/2022 |
| KR | 20180023865 A | 3/2018 |
| KR | 20180127280 A | 11/2018 |

(56) References Cited

FOREIGN PATENT DOCUMENTS

| | | |
|---|---|---|
| WO | WO-03051331 A1 | 6/2003 |
| WO | WO-2006036213 A2 | 4/2006 |
| WO | WO-2006071011 A1 | 7/2006 |
| WO | WO-2009105044 A1 | 8/2009 |
| WO | WO-2009150199 A1 | 12/2009 |
| WO | WO-2011082950 A1 * | 7/2011 ............ A61P 37/06 |
| WO | WO-2011160055 A2 | 12/2011 |
| WO | WO-2012061537 A2 | 5/2012 |
| WO | WO-2012125471 A1 | 9/2012 |
| WO | WO-2012142569 A2 | 10/2012 |
| WO | WO-2012174282 A2 | 12/2012 |
| WO | WO-2013006327 A1 | 1/2013 |
| WO | WO-2013090523 A2 | 6/2013 |
| WO | WO-2013150303 A1 | 10/2013 |
| WO | WO-2013159091 A2 | 10/2013 |
| WO | WO-2014005183 A1 | 1/2014 |
| WO | WO-2015031110 A2 | 3/2015 |
| WO | WO-2015048842 A1 | 4/2015 |
| WO | WO-2016082882 A1 | 6/2016 |
| WO | WO-2016149358 A1 | 9/2016 |
| WO | WO-2016156865 A1 | 10/2016 |
| WO | WO-2017001649 A1 | 1/2017 |
| WO | WO-2017023689 A1 | 2/2017 |
| WO | WO-2017076924 A1 | 5/2017 |
| WO | WO-2017117585 A1 | 7/2017 |
| WO | WO-2017122095 A1 | 7/2017 |
| WO | WO-2017123022 A1 | 7/2017 |
| WO | WO-2017139795 A1 | 8/2017 |
| WO | WO-2017196798 A1 | 11/2017 |
| WO | WO-2017218846 A1 | 12/2017 |
| WO | WO-2018038575 A1 | 3/2018 |
| WO | WO-2018078524 A1 | 5/2018 |
| WO | WO-2018083700 A1 | 5/2018 |
| WO | WO-2018102696 A1 | 6/2018 |
| WO | WO-2018130554 A1 | 7/2018 |
| WO | WO-2018131003 A1 | 7/2018 |
| WO | WO-2018131900 A2 | 7/2018 |
| WO | WO-2018144637 A1 | 8/2018 |
| WO | WO-2018150440 A1 | 8/2018 |
| WO | WO-2018162696 A1 | 9/2018 |
| WO | WO-2018208670 A1 | 11/2018 |
| WO | WO-2018211510 A1 | 11/2018 |
| WO | WO-2018226758 A2 | 12/2018 |
| WO | WO-2019035880 A1 | 2/2019 |
| WO | WO-2019040896 A1 | 2/2019 |
| WO | WO-2019099955 A1 | 5/2019 |
| WO | WO-2019118817 A1 | 6/2019 |
| WO | WO-2019143847 A1 | 7/2019 |
| WO | WO-2019152522 A1 | 8/2019 |
| WO | WO-2019161590 A1 | 8/2019 |
| WO | WO-2019217091 A1 | 11/2019 |
| WO | WO-2019222170 A1 | 11/2019 |
| WO | WO-2019231562 A1 | 12/2019 |
| WO | WO-2019235362 A1 | 12/2019 |
| WO | WO-2020021312 A1 | 1/2020 |
| WO | WO-2020051362 A1 | 3/2020 |
| WO | WO-2020061408 A1 | 3/2020 |
| WO | WO-2020081859 A1 | 4/2020 |
| WO | WO-2020139975 A1 | 7/2020 |
| WO | WO-2020142769 A1 | 7/2020 |
| WO | WO-2020160342 A1 | 8/2020 |
| WO | WO-2020163705 A1 | 8/2020 |
| WO | WO-2020163803 A1 | 8/2020 |
| WO | WO-2020172270 A1 | 8/2020 |
| WO | WO-2020182938 A1 | 9/2020 |
| WO | WO-2020210248 A1 | 10/2020 |
| WO | WO-2020223349 A1 | 11/2020 |
| WO | WO-2020230954 A1 | 11/2020 |
| WO | WO-2020251181 A1 | 12/2020 |
| WO | WO-2020257720 A1 | 12/2020 |
| WO | WO-2021009660 A1 | 1/2021 |
| WO | WO-2021011935 A1 | 1/2021 |
| WO | WO-2021016368 A1 | 1/2021 |
| WO | WO-2021016727 A1 | 2/2021 |
| WO | WO-2021113299 A1 | 6/2021 |
| WO | WO-2021113761 A1 | 6/2021 |
| WO | WO-2021147923 A1 | 7/2021 |
| WO | WO-2021177473 A1 | 9/2021 |
| WO | WO-2021181399 A1 | 9/2021 |
| WO | WO-2021195154 A1 | 9/2021 |
| WO | WO-2021207282 A2 | 10/2021 |
| WO | WO-2021216903 A1 | 10/2021 |
| WO | WO-2021221471 A1 | 11/2021 |
| WO | WO-2021226108 A1 | 11/2021 |
| WO | WO-2021262879 A1 | 12/2021 |
| WO | WO-2022008654 A1 | 1/2022 |
| WO | WO-2022008657 A1 | 1/2022 |
| WO | WO-2022018729 A1 | 1/2022 |
| WO | WO-2022050373 A1 | 3/2022 |
| WO | WO-2022076419 A1 | 4/2022 |
| WO | WO-2022096708 A1 | 5/2022 |
| WO | WO-2022150696 A1 | 7/2022 |
| WO | WO-2022150839 A1 | 7/2022 |
| WO | WO-2022174079 A1 | 8/2022 |
| WO | WO-2022190091 A1 | 9/2022 |
| WO | WO-2022251167 A2 | 12/2022 |
| WO | WO-2022261636 A1 | 12/2022 |
| WO | WO-2022265864 A2 | 12/2022 |
| WO | WO-2022266399 A1 | 12/2022 |
| WO | WO-2023004087 A2 | 1/2023 |
| WO | WO-2023275164 A1 | 1/2023 |
| WO | WO-2023278883 A1 | 1/2023 |
| WO | WO-2023281524 A1 | 1/2023 |
| WO | WO-2023282424 A1 | 1/2023 |
| WO | WO-2023283578 A1 | 1/2023 |
| WO | WO-2023021525 A1 | 2/2023 |
| WO | WO-2023024637 A1 | 3/2023 |
| WO | WO-2023033500 A1 | 3/2023 |
| WO | WO-2023064555 A1 | 4/2023 |
| WO | WO-2023075557 A1 | 5/2023 |
| WO | WO-2023082012 A1 | 5/2023 |
| WO | WO-2023091904 A1 | 5/2023 |
| WO | WO-2023123216 A1 | 7/2023 |
| WO | WO-2023127645 A1 | 7/2023 |
| WO | WO-2023192916 A2 | 10/2023 |
| WO | WO-2023200882 A1 | 10/2023 |
| WO | WO-2024192119 A1 | 9/2024 |
| WO | WO-2024254459 A2 | 12/2024 |
| WO | WO-2024254540 A2 | 12/2024 |
| WO | WO-2025101653 A1 | 5/2025 |
| WO | WO-2025101658 A1 | 5/2025 |
| WO | WO-2025101659 A1 | 5/2025 |
| WO | WO-2025101663 A1 | 5/2025 |

OTHER PUBLICATIONS

Hamilton et al., "Targeting VEGF and its receptors for the treatment of osteoarthritis and associated pain," Journal of Bone and Mineral Research 31(5):911-924, 2016.*

Extended European Search Report for European Application No. 20752269.9 dated Oct. 7, 2022, 10 pages.

Stella Cosenza et al., "Mesenchymal stem cells derived exosomes and microparticles protect cartilage and bone from degradation in osteoarthritis", Scientific Reports, vol. 7, No. I, Dec. 1, 2017.

Yu Zhu et al., "Comparison of exosomes secreted by induced pluripotent stem cell-derived mesenchymal stem cells and synovial membrane-derived mesenchymal stem cells for the treatment of osteoarthritis", Stem Cell Research & Therapy, vol. 8, No. 1, Mar. 9, 2017.

Yafei Wang et al., "Exosomes from embryonic mesenchymal stem cells alleviate osteoarthritis through balancing synthesis and degradation of cartilage extracellular matrix", Stem Cell Research & Therapy, vol. 8, No. 1, Dec. 1, 2017.

Yeo Jin Choi et al., "Exosomes secreted by human adipose-derived stem cells regulate the expression of collagen synthesis-related genes in human dermal fibroblasts", (2017) Abstract Book: ISEV2017, Journal of Extracellular Vesicles, 6:supl, 1310414; PF11.07, May 15, 2017 , pp. 141-141.

S. Zhang et al., "Exosomes derived from human embryonic mesenchymal stem cells promote osteochondral regeneration", Osteoarthritis and Cartilage, Elsevier, Amsterdam, NL, vol. 24, No. 12, Jul. 5, 2016, pp. 2135-2140.

(56) References Cited

OTHER PUBLICATIONS

Maxwell Dordevic et al., "Intra-Articular Injection of an Extracellular Vesicle Isolate Product to Treat Hip Labral Tears", Journal of Regenerative Biology and Medicine, vol. 11, Oct. 1, 2019, pp. 1-6.

International Search Report and Written Opinion issued in PCT/US2020/017341, dated Apr. 28, 2020, 9 pages.

Kandola "How does rheumatoid arthritis affect the wrists?"; Publication [online]. Sep. 13, 2018 [retrieved Apr. 1, 2020]. Retrieved from the Internet: <URL:https://www.medicalnewstoday.com/articles/323056>.

Aatonen, Maria et al. Isolation and Characterization of Platelet-derived Extracellular Vesicles. Journal of Extracellular Vesicles 3:1-15 (2014).

Alam et al., An osteopontin-derived peptide inhibits human hair growth at least in part by decreasing fibroblast growth factor-7 production in outer root sheath keratinocytes. Br J Dermatol 182(6):1404-1414 (2020).

Aversa et al., Platelet-derived growth factor (PDGF) and PDGF receptors in rat corpus cavernosum: changes in expression after transient in vivo hypoxia. J Endocrinol. 170(2):395-402 (2001).

Bagshawe, K. D., et al. A cytotoxic agent can be generated selectively at cancer sites. British Journal of Cancer 58(6):700-703 (1988).

Bagshawe, K. D. Towards generating cytotoxic agents at cancer sites. The First Bagshawe Lecture. Br. J. Cancer 60:275-281 (1989).

Batch et al., Identification and localization of insulin-like growth factor-binding protein (IGFBP) messenger RNAs in human hair follicle dermal papilla. J Invest Dermatol. 106(3):471-475 (1996).

Battelli et al., T lymphocyte killing by a xanthine-oxidase-containing immunotoxin. Cancer Immunology, Immunotherapy 35(6):421-425 (1992).

Bender et al.: Intra-Articular Injection of an Extracellular Vesicle Isolate to Treat Shoulder Osteoarthritis in an Athlete. J Regen Biol Med. 2(1):1-6 (2020).

Bender et al.: Treatment of Elbow Arthritis with a Bone Marrow derived Mesenchymal Stem Cell Extracellular Vesicle Isolate Product. J Orthop Study Sports Med. 1(1):1-6 (2021).

Bertolini et al., Abnormal interactions between perifollicular mast cells and CD8+ T-cells may contribute to the pathogenesis of alopecia areata. PLoS One. 9:e94260 (2014).

Bligh et al.: Safety and Efficacy of Bone Marrow Mesenchymal Stem Cell Extracellular Vesicles in Long COVID patients: A Case Series. J Stem Cell Res Dev Ther. 10(112):1-8 (2024).

Bligh: Treatment of Idiopathic Pulmonary Fibrosis With an Extracellular Vesicle Isolate Product. International Journal of Science and Research Archive. 02(02):231-236 (2021).

Blood And Marrow Stem Cell Transplantation. Leukemia & Lymphoma Society Retrieved from Internet URL: http://www.lls.org/resource-center/download-or-order-free-publications. Accessed on Jul. 8, 2016.

Boraschi CA, IL-18 in autoimmunity: review. Eur Cytokine Netw. 17:224-252 (2006).

Botchkarev et al., Edar signaling in the control of hair follicle development. J Invest Dermatol Symp Proc. 10(3):247-251 (2005).

Brigham et al. Expression of a prokaryotic gene in cultured lung endothelial cells after lipofection with a plasmid vector. Am. J. Resp. Cell. Mol. Biol. 1:95-100 (1989).

Brown et al., Molecular and cellular mechanisms of receptor-mediated endocytosis. DNA and Cell Biology 10(6):399-409 (1991).

Burnett et al., GGF2 is neuroprotective in a rat model of cavernous nerve injury-induced erectile dysfunction. J Sex Med. 12(4):897-905 (2015).

Cabana: An Update on Exosomes. Aesthetic Authority. Technology Pipeline: Aestic Authority 2(1):22 (2020) https://www.dermatologytimes.com/view/an-update-on-exosomes.

Cai et al., Suppression of hepatocyte growth factor production impairs the ability of adipose-derived stem cells to promote ischemic tissue revascularization. Stem Cells 25(12):3234-3243 (2007).

Carneiro et al., Emerging role for TNF-a in erectile dysfunction. J Sex Med. 7(12):3823-3834 (2010).

Celik et al., Genetic analysis of interleukin 18 gene polymorphisms in alopecia areata. J Clin Lab Anal. 32(5):e22386 (2018).

Centeno: Exosomes, Mary Kaye, and Pink Caddys (2019) https://regenexx.com/blog/direct-biologics-exosomes/.

Chen et al., Regenerative hair waves in aging mice and extra-follicular modulators follistatin, dkkl, and sfrp4. J Invest Dermatol. 134(8):2086-2096 (2014).

Chew et al., Mesenchymal stem cell exosomes enhance periodontal ligament cell functions and promote periodontal regeneration. Acta Biomater 15:89:252-264 (2019).

Clinical Trial No. NCT04493242. Extracellular Vesicle Infusion Treatment for COVID-19 Associated ARDS. https://clinicaltrials.gov/study/NCT04493242 (Jul. 29, 2020).

Clinical Trial No. NCT04657458. Expanded Access for Use of bmMSC-Derived Extracellular Vesicles in Patients With COVID-19 Associated ARDS. https://clinicaltrials.gov/study/NCT04657458 (Dec. 7, 2020).

Clinical Trial No. NCT05116761. ExoFlo™ Infusion for Post-Acute COVID-19 and Chronic Post-COVID-19 Syndrome. https://clinicaltrials.gov/study/NCT05116761 (Nov. 9, 2021).

Clinical Trial No. NCT05125562. Extracellular Vesicles Infusion Treatment for Mild-to-Moderate COVID-19. https://clinicaltrials.gov/study/NCT05125562 (Nov. 16, 2021).

Clinical Trial No. NCT05127122. Bone Marrow Mesenchymal Stem Cell Derived Extracellular Vesicles Infusion Treatment for ARDS. https://clinicaltrials.gov/study/NCT05127122 (Nov. 9, 2021).

Clinical Trial No. NCT05130983. Study of ExoFlo for the Treatment of Medically Refractory Crohn's Disease. https://clinicaltrials.gov/study/NCT05130983 (Nov. 16, 2021).

Clinical Trial No. NCT05176366. Study of ExoFlo for the Treatment of Medically Refractory Ulcerative Colitis. https://clinicaltrials.gov/study/NCT05176366 (Dec. 14, 2021).

Clinical Trial No. NCT05215288. Expanded Access for Use of ExoFlo in Abdominal Solid Organ Transplant Patients https://clinicaltrials.gov/study/NCT05215288 (Jan. 18, 2022).

Clinical Trial No. NCT05354141. Extracellular Vesicle Treatment for Acute Respiratory Distress Syndrome (ARDS) (Extinguish ARDS). https://clinicaltrials.gov/study/NCT05354141 (Apr. 22, 2022).

Clinical Trial No. NCT05836883. Study of ExoFlo for the Treatment of Perianal Fistulas. https://clinicaltrials.gov/study/NCT05836883 (Apr. 19, 2023).

Conese et al.: Paracrine Effects and Heterogeneity of Marrow-Derived Stem/Progenitor Cells: Relevance for the Treatment of Respiratory Diseases. Cells Tissues Organs. 197:445-473 (2013).

Co-pending Appl. Serial No. PCT/US2019/026595 Application As Filed Apr. 9, 2019.

Co-pending Appl. Serial No. PCT/US2019/068615 Application As Filed Dec. 26, 2019.

Co-pending Appl. Serial No. PCT/US2020/012359 Application As Filed Jan. 6, 2020.

Co-pending Appl. Serial No. PCT/US2020/015982 Application As Filed Jan. 30, 2020.

Co-pending Appl. Serial No. PCT/US2020/017341 Application As Filed Feb. 7, 2020.

Co-pending Appl. Serial No. PCT/US2020/018821 Application As Filed Feb. 19, 2020.

Co-pending Appl. Serial No. PCT/US2020/030476 Application As Filed Apr. 29, 2020.

Co-pending Appl. Serial No. PCT/US2020/042762 Application As Filed Jul. 20, 2020.

Co-pending Appl. Serial No. PCT/US2021/028686 Application As Filed Apr. 22, 2021.

Co-pending Appl. Serial No. PCT/US2023/065115 Application As Filed Mar. 29, 2023.

Co-pending Appl. Serial No. PCT/US2024/019725 Application As Filed Mar. 13, 2024.

Co-pending Appl. Serial No. PCT/US2024/026444 Application As Filed Apr. 26, 2024.

Co-pending Appl. Serial No. PCT/US2024/033022 Application As Filed Jun. 7, 2024.

Co-pending Appl. Serial No. PCT/US2024/033123 Application As Filed Jun. 7, 2024.

Co-pending U.S. Appl. No. 17/059,874 Claims as of May 7, 2024.

(56)                    References Cited

OTHER PUBLICATIONS

Co-pending U.S. Appl. No. 17/418,342 Claims as of May 21, 2024.
Co-pending U.S. Appl. No. 17/420,500 Claims as of Jun. 13, 2024.
Co-pending U.S. Appl. No. 17/427,192 Claims as of Jun. 13, 2024.
Co-pending U.S. Appl. No. 17/432,138 Claims as of Aug. 19, 2021.
Co-pending U.S. Appl. No. 17/606,514 Claims as of Oct. 26, 2021.
Co-pending U.S. Appl. No. 17/628,011 Claims as of Jan. 18, 2022.
Co-pending U.S. Appl. No. 17/920,997 Claims as of Oct. 24, 2022.
Co-pending U.S. Appl. No. 18/192,593 Claims as of Jun. 7, 2023.
Crose et al.: Bone marrow mesenchymal stem cell-derived extracellular vesicle infusion for amyotrophic lateral sclerosis. Neurodegenerative Disease Management, 1-7 (2024).
Crose, Joshua J: Treating amyotrophic lateral sclerosis with a bone marrow derived mesenchymal stem cell extracellular vesicles. A case report. International Journal of Science and Research Archive. 02(02):167-171 (2021).
Cunningham et al., The therapeutic potential of the mesenchymal stem cell secretome in ischaemic stroke. J Cereb Blood Flow Metab. 38(8):1276-1292 (2018).
Database WPI Week 201851 Thomson Scientific, London, GB; AN 2018-41069T XP002807292, & CN 108 042 572 A (Beijing Doing Time Translational Medicin) May 18, 2018.
Database WPI Week 201877 Thomson Scientific, London, GB; AN 2018-724966 XP002807291, & CN 108 498 452 A (Univ Shanghai Second Med Renji Hospital) Sep. 7, 2018.
DeJong et al.: Extracellular vesicles: potential roles in regenerative medicine. Frontiers in Immunology. 5:608 (2014).
Direct Biologics, LLC Announces the Launch of ExoFlo Exosomes. Press Release (2019).
Direct Biologics Received FDA Approval to Initiate 'Exit-COVID-19,' a Phase II Investigational New Drug Trial. (2020).
Dreschnack et al.: Treatment of idiopathic facial paralysis (Bell's Palsy) and secondary facial paralysis with extracellular vesicles: a pilot safety study. BMC Neurol 23:342 1-9 (2023).
East et al.: Can IV Infusions Of Bone Marrow Derived Mesenchymal Stem Cell Extracellular Vesicles Be The Fountain Of Youth? Journal of Regenerative Biology and Medicine. 1(2):1-10 (2019).
East et al.: Intra-Articular Injection of an Extracellular Vesicle Isolate Product to Treat Hip Labral Tears. Journal of Regenerative Biology and Medicine. J Regen Biol Med. 2019;1(1):1-6 (2019).
East et al.: Intra-Articular Injection of an Extracellular Vesicle Isolate Product to Treat Knee Osteoarthritis in an Athlete. Journal of Biomedical Research and Clinical Investigation. 1(1):1005 (2020).
East et al.: IRB Approved Pilot Safety Study of an Extracellular Vesicle Isolate Product Evaluating the Treatment of Osteoarthritis in Combat-Related Injuries. Stem Cell Res. 1(2)-11 (2020).
East et al.: The Safety Profile of a Bone Marrow-Derived Mesenchymal Stem Cell Extracellular Vesicle Isolate Product. J of Stem Cell Research. 6:026 (2020).
East et al.: Pilot Safety Study of an Extracellular Vesicle Isolate Product for Treatment of Osteoarthritis in Combat-Related Injuries: One Year Follow Up. Genesis-JSCR-2(2)-21:1-10 (2021).
EP19906384.3 Extended European Search Report dated Aug. 29, 2022.
Epifanova et al., [Investigation of mechanisms of action of growth factors of autologous platelet-rich plasma used to treat erectile dysfunction]. Urologiia. Sep. 2017;(4):46-48 (2017) Russian. English Abstract Provided.
Erhardt et al., Association of polymorphisms in P2RX7 and CaMKKb with anxiety disorders. Journal of Affective Disorders 101(1-3):159-168 (2007).
Felgner, Philip L, et al., Lipofection: A Highly Efficient, Lipid-Mediated DNA-Transfection Procedure. Proceedings of the National Academy of Sciences of the United States of America 84(21):7413-7417 (1987).
Fouad et al., Interleukin-18 gene polymorphisms in systemic lupus erythematosus: relation to disease status. Egypt J Immunol. 21:1-12 (2014).
Fu, H et al., Identification of human fetal liver miRNAs by a novel method. FEBS letters 579(17):3849-3854 (2005).

Gennaro, A.R., Remington: The science and practice of pharmacy. 19th edition. 1995. 12 Pages.
Gilhar A. Collapse of immune privilege in alopecia areata: coincidental or substantial? J Invest Dermatol. 130(11):2535-2537 (2010).
Giugliano et al., Erectile dysfunction associates with endothelial dysfunction and raised proinflammatory cytokine levels in obese men. J Endocrinol Invest. 27(7):665-669 (2004).
Guo et al., Exosomes derived from platelet-rich plasma promote the re-epithelization of chronic cutaneous wounds via activation of YAP in a diabetic rat model. Theranostics 7(1):81-96 (2017).
Heijnen, Harry F. et al. Activated Platelets Release Two Types of Membrane Vesicles Microvesicles by Surface Shedding and Exosomes Derived From Exocytosis of Multivesicular Bodies and Alpha-granules. Blood 94(11)3791-3799 (1999).
Hessvik et al.: Current knowledge on exosome biogenesis and release description. Cell. Mol. Life Sci. 75:193-208 (2018).
Hicok et al.: Exosome Origins: Why the Cell Source Matters. Stem Cells Regen Med. 4(1):1-4 (2020).
Hotaling et al., DCCT/EDIC Research Group. Pilot genome-wide association search identifies potential loci for risk of erectile dysfunction in type 1 diabetes using the DCCT/EDIC study cohort. J Urol. 188(2):514-520 (2012).
Hou, Chun et al., Expression of matrix metalloproteinases and tissue inhibitor of matrix metalloproteinases in the hair cycle. Exp Ther Med. 12(1):231-237 (2016).
Howe et al.: The miracle of stem cells. Stemedica Cell Technologies, Inc. 202-210 (2011).
Howe et al., The miracle of stem cells. Stemedica Cell Technologies pp. 202-210 (2011).
Hughes et al., Monoclonal antibody targeting of liposomes to mouse lung in vivo. Cancer Research 49(22):6214-6220 (1989).
Jacob et al., Association of the oxytocin receptor gene (OXTR) in caucasian children and adolescents with autism. Neuroscience Letters 417(1):6-9 (2007).
Jaeger et al., "Improved predictions of secondary structures for RNA", Proceedings of the National Academy of Sciences, vol. 86, No. 20, Oct. 1, 1989, pp. 7706-7710.
Jaeger, John A, et al., [17] Predicting optimal and suboptimal secondary structure for RNA. Methods in Enzymology 183:281-306 (1989).
Japanese Application No. 2021-537063 Office Action dated Dec. 15, 2023.
Japanese Application No. 2021-564403 Office Action dated May 30, 2024.
Johnston et al., A point mutation in PDGFRB causes autosomal-dominant Penttinen syndrome. Am J Hum Genet. 97(3):465-474 (2015).
JP2021-517548 Office Action dated Apr. 4, 2023.
JP2021544344 Office Action dated Dec. 12, 2023, and an English translation.
JP2021546214 Office Action dated Dec. 19, 2023, and a partial English translation.
Julianto et al., Topical delivery of mesenchymal stem cells "secretomes" in wound repair. Acta Med Indones 48(3):217-220 (2016).
Kambur et al., Genetic variation in P2RX7 and pain tolerance. Pain 159(6):1064-1073 (2018).
Kavoussi et al., Recombinant PAI-1 therapy restores myoendothelial junctions and erectile function in PAI-1-deficient mice. Andrologia 47(10):1147-1152 (2015).
Kawabe et al., Localization of TIMP in cycling mouse hair. Development 111(4):877-879 (1991).
Kim et al., Association between interleukin 18 polymorphisms and alopecia areata in Koreans. J Interferon Cytokine Res. 34:349-353 (2014).
Kim et al., Mesenchymal stem cells vs. mesenchymal stem cell secretome for rheumatoid arthritis treatment. JSM Arthritis, vol. 1(1):1001 (2016).
Kim et al.: Wound healing effect of adipose-derived stem cells: A critical role of secretory factors on human dermal fibroblasts. Journal of Dermatological Science. 48:15-24 (2007).
Koizumi et al., Distribution of IL-18 and IL-18 receptor in human skin: various forms of IL-18 are produced in keratinocytes. Arch Dermatol Res. 293(7):325-333 (2001).

(56)  References Cited

OTHER PUBLICATIONS

Kondo, Ayano, and Tsuyoshi Osawa. Establishment of an Extracellular Acidic pH Culture System. Journal of Visualized Experiments 129:e56660, 1-7 (2017).

Lai et al., Androgenic alopecia is associated with less dietary soy, higher blood vanadium and rs1160312 1 polymorphism in Taiwanese communities. PLos One 8(12):e79789, 1-11 (2013).

Lankford, Karen L, et al., Intravenously Delivered Mesenchymal Stem Cell-derived Exosomes Target M2-type Macrophages In The Injured Spinal Cord. PLoS One 13(1):e0190358, 20 Pages (2018).

Lecuyer et al., Dual role of ALCAM in neuroinflammation and blood-brain barrier homeostasis. Proc Natl Acad Sci U S A. 114(4):E524-E533 (2017).

Letsinger, Robert. L. et al. Cholesteryl-conjugated oligonucleotides: Synthesis, properties, and activity as inhibitors of replication of human immunodeficiency virus in cell culture. Proceedings of the National Academy of Sciences of the United States of America 86(17):6553-6556 (1989).

Levitte et al.: Mesenchymal stem cell-derived extracellular vesicles for the treatment of acute rejection in pediatric and adult bowl transplant. American Journal of Transplantation. 1-4 (2023).

Li et al.: Mesenchymal stem cells and acellular products attenuate murine induced colitis. Stem Cell Research & Therapy. 11:515 (2020).

Li et al., Six novel susceptibility loci for early-onset androgenetic alopecia and their unexpected association with common diseases. PLoS Genetics 8(5):e1002746, 1-9 (2012).

Libro et al., Cannabidiol modulates the immunophenotype and inhibits the activation of the inflammasome in human gingival mesenchymal stem cells. Frontiers in Physiology 7:559 (2016).

Lichtenstein, A et al., Liposome-encapsulated silver sulfadiazine (SSD) for the topical treatment of infected burns: thermodynamics of drug encapsulation and kinetics of drug release. Journal of inorganic biochemistry 60(3):187-198 (1995).

Lightner et al.: Bone Marrow Mesenchymal Stem Cell-Derived Extracellular Vesicle Infusion for the Treatment of Respiratory Failure from COVID-19. A Randomized, Placebo-Controlled Dosing Clinical Trial. CHEST. 164(6):1444-1453 (2023).

Lim et al.: Letter to the Editor re: "Exosomes Derived from Bone Marrow Mesenchymal Stem Cells as Treatment for Severe COVID-19" by Sengupta et al. Stem Cells and Development. 00(00) (2020).

Litzinger et al., Biodistribution and immunotargetability of ganglioside-stabilized dioleoylphosphatidylethanolamine liposomes. Biochimica et Biophysica Acta (BBA)-Biomembranes 1104(1):179-187 (1992).

Liu et al., Prediction of male-pattern baldness from genotypes. European Journal of Human Genetics 24:895-902 (2015).

Marcinska et al., Evaluation of DNA variants associated with androgenetic alopecia and their potential to predict male pattern baldness. PLoS One 10(5):1-18, e0127852 (2015).

Massa et al.: Clinical Applications of Mesenchymal Stem/Stromal Cell Derived Extracellular Vesicles: Therapeutic Potential of an Accellular Product. Diagnostics. 10:999 (2020).

Mathieu et al.: Specificities of exosome versus small ectosome secretion revealed by live intracellular tracking of CD63 and CD9. Nat Commun. 12(4389):1-18 (2021).

Mazaheri et al., Ameliorating effect of osteopontin on H(2)O(2)-induced apoptosis of human oligodendrocyte progenitor cells. Cell Mol Neurobiol. 38(4):891-899 (2018).

McDowall et al., The role of activins and follistatins in skin and hair follicle development and function. Cytokine Growth Factor Rev. 19(5-6):415-426 (2008).

McQuillin et al., Case-control studies show that a non-conservative amino-acid change from a glutamine to arginine in the P2RX7 purinergic receptor protein is associated with both bipolar- and unipolar-affective disorders. Molecular Psychiatry 14:614-620 (2008).

Messa et al.: Treatment of a recurrent ischial ulcer with injected exosomes. Journal of Surgical Case Reports. 6:1-3 (2022).

Monsel et al.: Mesenchymal Stem Cell Derived Secretome and Extracellular Vesicles for Acute Lung Injury and Other Inflammatory Lung Diseases. Expert Opin Biol Ther. 16(7):859-871 (2016).

Needleman, Saul B, and Christian D Wunsch. A General Method Applicable to the Search for Similarities in the Amino Acid Sequence of Two Proteins. Journal of Molecular Biology 48(3):443-453 (1970).

Ning et al., SNP@lincTFBS: an integrated database of polymorphisms in human LincRNA transcription factor binding sites. PLoS One 9(7):e103851, 1-8 (2014).

OHSU: Emergency Medicine Newsletter https://www.ohsu.edu/sites/default/files/2024-03/March%202024%20Newsletter%20%28Long%29.pdf (Mar. 2024).

Osborn et al.: A novel extracellular vesicle paradigm for the treatment of COVID-19 induced acute respiratory distress syndrome (ARDS). Respirator Medicine Case Reports. 51:102087 (2024).

Oyanguren-Desez et al., Gain-of-function of P2X7 receptor gene variants in multiple sclerosis. Cell Calcium 50(5):468-472 (2011).

Paicius et al.: Safety and Efficacy of Intravenous ExoFlo in the Treatment of Complex Regional Pain Syndrome. Pain Physician. 26:E851-E857 (2023).

Park et al., Hair growth stimulated by conditioned medium of adipose-derived stem cells is enhanced by hypoxia: evidence of increased growth factor secretion. Biomed Res. 31(1):27-34 (2010).

Patton et al.: Hypoxia alters the release and size distribution of extracellular vesicles in pancreatic cancer cells to support their adaptive survival. Journal of Cellular Biochemistry. 121(1):828-839 (2021).

PCT/US2016/022629 International Preliminary Report on Patentability dated Sep. 28, 2017.

PCT/US2016/022629 International Search Report and Written Opinion dated Aug. 25, 2016.

PCT/US2019/026595 International Preliminary Report on Patentability dated Dec. 1, 2020.

PCT/US2019/026595 International Search Report and Written Opinion dated Jul. 2, 2019.

PCT/US2019/068615 International Search Report and Written Opinion dated Mar. 26, 2020.

PCT/US2020/012359 International Search Report and Written Opinion dated Mar. 24, 2020.

PCT/US2020/015982 International Preliminary Report on Patentability dated Aug. 12, 2021.

PCT/US2020/015982 International Search Report and Written Opinion dated Apr. 24, 2020.

PCT/US2020/018821 International Search Report and Written Opinion dated May 21, 2020.

PCT/US2020/030476 International Search Report and Written Opinion dated Aug. 12, 2020.

PCT/US2020/042762 International Preliminary Report on Patentability dated Jan. 27, 2022.

PCT/US2020/042762 International Search Report and Written Opinion dated Dec. 10, 2020.

PCT/US2021/028686 International Search Report and Written Opinion dated Aug. 16, 2021.

PCT/US2023/065115 International Search Report and Written Opinion dated Sep. 27, 2023.

PCT/US2024/019725 International Search Report and Written Opinion dated Jun. 28, 2024.

PCT/US2024/019725 Invitation to Pay Additional Fees dated May 7, 2024.

PCT/US2024/026444 International Search Report and Written Opinion dated Jul. 15, 2024.

Pearson, William R. and David J. Lipman. Improved Tools for Biological Sequence Comparison. PNAS USA 85(8):2444-2448 (1988).

Pettine et al.: Treating Discogenic Pain with Mesenchymal Stem Cell Exosomes: What Is the Biologic Mechanism of Action. Jacobs Journal of Bone Marrow and Stem Cell Research. 5(1):017 (2019).

Phillips et al.: One month safety study of ExoFlo injection for the treatment of lumbar or cervical radiculopathy in the epidural space. International Journal of Science and Research Archive. 119-124 eISSN:2582-8185 (2021).

Phinney et al.: MSC-Derived Exosomes for Cell-Free Therapy. Stem Cells. 35:851-858 (2017).

(56) References Cited

OTHER PUBLICATIONS

Pietersz et al., Antibody conjugates for the treatment of cancer. Immunological Reviews 129(1):57-80 (1992).

Qi et al.: Exosomes Secreted by Human-Induced Pluripotent Stem Cell-Derived Mesenchymal Stem Cells Repair Critical-Sized Bone Defects through Enhanced Angiogenesis and Osteogenesis in Osteoporotic Rats. International Journal of Biological Sciences 12(7):836-849 (2016).

Qian et al., Vacuum therapy prevents corporeal veno-occlusive dysfunction and penile shrinkage in a cavernosal nerve injured rat model. Asian J Androl. 22(3):274-279 (2020).

Rajan et al., Cannabidiol activates neuronal precursor genes in human gingival mesenchymal stromal cells. Journal of Cellular Biochemistry 118(6):1531-1546 (2016).

Roffler et al., Anti-neoplastic glucuronide prodrug treatment of human tumor cells targeted with a monoclonal antibody-enzyme conjugate. Biochemical Pharmacology 42(10):2062-2065 (1991).

Russian Patent Application No. 2021-1122956 Office Action dated Jul. 6, 2023.

Russian Patent Application No. 2021122956/10 Search Report issued on Jul. 6, 2023.

Saldanha-Araujo et al.: Mesenchymal Stem Cells: A New Piece in the Puzzle of COVID-19 Treatment. Frontiers in Immunology. 11:1563. (2020).

Santos et al., Three-dimensional spheroid cell culture of umbilical cord tissue-derived mesenchymal stromal cells leads to enhanced paracrine induction of wound healing. Stem Cell Res Ther. 6(1):90 (2015).

Sasaki, Gordon: Clinical Use of Extracellular Vesicles in the Management of Male and Female Pattern Hair Loss: A Prelminary Retrospective Institutional Review Board Safety and Efficacy Study. Aesthetic Surgery Journal Open Forum. 1-15 (2022).

Sengupta et al.: Exosomes Derived from Bone Marrow Mesenchymal Stem Cells as Treatment for Severe COVID-19. Stem Cells and Development. 29(12):747-754 (2020).

Sengupta et al.: Response to Lim et al. re "Exosomes Derived from Bone Marrow Mesenchymal Stem Cells as Treatment for Severe COVID-19". Stem Cells and Development. 29(14):879-881 (2020).

Senter et al., Generation of 5-fluorouracil from 5-fluorocytosine by monoclonal antibody- cytosine deaminase conjugates. Bioconjugate Chemistry 2(6):447-451 (1991).

Senter et al., Generation of cytotoxic agents by targeted enzymes. Bioconjugate Chemistry 4(1):3-9 (1993).

Sheinkop et al.: Intra-Articular Injection of an Extracellular Vesicle Isolate Product to Treat Hip Osteoarthritis. International Journal of Recent Scientific Research. 10(12A):36230-36232 (2019).

Shen et al., Four genetic variants interact to confer susceptibility to atopic dermatitis in Chinese Han population. Molecular Genetics and Genomics 290(4):1493-1498 (2015).

Singaporean Application No. 11202106836U Written Opinion dated Dec. 19, 2022.

Sivalingam et al., Single-nucleotide polymorphisms of the interleukin-18 gene promoter region in rheumatoid arthritis patients: protective effect of AA genotype. Tissue Antigens 62:498-504 (2003).

Skovronova et al.: Surface marker expresión in small and medium/large mesenchymal stromal cell-derived extracellular vesicles in naïve or apoptotic condition using orthogonal techniques. bioRxiv. 1-32 (2021).

Smith, Temple F, and Waterman Michael S. Comparison of Biosequences. Advances in applied mathematics 2:482-489 (1981).

Stevanato et al.: Investigation of Content, Stoichiometry and Transfer of miRNA from Human Neural Stem Cell Line Derived Exomes. PLoS One. 11(1):e0146353 (2016).

Suarez-Faritias et al., Alopecia areata profiling shows TH1, TH2, and IL-23 cytokine activation without parallel TH17/TH22 skewing. J Allergy Clin Immunol. 136(5):1277-1287 (2015).

Talegaonkar, The Role of Human MSC Derived Exosomes in the Treatment of Periodontal Diseases, Master's Thesis (2017).

Tamimi et al., Breast cancer susceptibility loci and mammographic density. Breast Cancer Research 10:R66 [1-9] (2008).

Thelen et al., Depending on its nano spacing,ALCAM promotes cell attachment and axon growth. PLoS One 7(12):e40493 (2012).

Toh et al., Advances in mesenchymal stem cell-based strategies for cartilage repair and regeneration. Stem Cell Reviews and Reports 10(5):686-696 (2014).

Toh, et al. MSC exosome as a cell-free MSC therapy for cartilage regeneration: Implications for osteoarthritis treatment. Seminars in Cell & Developmental Biology 67:56-64 (2017).

U.S. Appl. No. 17/059,874 Office Action dated Jul. 11, 2024.

U.S. Appl. No. 17/059,874 Restriction Requirement dated Nov. 8, 2023.

U.S. Appl. No. 17/418,342 Office Action dated Mar. 12, 2024.

U.S. Appl. No. 17/420,500 Office Action dated Jul. 18, 2024.

U.S. Appl. No. 17/427,192 Office Action dated Apr. 17, 2024.

U.S. Serial No. 17/432, 138 Office Action dated Feb. 15, 2024.

U.S. Appl. No. 17/628,011 Office Action dated Jun. 24, 2024.

Vanamee et al., Structural principles of tumor necrosis factor superfamily signaling. Sci Signal. 11(511):eaao4910 (2018).

Vizoso et al.: Mesenchymal Stem CellSecretome: Toward Cell-Free Therapeutic Strategies in Regenerative Medicine.Int. J. Mol. Sci. 18:1852 (2017).

Vogel et al.: Clinical Practice Guideline for the Management of Anorectal Abscess, Fistula-in-Ano, and Rectovaginal Fistula. Dis Colon Recturm. 59(12):1117-1133 (2016).

Vuckovic et al., Cannabinoids and pain: new insights from old molecules. Front Pharmacol. 9:1259 (2018).

Wang et al., Macrophages induce AKT/beta-catenin-dependent Lgr5(+) stem cell activation and hair follicle regeneration through TNF. Nat Commun. 8:14091 (2017).

Wang et al., Upregulation of neuregulin-1 reverses signs of neuropathic pain in rats. Int J Clin Exp Pathol. 7(9):5916-5921 (2014).

Website: https://www.youtube.com/watch?v=0RtcsA5MQPs (2019).

Website: https://www.youtube.com/watch?v=8nvgzHzBRP0 (2021).

Website: https://www.youtube.com/watch?v=dNkcd3x1HBY (2020.

Website: https://www.youtube.com/watch?v=RaV2s6x-clg (2020).

Website: https://www.youtube.com/watch?v=V606jT6aHH0 (2021).

Weiss et al.: Letter to the Editor. Response to Sengupta et al. Stem Cells and Development. 29(24):1533-1534 (2020).

Wesselius et al., Association of P2X7 receptor polymorphisms with bone mineral density and osteoporosis risk in a cohort of Dutch fracture patients. Osteoporosis International 24(4):1235-1246 (2012).

Wilson et al.: Safety of Bone Marrow Derived Mesenchymal Stem Cell Extracellular Vesicle Injection for Lumbar Facet Joint Pain. Regenerative Medicine. 19(1):19-26 (2023).

Xia Xianfeng et al., Secretome from hypoxia-conditioned adipose-derived mesenchymal stem cells promotes the healing of gastric mucosal injury in a rodent model. Biochim Biophys Acta Mol Basis Dis 1864(1):178-188 (2018).

Yan et al., The platelet-derived growth factor receptor/STAT3 signaling pathway regulates the phenotypic transition of corpus cavernosum smooth muscle in rats. PLoS One 12(2):e0172191 (2017).

Yang et al., Cannabidiol regulates gene expression in encephalitogenic T cells using histone methylation and noncoding RNA during experimental autoimmune encephalomyelitis. Sci Rep. 9(1):15780 (2019).

Yepes, M. Urokinase-type plasminogen activator is a modulator of synaptic plasticity in the central nervous system: implications for neurorepair in the ischemic brain. Neural Regen Res. 15(4):620-624 (2020).

Yu et al.: Exosomes Derived from Bone Marrow Mesenchymal Stem Cells as Treatment for Severe COVID-19. Stem Cells & Dev. 29(12):747-754. doi:10.1089/scd.2020.0080 (2020).

Yu et al.: Exosomes Derived from Mesenchymal Stem Cells. Int. J. Mol. Sci. 15:4142-4157 (2014) doi:10.3390/ijms15034142.

Zhao et al., NLRP3 inflammasome activation plays a carcinogenic role through effector cytokine IL-18 in lymphoma. Oncotarget 8(65):108571-108583 (2017).

Zhou et al., Cross-talk between interferon-gamma and interleukin-18 in melanogenesis. J Photochem Photobiol B. 163:133-143 (2016).

Zhou et al., Effects of adipose-derived stem cells plus insulin on erectile function in streptozotocin-induced diabetic rats. Int Urol Nephrol. 48(5):657-669 (2016).

(56)     References Cited

OTHER PUBLICATIONS

Zhou et al., Interleukin-18 augments growth ability of primary human melanocytes by PTEN inactivation through the AKT/NF-KB pathway. Int J Biochem Cell Biol. 45:308-331 (2013).

Zinoviev et al.: Clinical evaluation of the effectiveness of mesenchymal stem cells in thermal burns. Bulletin of the National Medical and Surgical Center named after N.A. Pirogov. 13(4):Abstract (2018).

Zuker, M., On Finding All Suboptimal Foldings Of An RNA Molecule. Science 244(4900):48-52 (1989).

Attur, Mukundan et al. Interleukin 1 receptor antagonist (IL1RN) gene variants predict radiographic severity of knee osteoarthritis and risk of incident disease. Annals of the rheumatic diseases 79(3):400-407 (2020). Published online Dec. 18, 2019.

AU2019416339 Examination Report dated Sep. 16, 2024.

Baberg, Falk et al. Secretome analysis of human bone marrow derived mesenchymal stromal cells. Biochimica et Biophysica Acta (BBA)—Proteins and Proteomics 1867(4):434-441 (2019).

Backlund, Lena et al. Cognitive manic symptoms associated with the P2RX7 gene in bipolar disorder. Bipolar disorders 13(5-6):500-508 (2011).

Barnett, J H, and J W Smoller. The genetics of bipolar disorder. Neuroscience 164(1):331-343 (2009).

Bassir, Seyed Hossein et al. Potential for Stem Cell-based Periodontal Therapy. Journal of Cellular Physiology 231(1):50-61 (2016).

BR2021012661 Office Action dated Sep. 3, 2024, and a partial English translation.

Bracho-Sanchez, Evelyn et al. Suppression of local inflammation via galectin-anchored indoleamine 2, 3-dioxygenase. Nature biomedical engineering 7(9):1156-1169 (2023).

Bruno, Stefania et al. Mesenchymal stem cell-derived microvesicles protect against acute tubular injury. Journal of the American Society of Nephrology 20(5):1053-1067 (2009).

Budhiparama, Nicolaas C. et al. The role of genetic polymorphisms of interleukin-1 (IL-1R1 and IL-1RN) in primary knee osteoarthritis in Indonesia. Scientific reports 13(1):7967, 1-10 (2023).

Bustos, Martha L. et al. Activation of human mesenchymal stem cells impacts their therapeutic abilities in lung injury by increasing interleukin (IL)-10 and IL-1RN levels. Stem cells translational medicine 2(11):884-895 (2013).

Cai, L. et al. A slow release formulation of insulin as a treatment for osteoarthritis. Osteoarthritis and Cartilage 10(9):692-706 (2002).

Cai, Yu et al. Anti-inflammatory and chondroprotective effects of platelet-derived growth factor-BB on osteoarthritis rat models. The Journals of Gerontology: Series A 78(1):51-59 (2023).

Chen, Lei et al. Pre-vascularization Enhances Therapeutic Effects of Human Mesenchymal Stem Cell Sheets in Full Thickness Skin Wound Repair. Theranostics 7(1):117-131 (2017).

Cheng, Daye et al. The relationship between interleukin-18 polymorphisms and allergic disease: a meta-analysis. BioMed Research International 2014(1):290687, 1-11 (2014).

Chia, Shi-Lu et al. Fibroblast growth factor 2 is an intrinsic chondroprotective agent that suppresses ADAMTS-5 and delays cartilage degradation in murine osteoarthritis. Arthritis & rheumatism: official Journal of the American College of rheumatology 60(7):2019-2027 (2009).

Ciavarella, Sabino et al. A peculiar molecular profile of umbilical cord-mesenchymal stromal cells drives their inhibitory effects on multiple myeloma cell growth and tumor progression. Stem cells and development 24(12):1457-1470 (2015).

Cook, Andrew D. et al. Granulocyte-macrophage colony-stimulating factor is a key mediator in experimental osteoarthritis pain and disease development. Arthritis research & therapy 14(5):R199, 1-9 (2012).

Co-pending U.S. Appl. No. 17/429,553 Claims as of Aug. 9, 2021.

Dankbar, Berno et al. Hepatocyte growth factor induction of macrophage chemoattractant protein-1 and osteophyte-inducing factors in osteoarthritis. Journal of orthopaedic research 25(5):569-577 (2007).

De Boeck, Astrid. et al. Bone marrow-derived mesenchymal stem cells promote colorectal cancer progression through paracrine neuregulin 1/HER3 signalling. Gut 62(4):550-560 (2013). Online Published Apr. 25, 2012.

François, Moïra et al. Human MSC suppression correlates with cytokine induction of indoleamine 2, 3-dioxygenase and bystander M2 macrophage differentiation. Molecular therapy 20(1):187-195 (2012).

Gao, Lei et al. Association of endothelial nitric oxide synthase polymorphisms with an increased risk of erectile dysfunction. Asian journal of andrology 19(3):330-337 (2017).

Hamilton, John L. et al. Targeting VEGF and Its Receptors for the Treatment of Osteoarthritis and Associated Pain. Journal of bone and mineral research : the official journal of the American Society for Bone and Mineral Research 31(5):911-924 (2016).

Handayani, Erika Yusticia, and Heri Krisnata Ginting. Osteoarthritis and Hypothyroidism: What's the Association? A Literature Review. Asian Journal of Healthy and Science 3(6):113-119 (2024).

Hara, Tomonori. et al. Genetics of bipolar disorder: insights into its complex architecture and biology from common and rare variants. Journal of human genetics 68(3):183-191 (2023). Published online May 26, 2022.

Haynesworth, Stephen E. et al. Cytokine expression by human marrow-derived mesenchymal progenitor cells in vitro: Effects of dexamethasone and IL-1α. Journal of cellular physiology 166(3):585-592 (1996).

Ho, Chih-Yi et al. Clinical and genetic aspects of alopecia areata: a cutting edge review. Genes 14(7):1362, 1-20 (2023).

Jorgenson, Eric et al. Genetic variation in the SIM1 locus is associated with erectile dysfunction. Proceedings of the National Academy of Sciences 115(43):11018-11023 (2018).

Kiener, Hans P. et al. Tumor necrosis factor a promotes the expression of stem cell factor in synovial fibroblasts and their capacity to induce mast cell chemotaxis. Arthritis & Rheumatism: Official Journal of the American College of Rheumatology 43(1):164-174 (2000).

Kinane, Denis F. et al. Periodontal diseases. Nature reviews Disease primers 3:17038, 1-14 (2017).

Knights, Alexander J. et al. Synovial macrophage diversity and activation of M-CSF signaling in post-traumatic osteoarthritis. bioRxiv :1-29 (2023).

Li, Chengxin. et al. Association of thyroid hormone with osteoarthritis: from mendelian randomization and RNA sequencing analysis. Journal of Orthopaedic Surgery and Research 19(1):429, 1-11 (2024).

Li, Yun-Xuan et al. FGF1 reduces cartilage injury in osteoarthritis via regulating AMPK/Nrf2 pathway. Journal of Molecular Histology 54(5):427-438 (2023).

Lightner, Amy L. et al. Mesenchymal Stem Cell Extracellular Vesicles as a New Treatment Paradigm in Solid Abdominal Organ Transplantation: A Case Series. Stem Cells and Development. 33(5-6):107-115 (2024).

Lin, Shih-Chao et al. Microencapsulated recombinant human epidermal growth factor ameliorates osteoarthritis in a murine model. Evidence-Based Complementary and Alternative Medicine 2021(1):9163279, 1-10 (2021).

Lin, WeiYu et al. Function of CSF1 and IL34 in Macrophage Homeostasis, Inflammation, and Cancer. Frontiers in immunology 10:2019, 1-18 (2019).

Lou, Danning et al. Single nucleotide polymorphisms in the non-coding region of STIM1 gene are associated with Parkinson disease risk in Chinese Han population. Medicine 99(9):e19234, 1-10 (2020).

Luo, Shi-Xing. et al. Genetic polymorphisms of interleukin-16 and risk of knee osteoarthritis. PloS one 10(5):e0123442, 1-12 (2015).

Luo, Ziwei. et al. IL16 Regulates Osteoarthritis Progression as a Target Gene of Novel-miR-81. Cartilage 15(2):175-183 (2024). Published online Apr. 21, 2023.

Massicotte, F. et al. Can altered production of interleukin-1β, interleukin-6, transforming growth factor-β and prostaglandin E2 by isolated human subchondral osteoblasts identify two subgroups of osteoarthritic patients. Osteoarthritis and cartilage 10(6):491-500 (2002).

(56)                    References Cited

OTHER PUBLICATIONS

Massicotte, Frederic et al. Modulation of insulin-like growth factor 1 levels in human osteoarthritic subchondral bone osteoblasts. Bone 38(3):333-341 (2006). Published online Oct. 27, 2005.

Muratovic, Dzenita. et al. Elevated levels of active Transforming Growth Factor β1 in the subchondral bone relate spatially to cartilage loss and impaired bone quality in human knee osteoarthritis. Osteoarthritis and cartilage 30(6):896-907 (2022).

Nagao, Masashi et al. Vascular endothelial growth factor in cartilage development and osteoarthritis. Scientific reports 7(1):13027, 1-16 (2017).

Nakamura, Yoshihiro et al. Mesenchymal-stem-cell-derived exosomes accelerate skeletal muscle regeneration. FEBS letters 589(11):1257-1265 (2015).

Papadopoulos, Konstantinos I. et al. Novel use of intraarticular granulocyte colony stimulating factor (hG-CSF) combined with activated autologous peripheral blood stem cells mobilized with systemic hG-CSF: safe and efficient in early osteoarthritis. Cartilage 13(1_suppl):1671S-1674S (2021).

Papathanasiou, Ioanna et al. Bone morphogenetic protein-2-induced Wnt/β-catenin signaling pathway activation through enhanced low-density-lipoprotein receptor-related protein 5 catabolic activity contributes to hypertrophy in osteoarthritic chondrocytes. Arthritis research & therapy 14(2):R82, 1-14 (2012).

Park, Hang-soo et al. Human BM-MSC secretome enhances human granulosa cell proliferation and steroidogenesis and restores ovarian function in primary ovarian insufficiency mouse model. Scientific reports 11(1):4525, 1-12 (2021).

Partain, Brittany D. et al. Intra-articular delivery of an indoleamine 2, 3-dioxygenase galectin-3 fusion protein for osteoarthritis treatment in male Lewis rats. Arthritis Research & Therapy 25(1):173, 1-15 (2023).

PCT/US2024/033022 International Search Report and Written Opinion dated Sep. 3, 2024.

PCT/US2024/033123 International Search Report and Written Opinion dated Sep. 17, 2024.

Ragni, Enrico. et al. Secreted factors and extracellular vesicles account for the immunomodulatory and tissue regenerative properties of bone-marrow-derived mesenchymal stromal cells for osteoarthritis. Cells 11(21):3501, 1-21 (2022).

Rhee, Sung-Mi. et al. Injectable Tissue-engineered Soft Tissue for Tissue Augmentation. Journal of Korean Medical Science 29(Suppl3):S170-S175 (2014).

Rodriguez-Fontenla, Cristina. et al. Association of a BMP5 microsatellite with knee osteoarthritis: case-control study. Arthritis Research & Therapy 14(6):R257, 1-8 (2012).

Roman-Blas, Jorge A. et al. Osteoarthritis associated with estrogen deficiency. Arthritis research & therapy 11(5):241, 1-14 (2009).

RU2021122946 Examination Report dated Sep. 16, 2024.

Salisbury et al.: SNP and haplotype variation in the human genome. Mutat Res 526(1-2):53-61 (2003).

Shao, Yan. et al. BMP5 silencing inhibits chondrocyte senescence and apoptosis as well as osteoarthritis progression in mice. Aging (albany NY) 13(7):9646-9664 (2021).

Shen, Jie. TGF-beta signaling and the development of osteoarthritis. Bone research 2(1):1-7 (2014).

Spencer, Paige S, and Jose M Barral. Genetic Code Redundancy and Its Influence on the Encoded Polypeptides. Computational and Structural Biotechnology Journal 1:e201204006, 1-8 (2012).

Sun, JiaYang et al. The healing effects of conditioned medium derived from mesenchymal stem cells on radiation-induced skin wounds in rats. Cell transplantation 28(1):105-115 (2019).

U.S. Appl. No. 17/418,342 Office Action dated Sep. 5, 2024.

U.S. Appl. No. 17/606,514 Office Action dated Sep. 16, 2024.

Usmani, Shirine E. et al. Transforming growth factor-alpha induces endothelin receptor A expression in osteoarthritis. Journal of Orthopaedic Research 30(9): 1391-1397 (2012).

Usmani, Shirine E. The Role of Transforming Growth Factor Alpha in Osteoarthritis and Skeletal Development. Electronic Thesis and Dissertation Repository (2012).

Van Helvoort, E M. et al. The Role of Interleukin-4 and Interleukin-10 in Osteoarthritic Joint Disease: A Systematic Narrative Review. Cartilage 13(2):19476035221098167, 1-14 (2022).

Von Kaeppler, Ericka P. et al. Interleukin 4 promotes anti-inflammatory macrophages that clear cartilage debris and inhibits osteoclast development to protect against osteoarthritis. Clinical immunology 229:108784, 1-10 (2021).

Wang, Hai-jun et al. Suppression of experimental osteoarthritis by adenovirus-mediated double gene transfer. Chinese medical journal 119(16):1365-1373 (2006).

Wang, Jiaqi et al. Exosomes: A Novel Strategy for Treatment and Prevention of Diseases. Frontiers in Pharmacology 8:300, 1-13 (2017).

Watkins, Linda R. et al. Targeted interleukin-10 plasmid DNA therapy in the treatment of osteoarthritis: Toxicology and pain efficacy assessments. Brain, behavior, and immunity 90:155-166 (2020).

Wen, Caining et al. Insulin-like growth factor-1 in articular cartilage repair for osteoarthritis treatment. Arthritis research & therapy 23(1):277, 1-9 (2021).

Wilkins, James M. et al. Association of a functional microsatellite within intron 1 of the BMP5 gene with susceptibility to osteoarthritis. BMC medical genetics 10:141, 1-10 (2009).

Yap, Chloe X. et al. Dissection of Genetic Variation and Evidence for Pleiotropy in Male Pattern Baldness. Nature communications 9(1):5407, 1-12 (2018).

Ye, Hantao et al. MST1 knockdown inhibits osteoarthritis progression through Parkin-mediated mitophagy and Nrf2/NF-KB signalling pathway. Journal of cellular and molecular medicine 28(11):e18476, 1-15 (2024).

Zafranskaya, M. et al. PGE2 contributes to in vitro MSC-mediated inhibition of non-specific and antigen-specific T cell proliferation in MS patients. Scandinavian journal of immunology 78(5):455-462 (2013).

Zhao, Xiaoyi et al. RNA-seq characterization of histamine-releasing mast cells as potential therapeutic target of osteoarthritis. Clinical Immunology 244:109117 (2022).

Zhu, Pengfei et al. Recombinant platelet-derived growth factor-BB alleviates osteoarthritis in a rat model by decreasing chondrocyte apoptosis in vitro and in vivo. Journal of Cellular and Molecular Medicine 25(15):7472-7484 (2021).

Zohora, Fatema Tuz et al. Secretome-based acellular therapy of bone marrow-derived mesenchymal stem cells in degenerative and immunological disorders: a narrative review. Heliyon 9(7):e18120, 1-20 (2023).

Ball CM, Meunier M, Galatz LM, Calfee R, Yamaguchi K. Arthroscopic treatment of post-traumatic elbow contracture. Journal of Shoulder and Elbow Surgery. 2002;11(6):624-629.

Beitzel K, Solovyova O, Cote MP, Apostolakos J, Russell RP, McCarthy MB, et al. The future Role of Mesenchymal Stem Cells in the Management of shoulder Disorders. Arthroscopy. 2013; 29(10):1702-11.

Biswas D, Wysocki RW, Cohen MS: Primary and Secondary Arthritis of the Elbow. Arthritis. May 27, 2013.

Black LL, Gaynor J, Adams C, Dhupa S, Sams AE, Taylor R, et al. Effect of intraarticular injection of autologous adipose-derived mesenchymal stem and regenerative cells on clinical signs of chronic osteoarthritis of the elbow joint in dogs. Vet Ther. 2008; 9:192-200.

Black LL, Gaynor J, Gahring D, et al. Effect of adipose-derived mesenchymal stem and regenerative cells on lameness in dogs with chronic osteoarthritis of the coxofemoral joints: a randomized, double-blinded, multicenter, controlled trial. Vet Ther 2007; 8:272-84.

Caplan AI, Correa D. The MSC: An injury drugstore. Cell Stem Cell. Jul. 8, 2011;9(1):11-5.

Caplan AI, Dennis JE. Mesenchymal stem cells as trophic mediators. J Cell Biochem 2006; 98:1076-1084.

Centers for Disease Control and Prevention (CDC) Prevalence and most common causes of disability among adults—United States, 2005. Morbidity and Mortality Weekly Report 2009; 58(16):421-426.

(56)          References Cited

OTHER PUBLICATIONS

Chang CH, Huo TF, Lin FH, et al. Tissue engineering based cartilage repair with mesenchymal stem cells in a porcine model. J Orthop Res 2011; 29:1874-80.

Chang Y, Wu K, Harn H. Exosomes and Stem Cells in Degenerative Disease Diagnosis and Therapy. Cell Transplantation, Apr. 25, 2018.

Cheng L, Zhang K, Wu S, Cui M, Xu T. Focus on Mesenchymal Stem Cell-Derived Exosomes: opportunities and Challenges in Cell-Free Therapy. Stem Cells Int. 2017; 2017:6305295.

Chew E, Prakash R, Khan W, Mesenchymal Stem Cells in Human Meniscal Regeneration: A Systemic Review. Ann Med Surg. 2017; 24:3-7.

Dwyer MK1, Jones HL, Hogan MG, Field RE, McCarthy JC, Noble PC. The acetabular labrum regulates fluid circulation of the hip joint during functional activities. Am J Sports Med. 2014; 42(4):812-9.

Fan J., Varshney RR, Ren L., Wang DA. Synovium-Derived Mesenchymal stem cells: A new source for musculoskeletal regeneration. Tissue Engineering Part B Review Mar. 2009;15(1):75-86.

Feng G et al. Transplantation of mesenchymal stem cells and nucleus pulposus cells in a degenerative disc model in rabbits: a comparison of 2 cell types as potential candidates for disc regeneration. J Neurosurgery Spine 2011; 14:322-9.

Freitag J, Bates D. Mesenchymal stem cell therapy in the treatment of Osteoarthritis: reparative pathways,safety, and efficacy: A Review. BMC Musculoskeletal Disorders. 2016; 17:230.

Frisbie DD, Smith RKW (2010) Clinical update on the use of mesenchymal stem cells in equine orthopaedics. Equine Veterinary Journal, 42:86-9.

Guerico A, Di Marco P, Casella S, et al. Production of canine mesenchymal stem cells from adipose tissue and their application in dogs with chronic osteoarthritis of the humeroradial joints. Cell Biol Int 2012; 36:189-94.

Harris JD.Hip labral repair: options and outcomes. Curr Rev Musculoskelet Med. 2016; 9(4):361-367.

Hiyama A, Mochida J, Iwashina T, Omi H, Watanabe T, Serigano K, Tamura F, Sakai D. Transplantation of mesenchymal stem cells in a canine disc degeneration model. J Orthop Res 2008; 26:589-600.

Kellgren J, Lawrence J. Radiological assessment of Osteo-Arthrosis. Ann Rheum Dis Dec. 1957; 16(4):494-502.

Kelly EW, Bryce R, Coghlan J, Bell S. Arthroscopic debridement without radial head excision of the osteoarthritic elbow. Arthroscopy. 2007;23(2):151-156.

Koga H., Muneta T., et al. Synovial Stem cells are Regionally Specified According to Local Microenvironments after Implantation for Cartilage Regeneration. Stem Cells 2007; 25: 689-96.

Krych AJ, Kuzma SA, Kovachevich R, Hudgens JL, Levy BA. Modest Mid-term outcomes after Isolated Arthroscopic Debridement of Acetabular Tears. Knee Surg Sports Traumatol Arthrosc. 2014;22(4):763-7.

Lee KB, Hui JH, Song IC, et al. Injectable mesenchymal stem cell therapy for large cartilage defects-a porcine model. Stem Cells 2007; 25:2964-71.

Li Z, Wang Y, Xiao K, Weng X. Emerging Role of Exosomes in the Joint Diseases. Cell Physiol Biochem. 2018; 47(5):2008-2017.

Little CP, Graham AJ, Carr AJ. Total elbow arthroplasty: a systematic review of the literature in the English language until the end of 2003. Journal of Bone and Joint Surgery. 2005;87(4):437-444.

Mokbel A, El-Tookhy O, Shamaa AA, et al. Homing and efficacy of intra-articular injection of autologous mesenchymal stem cells in experimental chondral defects in dogs. Clin Exp Rheumatol 2011; 29:275-84.

Murphy JM, Fink DJ, Hunziker EB, et al. Stem cell therapy in a caprine model of osteoarthritis. Arthritis Rheum 2003; 48:3464-74.

Nguyen D, Proper SIW, MacDermid JC, King GJW, Faber KJ. Functional outcomes of arthroscopic capsular release of the elbow. Arthroscopy. 2006;22(8):842-849.

Pettine KA, Murphy MB, Suzuki RK, Sand TT (2015) Percutaneous injection of Autologous bone marrow concentrate significantly reduces lumbar discogenic pain through twelve months. Stem Cells 33:146-56.

Pettine KP, Dordevic M. The Biologic Treatment of Osteoarthritis with Mesenchymal Stem Cell Exosomes: The Future is now. J Stem Cell Res Dev Ther. 2019; 1-5.

Pettine KP, Dordevic M.TibialMetaphyseal Injection with Bone Marrow Concentrate to Treat Knee Arthritis. American J Stem Cell Res Ther. 2018; 2(1):5-10.

Pettine KP, Suzuki R. Autogenous Bone Marrow Concentrate for the treatment of osteoarthritis of the knee, hip and shoulder in former NFL players. J Stem Cell Res Ther. 2018; 4(1):9-13.

Philippon MJ, Nepple JJ, Campbell KJ, Dornan GJ, Jansson KS, LaPrade RF, et al. The hip fluid seal-part I: the effect of an acetabularlabral tear, repair, resection, and reconstruction on hip fluid pressurization. Knee Surg Sports Traumatol Arthrosc. 2014; 22(4):722-9.

Savoie FH, Nunley PD, Field LD. Arthroscopic management of the arthritic elbow: indications, technique, and results. Journal of Shoulder and Elbow Surgery. 1999;8(3):214-219.

Seldes RM, Tan V, Hunt J, Katz M, Winiarsky R, Fitzgerald RH Jr. Anatomy, histologic features, and vascularity of the adult acetabular labrum. Clin Orthop Relat Res. 2001; 382:232-40.

Smith RKW, Korda M, Blunn GW, Goodship AE (2003) Isolation and implantation of autologous equine mesenchymal stem cells from bone marrow into the superficial digital flexor tendon as a potential novel treatment. Equine Veterinary Journal, 35:99-102.

Smith RKW. Mesenchymal Stem Cell Therapy in Equine Tendinopathy. Disabil Rehabil (2008) 30:20-22, 1752-1758.

Vangsness CT, Farr J, Boyd J, Dellaero. Adult human mesenchymal stem cells delivered via intra-articular injection to the knee following partial medial meniscectomy: a randomized, double-blind controlled study. JBJS. 2014:90-98.

Zhang S, Chuah SJ, Lai RC, Hui JHP, Lim SK, Toh WS. MSC Exosomes Mediate Cartilage Repair by Enhancing Proliferation, Attenuating Apoptosis and Modulating Immune Reactivity. Biomaterials. Feb. 2018; 156:16-27.

Zhao L, Kaye AD. Stem Cells for the Treatment of Knee Osteoarthritis: A Comprehensive Review. Pain Physician. 2018; 21:229-241.

Yang F. et al., Effect of Mesenchymal Stem Cells in Autoimmune Arthritis.Eur. Med. J., Dec. 31, 2018, vol. 34, pp. 130-137.

Mancuso P. et al., Mesenchymal Stem Cell Therapy for Osteoarthritis: The Critical Role of the Cell Secretome. Front. Bioeng. Biotechnol., Jan. 29, 2019, vol. 7, pp. 9: 1-9.

Dong, Liang. et al. Treatment of MSCs with Wnt1a-conditioned medium activates DP cells and promotes hair follicle regrowth. Scientific Reports 4(1):5432, 1-9 (2014).

Kim, Soochong et al. Insulin-like growth factor-1 regulates platelet activation through PI3-K alpha isoform. Blood, The Journal of the American Society of Hematology 110(13):4206-4213 (2007).

Rolandsson Enes, Sara et al. Quantitative proteomic characterization of lung-MSC and bone marrow-MSC using DIA-mass spectrometry. Scientific Reports 7(1):9316, 1-12 (2017).

Romanov, Yu A. et al. Comparative Analysis of Secretome of Human Umbilical Cord- and Bone Marrow-Derived Multipotent Mesenchymal Stromal Cells. Bulletin of Experimental Biology and Medicine 166(4):535-540 (2019).

Sugimoto, K.: Basic knowledge of ultrasonography in sports injury and trauma. Medical Technology. 43(5):440-444 (2015).

Ueshima et al.: Imaging Diagnosis of Hip Diseases-Diagnostic Imaging of Glenohumeral Labrum Injuries. MB Orthop. 26(5):191-197 (2013).

U.S. Appl. No. 17/059,874 Office Action dated Dec. 30, 2024.

U.S. Appl. No. 17/418,342 Office Action dated Dec. 30, 2024.

U.S. Appl. No. 17/420,500 Office Action dated Jan. 30, 2025.

360 Health Alert Newsletter: 2023 Research: Advanced use of Extracellular Vesicles for Today's Top CHRONIC Disorders (2023).

Abraham et al.: Mesenchymal stem cell-derived extracellular vesicles for the treatment of acute respiratory distress syndrome. Stem Cells Transl Med. 9(1):28-38 (2019).

Aggarwal, Sudeepta. et al. Human mesenchymal stem cells modulate allogeneic immune cell responses. Blood 105(4):1815-1822 (2005).

Alipoor, Shamila D. et al. Exosomes and Exosomal miRNA in Respiratory Diseases. Mediators Inflamm 2016:5628404, 1-11 (2016).

(56)                    References Cited

OTHER PUBLICATIONS

Allison, Malorye. Genzyme backs Osiris, despite Prochymal flop. Nature Biotechnology 27(11):966-967 (2009).

Anderson, Monique R. et al. Exosomes in Viral Disease. Neurotherapeutics 13(3):535-546 (2016).

Arima, Ken. et al. Autologous Transplantation of Bone Marrow Mononuclear Cells Improved Ischemic Peripheral Neuropathy in Humans. Journal of the American College of Cardiology 56(3):238-239 (2010).

Barbash, Israel M. et al. Systemic delivery of bone marrow-derived mesenchymal stem cells to the infarcted myocardium: feasibility, cell migration, and body distribution. Circulation 108(7):863-868 (2003).

Bari et al.: Mesenchymal Stromal Cell Secretome for Severe COVID-19 Infections: Premises for the Therapeutic Use. Cells. 9(924):1-5 (2020).

Barnhoorn, Marieke C. et al. Long-term Evaluation of Allogeneic Bone Marrow-derived Mesenchymal Stromal Cell Therapy for Crohn's Disease Perianal Fistulas. Journal of Crohn's and Colitis 14(1):64-70 (2020).

Bartholomew, Amelia. et al. Mesenchymal stem cells suppress lymphocyte proliferation in vitro and prolong skin graft survival in vivo. Exp Hematol 30(1): 42-48 (2002).

Behr, Luc. et al. Intra renal arterial injection of autologous mesenchymal stem cells in an ovine model in the postischemic kidney. Nephron Physiology 107(3):p65-p76 (2007).

Bonovas, Stefanos. et al. Biologic Therapies and Risk of Infection and Malignancy in Patients With Inflammatory Bowel Disease: A Systematic Review and Network Meta-analysis. Clin Gastroenterol Hepatol 14(10):1385-1397.e10 (2016).

Burian, Egon. et al. Effect of hypoxia on the proliferation of porcine bone marrow-derived mesenchymal stem cells and adipose-derived mesenchymal stem cells in 2- and 3-dimensional culture. Journal of cranio-maxillo-facial surgery45(3):414-419 (2017). Published online Dec. 20, 2016.

Cao, Yantian. et al. Efficacy of Stem Cells Therapy for Crohn's Fistula: a Meta-analysis and Systematic Review. Stem Cell Research and Therapy 12(1):32, 1-11 (2021).

Caron, Benedicte. et al. Endpoints for Perianal Crohn's Disease Trials: past, present and future. Journal of Crohn's and Colitis 15(8):1387-1398 (2021).

Chambaz, Marion. et al. Deep Remission on Magnetic Resonance Imaging Impacts Outcomes of Perianal Fistulizing Crohn's Disease. Digestive and Liver Disease 51(3):358-363 (2019).

Chang, Shannon. et al. A Review of Available Medical Therapies to Treat Moderate-to-Severe Inflammatory Bowel Disease. Am J Gastroenterol 119(1):55-80 (2024). Published Online Aug. 24, 2023.

Chen, George L. et al. Remestemcel-L for Acute Graft-versus-host Disease Therapy. Expert Opinion on Biological Therapy 14(2):261-269 (2014).

Chen, Liwen. et al. Paracrine factors of mesenchymal stem cells recruit macrophages and endothelial lineage cells and enhance wound healing. PloS one 3(4):e1886, 1-12 (2008).

Chinese Clinical Trial Registry ChiCTR2000030261. A Study for the key technology of mesenchymal stem cells exosomes atomization in the treatment of novel coronavirus phnumonia (COVID019). Record Version as of Feb. 26, 2020.

Cho, Yong Beom. et al. Autologous adipose tissue-derived stem cells for the treatment of Crohn's fistula: a phase I clinical study. Cell Transplant 22(2):279-285 (2013) Published online Sep. 21, 2012.

Cho, Yong Beom. et al. Long-term results of adipose-derived stem cell therapy for the treatment of Crohn's fistula. Stem Cells Transl Med 4(5):532-537 (2015).

Ciccocioppo et al., Autologous bone marrow-derived mesenchymal stromal cells in the treatment of fistulising Crohn's disease. Gut 60(6):788-798 (2011).

Colombel, Jean-Frédéric. et al. Adalimumab for maintenance of clinical response and remission in patients with Crohn's disease: the CHARM trial. Gastroenterology 132(1):52-65 (2007) Published online Nov. 29, 2006.

Colombo, M. et al., "Biogenesis, secretion, and intercellular interactions of exosomes and other extracellular vesicles." Annu Rev Cell Dev Biol, 2014, 30:255-289.

Co-pending U.S. Appl. U.S. Appl. No. 19/098,197 Claims as of Apr. 2, 2025.

Co-pending U.S. Appl. U.S. Appl. No. 18/988,110 Claims as of Dec. 19, 2024.

Crose, Joshua James. Treating amyotrophic lateral sclerosis with a bone marrow derived mesenchymal stem cell extracellular vesicles—A case report. IJSRA 2:167-171 (2021).

Cui et al.: Plant extracellular vesicles. Protoplasma. 1-10 (2019).

Da Costa Goncalves, Fabiany. et al. Intravenous vs intraperitoneal mesenchymal stem cells administration: what is the best route for treating experimental colitis?. World Journal of Gastroenterology 20(48):18228-18239 (2014).

Daly, Andrew. Remestemcel-L, The First Cellular Therapy Product for the Treatment of Graft-versus-host Disease. Drugs Today (Barc) 48(12):773-783 (2012).

De La Portilla, Fernando. et al. Local mesenchymal stem cell therapy in experimentally induced colitis in the rat. International Journal of Stem Cells 11(1):39-47 (2018).

Derkus, Burak. et al. A new approach in stem cell research-Exosomes: Their mechanism of action via cellular pathways. Cell Biol 41(5):466-475 (2017).

Dietz, Allan B. et al. Autologous Mesenchymal Stem Cells, Applied in a Bioabsorbable Matrix, for Treatment of Perianal Fistulas in Patients With Crohn's Disease. Gastroenterology 153(1):59-62.e2 (2017).

Drela, Katarzyna. et al. Low oxygen atmosphere facilitates proliferation and maintains undifferentiated state of umbilical cord mesenchymal stem cells in an hypoxia inducible factor-dependent manner. Cytotherapy 16(7):881-892 (2014).

Duijvestein, Marjolijn. et al. Autologous bone marrow-derived mesenchymal stromal cell treatment for refractory luminal Crohn's disease: results of a phase I study. Gut 59(12):1662-1669 (2010).

East, J., and M. Dordevic. Pilot safety study of an extracellular vesicle isolate product for treatment of osteoarthritis in combat-related injuries: one year follow up. Journal of Stem Cell Research 2(2):21, 1-10 (2021).

East, Johnny. et al. IRB \ Safety Study of an Extracellular Vesicle Isolate Product Evaluating the Treatment of Osteoarthritis in Combat-Related Injuries. Stem Cell Research 1(2):1-10 (2020).

Eirin, Alfonso. et al. Adipose tissue-derived mesenchymal stem cells improve revascularization outcomes to restore renal function in swine atherosclerotic renal artery stenosis. Stem cells 30(5):1030-1041 (2012).

Eirin, Alfonso. et al. Mesenchymal stem cell-derived extracellular vesicles attenuate kidney inflammation. Kidney international 92(1):114-124 (2017).

English, Karen. Mechanisms of Mesenchymal Stromal Cell Immunomodulation. Immunology and Cell Biology 91(1):19-26 (2013).

Falloon, Katherine A, and Claudio Fiocchi. Current Therapy in Inflammatory Bowel Disease: Why and How We Need to Change?. Innovations 6(1):40-49 (2022).

Ferrante, Marc. et al. Validation of Endoscopic Activity Scores in Patients with Crohn's Disease Based on a Post Hoc Analysis of Data From SONIC. Gastroenterology 145(5):978-986 (2013).

Fischer, Uwe M. et al. Pulmonary passage is a major obstacle for intravenous stem cell delivery: the pulmonary first-pass effect. Stem cells and development 18(5):683-692 (2009).

Forbes, Geoffrey M. et al. A phase 2 study of allogeneic mesenchymal stromal cells for luminal Crohn's disease refractory to biologic therapy. Clin Gastroenterol Hepatol 12(1):64-71 (2014). Published online Jul. 19, 2013.

Freyman, Toby. et al. A quantitative, randomized study evaluating three methods of mesenchymal stem cell delivery following myocardial infarction. European heart journal 27(9):1114-1122 (2006).

(56)     References Cited

OTHER PUBLICATIONS

Garcia-Olmo, Damian. et al. Autologous stem cell transplantation for treatment of rectovaginal fistula in perianal Crohn's disease: a new cell-based therapy. Int J Colorectal Dis 18(5):451-454 (2003).

Garcia-Olmo, Damian. et al. Expanded adipose-derived stem cells for the treatment of complex perianal fistula: a phase II clinical trial. Dis Colon Rectum 52(1):79-86 (2009).

Garcia-Olmo, Damian. et al. Follow-up Study to Evaluate the Long-term Safety and Efficacy of Darvadstrocel (Mesenchymal Stem Cell Treatment) in Patients With Perianal Fistulizing Crohn's Disease: Admire-cd Phase 3 Randomized Controlled Trial. Diseases of the Colon and Rectum 65(5):713-720 (2022).

Garcia-Olmo, Damián. et al. A phase I clinical trial of the treatment of Crohn's fistula by adipose mesenchymal stem cell transplantation. Dis Colon Rectum 48(7):1416-1423 (2005).

Gharibi, Tohid et al. Immunomodulatory Characteristics of Mesenchymal Stem Cells and Their Role in the Treatment of Multiple Sclerosis. Cellular Immunology 293(2):113-121 (2015).

Gonzalez, Manuel A. et al. Adipose-derived mesenchymal stem cells alleviate experimental colitis by inhibiting inflammatory and autoimmune responses. Gastroenterology 136(3):978-989 (2009).

Gonzalez-Rey, Elena et al. Human adult stem cells derived from adipose tissue protect against experimental colitis and sepsis. Gut 58(7):929-939 (2009).

Guyatt, Gordon. et al. A New Measure of Health Status for Clinical Trials in Inflammatory Bowel Disease. Gastroenterology 96(2):804-810 (1989).

Hanauer, Stephen B, et al. Human anti-tumor necrosis factor monoclonal antibody (adalimumab) in Crohn's disease: the CLASSIC-I trial. Gastroenterology 130(2):323-333 (2006).

Hanauer, Stephen B. et al. Maintenance infliximab for Crohn's disease: the Accent I randomised trial. The Lancet 359(9317):1541-1549 (2002).

Hare, Joshua M. et al. A randomized, double-blind, placebo-controlled, dose-escalation study of intravenous adult human mesenchymal stem cells (prochymal) after acute myocardial infarction. J Am Coll Cardiol. 54(24):2277-2286 (2009).

Hazehara-Kunitomo, Yuri. et al. Acidic Pre-conditioning Enhances the Stem Cell Phenotype of Human Bone Marrow Stem/progenitor Cells. International Journal of Molecular Sciences 20(5):1097, 1-10 (2019).

He, Xiao-Wen. et al. Systemic Infusion of Bone Marrow-derived Mesenchymal Stem Cells for Treatment of Experimental Colitis in Mice. Digestive Diseases and Sciences 57:3136-3144 (2012).

Hermann, Jacek. et al. Treatment of Crohn's Anal Fistulas Guided by Magnetic Resonance Imaging. Przegląd Gastroenterologiczny 14(1):55-61 (2019).

Hessvik, Nina Pettersen, and Alicia Llorente. Current knowledge on exosome biogenesis and release. Cell Mol Life Sci 75(2):193-208 (2018).

Hindryckx, Pieter. et al. Development and Validation of a Magnetic Resonance Index for Assessing Fistulas in Patients With Crohn's Disease. Gastroenterology 157(5):1233-1244 (2019).

Horton, Jason A. et al. Mesenchymal Stem Cells Inhibit Cutaneous Radiation-induced Fibrosis by Suppressing Chronic Inflammation. Stem Cells 31(10):2231-2241 (2013).

Howell, T. Howard. et al. A Phase I/II Clinical Trial to Evaluate a Combination of Recombinant Human Platelet-derived Growth Factor-BB and Recombinant Human Insulin-like Growth Factor-I in Patients with Periodontal Disease. Journal of Periodontology 68(12):1186-1193 (1997).

Hu, Jianxia. et al. Safety and therapeutic effect of mesenchymal stem cell infusion on moderate to severe ulcerative colitis. Exp Ther Med 12(5):2983-2989 (2016).

Huang, Lina. et al. Exosomes in mesenchymal stem cells, a new therapeutic strategy for cardiovascular diseases?. Int J Biol Sci 11(2):238-245 (2015).

Istanbul Med Assist further considers whether exosomes work for hair loss (IMA) https://www.istanbulmedassist.com/blog/do-exosomes-really-work-for-hair-loss/#:~:text=Do%20Exosomes%20Actually%20Work?,%2C%20and%20overall%20health (2024).

Kalladka, et al. Human Neural Stem Cells In Patients With Chronic Ischaemic Stroke (PISCES): A Phase 1, First-in-man Study. Lancet 388(10046):787-796 (2016).

Kato, Jiro. et al. Mesenchymal stem cells ameliorate impaired wound healing through enhancing keratinocyte functions in diabetic foot ulcerations on the plantar skin of rats. Journal of Diabetes and its Complications 28(5):588-595 (2014).

Kebriaei, Partow. et al. Adult Human Mesenchymal Stem Cells Added to Corticosteroid Therapy for the Treatment of Acute Graft-versus-host Disease. Biology of Blood and Marrow Transplantation 15(7):804-811 (2009).

Kimbrel, Erin A. et al. Mesenchymal Stem Cell Population Derived From Human Pluripotent Stem Cells Displays Potent Immunomodulatory and Therapeutic Properties. Stem Cells and Development 23(14):1611-1624 (2014).

Kin, Cindy, and M. Kate Bundorf. As Infliximab Use for Ulcerative Colitis Has Increased, So Has the Rate of Surgical Resection. Journal of Gastrointestinal Surgery 21(7):1159-1165 (2017).

Kinnaird, T. et al. Marrow-derived stromal cells express genes encoding a broad spectrum of arteriogenic cytokines and promote in vitro and in vivo arteriogenesis through paracrine mechanisms. Circulation Research 94(5):678-685 (2004).

Klyushnenkova, Elena. et al. T cell responses to allogeneic human mesenchymal stem cells: immunogenicity, tolerance, and suppression. Journal of Biomedical Science 12(1):47-57 (2005).

Kurtzberg, Joanne. et al. Allogeneic Human Mesenchymal Stem Cell Therapy (Remestemcel-I, Prochymal) as a Rescue Agent for Severe Refractory Acute Graft-versus-host Disease in Pediatric Patients. Biology of Blood and Marrow Transplantation 20(2):229-235 (2014).

Lai, Ruenn Chai. et al. Exosome secreted by MSC reduces myocardial ischemia/reperfusion injury. Stem Cell Res 4(3):214-222 (2010).

Lanyu, Zhang, and Hei Feilong. et al. Emerging role of extracellular vesicles in lung injury and inflammation. Biomed Pharmacother 113:108748, 1-9 (2019).

Le Blanc, Katarina. et al. Mesenchymal Stem Cells for Treatment of Steroid-resistant, Severe, Acute Graft-versus-host Disease: a Phase II Study. The Lancet 371(9624):1579-1586 (2008).

Le Blanc, Katarina et al. Treatment of Severe Acute Graft-versus-host Disease With Third Party Haploidentical Mesenchymal Stem Cells. The Lancet 363(9419):1439-1441 (2004).

Lee, Jae W. et al. Concise review: Mesenchymal stem cells for acute lung injury: role of paracrine soluble factors. Stem Cells 29(6):913-919 (2011).

Lee, Jong Lyul. et al. Treatment Strategy for Perianal Fistulas in Crohn Disease Patients: The Surgeon's Point of View. Annals of Coloproctology 37(1):5-15 (2021).

Lee, Ryang Hwa. et al. Intravenous hMSCs Improve Myocardial Infarction in Mice Because Cells Embolized in Lung Are Activated to Secrete the Anti-inflammatory Protein TSG-6. Cell Stem Cell 5(1):54-63 (2009).

Lee, Tanya. et al. Long-term Outcomes of Perianal Fistulizing Crohn's Disease in the Biologic Era. JGH Open 5(2):235-241 (2021).

Lee, Woo Yong. et al. Autologous Adipose Tissue-derived Stem Cells Treatment Demonstrated Favorable and Sustainable Therapeutic Effect for Crohn's Fistula. Stem Cells 31(11):2575-2581 (2013).

Leibacher, Johannes, and Reinhard Henschler. Biodistribution, Migration and Homing of Systemically Applied Mesenchymal Stem/stromal Cells. Stem Cell Research and Therapy 7:1-12 (2016).

Liang, Lu. et al. Human Umbilical Cord Mesenchymal Stem Cells Ameliorate Mice Trinitrobenzene Sulfonic Acid (TNBS)-induced Colitis. Cell Transplantation 20(9):1395-1408 (2011).

Liu et al.: Therapeutic potential of mesenchymal stem/stromal cell-derived secretome and vesicles for lung injury and disease. Expert Op Biol Ther. 29(2):125-140 (2019).

Locatelli, Franco et al. Remestemcel-I for the Treatment of Graft Versus Host Disease. Expert Review of Clinical Immunology 13(1):43-56 (2017).

(56)　　　　　References Cited

OTHER PUBLICATIONS

Logozzi, Mariantonia et al. Microenvironmental pH and Exosome Levels Interplay in Human Cancer Cell Lines of Different Histotypes. Cancers 10(10):370, 1-15 (2018).

Lundberg, Johan. et al. Targeted intra-arterial transplantation of stem cells to the injured CNS is more effective than intravenous administration: engraftment is dependent on cell type and adhesion molecule expression. Cell transplantation 21(1):333-343 (2012).

Mak, Joyce Wing Yan. et al. Stopping Anti-tumour Necrosis Factor Therapy in Patients With Perianal Crohn's Disease. Alimentary Pharmacology & Therapeutics 50(11-12):1195-1203 (2019).

Makela, Tuomas. et al. Safety and biodistribution study of bone marrow-derived mesenchymal stromal cells and mononuclear cells and the impact of the administration route in an intact porcine model. Cytotherapy 17(4):392-402 (2015).

Makowiec, F. et al. Clinical Course of Perianal Fistulas in Crohn's Disease. Gut 37(5):696-701 (1995).

Mannon, Peter J. Remestemcel-I: Human Mesenchymal Stem Cells as an Emerging Therapy for Crohn's Disease. Expert Opinion on Biological Therapy 11(9):1249-1256 (2011).

Marei, Hany E. et al. Potential of stem cell-based therapy for ischemic stroke. Frontiers in neurology 9:271733, 1-7 (2018).

Meisel, Roland. et al. Human Bone Marrow Stromal Cells Inhibit Allogeneic T-cell Responses by Indoleamine 2, 3-dioxygenase-mediated Tryptophan Degradation. Blood 103(12):4619-4621 (2004).

Moghadasali, Reza. et al. Autologous transplantation of mesenchymal stromal cells tends to prevent progress of interstitial fibrosis in a rhesus Macaca mulatta monkey model of chronic kidney disease. Cytotherapy 17(11):1495-1505 (2015).

Molendijk, Ilse. et al. Allogeneic Bone Marrow-Derived Mesenchymal Stromal Cells Promote Healing of Refractory Perianal Fistulas in Patients With Crohn's Disease. Gastroenterology 149(4):918-927. e6 (2015).

Moseley, Tim. MSC Extracellular Vesicles in IBD: A Path to Clinical Translation and Therapeutic Innovation. IBD Innovate: Product Development for Crohn's & Colitis Presentation :1-14 (2025).

Nicola, Massimo Di. et al. Human bone marrow stromal cells suppress T-lymphocyte proliferation induced by cellular or nonspecific mitogenic stimuli. Blood 99:3838-3843 (2002).

Oliveira-Sales, Elizabeth B., and Mirian A. Boim. Mesenchymal stem cells and chronic renal artery stenosis. American Journal of Physiology—Renal Physiology 310(1):F6-F9 (2016).

Otani, Kosuke et al. Plasma exosomes regulate systemic blood pressure in rats. Biochem Biophys Res Commun 503(2):776-783 (2018).

Panes, Julian. et al. Long-term Efficacy and Safety of Stem Cell Therapy (Cx601) for Complex Perianal Fistulas in Patients With Crohn's Disease. Gastroenterology 154(5):1334-1342 (2018).

Panes, Julián. et al. Expanded allogeneic adipose-derived mesenchymal stem cells (Cx601) for complex perianal fistulas in Crohn's disease: a phase 3 randomised, double-blind controlled trial. Lancet 388(10051):1281-1290 (2016).

Parks, A G. et al. A Classification of Fistula-in-ano. British Journal of Surgery 63(1):1-12 (1976).

Patel, Amit N., and Jorge Genovese. Potential Clinical Applications of Adult Human Mesenchymal Stem Cell (Prochymal®) Therapy. Stem Cells and Cloning: Advances and Applications 4:61-72 (2011).

Pezato, Rogerio. et al. Immunoregulatory Effects of Bone Marrow-derived Mesenchymal Stem Cells in the Nasal Polyp Microenvironment. Mediators of Inflammation 2014(1):583409, 1-11 (2014).

Portilla, F de la. et al. Expanded allogeneic adipose-derived stem cells (eASCs) for the treatment of complex perianal fistula in Crohn's disease: results from a multicenter phase I/IIa clinical trial. Int J Colorectal Dis 28(3):313-323 (2013).

Romanov et al.: Comparative Analysis of Secretome of Human Umbilical Cord- and Bone Marrow-Derived Multipotent Mesenchymal Stromal Cells. Cell Technologies in Biology and Medicine. 4:535-540 (2019).

Rutgeerts, Paul. et al. Comparison of scheduled and episodic treatment strategies of infliximab in Crohn's disease. Gastroenterology 126(2):402-413 (2004).

Rutgeerts, Paul. et al. Infliximab for induction and maintenance therapy for ulcerative colitis. N Engl J Med 353(23):2462-2476 (2005).

Rutgeerts, Paul. et al. Infliximab for induction and maintenance therapy for ulcerative colitis. New England Journal of Medicine 353(23):2462-2476 (2005).

Ryan, J. M. et al. Interferon-gamma Does Not Break, but Promotes the Immunosuppressive Capacity of Adult Human Mesenchymal Stem Cells. Clinical and Experimental Immunology 149(2):353-363 (2007).

Saad, Ahmed. et al. Autologous Mesenchymal Stem Cells Increase Cortical Perfusion in Renovascular Disease. Journal of the American Society of Nephrology 28(9):2777-2785 (2017).

Sandborn, William J. et al. Adalimumab induction therapy for Crohn disease previously treated with infliximab: a randomized trial. Ann Intern Med 146(12):829-838 (2007).

Sandborn, William J. et al. Certolizumab Pegol for the Treatment of Crohn's Disease. The New England Journal of Medicine 357(3):228-238 (2007).

Sandborn, William J. et al. Vedolizumab as induction and maintenance therapy for Crohn's disease. N Engl J Med 369(8):711-721 (2013).

Savitz, Sean I. et al. Stem cell therapy as an emerging paradigm for stroke (Steps) II. Stroke 42(3):825-829 (2011).

Schreiber, Stefan. et al. Maintenance therapy with certolizumab pegol for Crohn's disease. New England Journal of Medicine 357(3):239-250 (2007).

Schwartz, David A. et al. The Natural History of Fistulizing Crohn's Disease in Olmsted County, Minnesota. Gastroenterology 122(4):875-880 (2002).

Semont, Alexandra. et al. Mesenchymal Stem Cell Therapy Stimulates Endogenous Host Progenitor Cells to Improve Colonic Epithelial Regeneration. Plos One 8(7):e70170, 1-14 (2013).

Semont, Alexandra. et al. Mesenchymal Stem Cells Increase Self-renewal of Small Intestinal Epithelium and Accelerate Structural Recovery After Radiation Injury. Tissue Engineering 585:19-30 (2006).

Sengupta, Vikram. et al. Exosomes derived from bone marrow mesenchymal stem cells as treatment for severe COVID-19. Stem cells and development 29(12):747-754 (2020).

Shao, Mingyang. et al. Exosomes derived from human umbilical cord mesenchymal stem cells ameliorate IL-6-induced acute liver injury through miR-455-3p. Stem Cell Res Ther 11(1):37, 1-13 (2020).

Shi, Ming. et al. A Pilot Study of Mesenchymal Stem Cell Therapy for Acute Liver Allograft Rejection. Stem Cells Translational Medicine 6(12):2053-2061 (2017).

Sun, Lingyun. et al. Umbilical Cord Mesenchymal Stem Cell Transplantation in Severe and Refractory Systemic Lupus Erythematosus. Arthritis and Rheumatology 62(8):2467-2475 (2010).

Sun, Qipeng. et al. Allogeneic Mesenchymal Stem Cells as Induction Therapy Are Safe and Feasible in Renal Allografts: Pilot Results of a Multicenter Randomized Controlled Trial. Journal of Translational Medicine 16:52, 1-10 (2018).

Sun, Zhongwei. et al. Stem Cell Therapies for Chronic Obstructive Pulmonary Disease: Current Status of Pre-clinical Studies and Clinical Trials. Journal of Thoracic Disease 10(2):1084-1098 (2018).

Tamama, Kenichi, and Svetoslava S Kerpedjieva. Acceleration of Wound Healing by Multiple Growth Factors and Cytokines Secreted from Multipotential Stromal Cells/Mesenchymal Stem Cells. Advances in Wound Care 1(4):177-182 (2012).

Toma, Jean G. et al. Isolation of Multipotent Adult Stem Cells From the Dermis of Mammalian Skin. Nature Cell Biology 3(9):778-784 (2001).

U.S. Appl. No. 17/427,192 Office Action dated Apr. 7, 2025.

U.S. Appl. No. 17/606,514 Office Action dated Mar. 4, 2025.

Van Rijn, Kyra L. et al. Fibrosis and MAGNIFI-CD Activity Index at Magnetic Resonance Imaging to Predict Treatment Outcome in Perianal Fistulizing Crohn's Disease Patients. Journal of Crohn's and Colitis 16(5):708-716 (2022).

(56) References Cited

OTHER PUBLICATIONS

Vulliet, P. Richard. et al. Intra-coronary arterial injection of mesenchymal stromal cells and microinfarction in dogs. The Lancet 363(9411):783-784 (2004).

Walczak, Piotr. et al. Dual-modality monitoring of targeted intraarterial delivery of mesenchymal stem cells after transient ischemia. Stroke 39(5):1569-1574 (2008).

Wang et al. Mesenchymal Stem Cells in the Wharton's Jelly of the Human Umbilical Cord. Stem Cells 22:1330-1337 (2004).

Website: ACS Webinars. https://www.acs.org/content/dam/acsorg/acs-webinars/2023/Slides/2023-03-09-exosomes-cas1.pdf (2023).

Wilson, Jennifer G. et al. Mesenchymal stem (stromal) cells for treatment of ARDS: a phase 1 clinical trial. Lancet Respir Med 3(1):24-32 (2015).

Yamout, Bassem. et al. Bone Marrow Mesenchymal Stem Cell Transplantation in Patients With Multiple Sclerosis: a Pilot Study. Journal of Neuroimmunology 227(1-2):185-189 (2010).

Yoshimura, Kotaro. et al. Characterization of Freshly Isolated and Cultured Cells Derived From the Fatty and Fluid Portions of Liposuction Aspirates. Journal of Cellular Physiology 208(1):64-76 (2006).

Yuan et al.: Current advances in stem cell-based therapies for hari regeneration. E. J. of Pharmacology. 881(173197):1-12 (2020).

Zhu, Ying-gang. et al. Human mesenchymal stem cell microvesicles for treatment of Escherichia coli endotoxin-induced acute lung injury in mice. Stem cells 32(1):116-125 (2014).

ExoFlo Information packet [retrieved from internet on May 30, 2025 URL:https://www.rejuvenate528.com/wp-content/uploads/2020/06/ExoFlo-Packet1.pdf published (2020).

Furuta et al. Mesenchymal Stem Cell-Derived Exosomes Promote Fracture Healing in a Mouse Model. Stem Cells Translational Medicine 5(12):1620-1630 (2016).

Gabrielyan, Anastasia. et al. IL-11 and soluble VCAM-1 are important components of hypoxia conditioned media and crucial for mesenchymal stromal cells attraction. Stem Cell Research 45:101814, 1-11 (2020).

Hildreth, Cade. Direct Biologics Receives FDA Approval to Proceed with Second ExoFlo IND for Post-Acute COVID-19 Syndrome and Chronic Post-COVID-19 Syndrome. Direct BioInformant Blog Jun. 9, 2021. Retrieved Mar. 26, 2025. Retrieved from https://bioinformant.com/direct-biologics-second-exoflo-ind/.

Huang, He. et al. Bone marrow mesenchymal stem cell-derived extracellular vesicles improve the survival of transplanted fat grafts. Mol Med Rep 16(3):3069-3078 (2017).

Hwang, Insik. et al. Neural stem cells and the secreted proteins TIMPs ameliorate UVB-induced skin photodamage. Biochemical and biophysical research communications 518(2):388-395 (2019).

Lee, et al. Hypoxic conditioned medium from mesenchymal stem cells promotes lymphangiogenesis by regulation of mitochondrial-related proteins. Stem Cell Research & Therapy 7:38, 1-11 (2016).

Li et al.: BMSCs-Derived Exosomes Ameliorate Pain Via Abrogation of Aberrant Nerve Invasion in Subchondral Bone in Lumbar Facet Joint Osteoarthritis. Journal of Orthopaedic Research. 38(3):670-679 (2019).

Liao, Zhiqi. et al. Therapeutic Role of Mesenchymal Stem Cell-Derived Extracellular Vesicles in Female Reproductive Diseases. Front Endocrinol (Lausanne) 12:665645, 1-14 (2021).

PCT/US2024/054785 Invitation to Pay Additional Fees with Partial International Search Report dated Feb. 24, 2025.

PCT/US2024/054793 International Search Report and Written Opinion dated Apr. 14, 2025.

PCT/US2024/054793 Invitation to Pay Additional Fees dated Feb. 24, 2025.

PCT/US2024/054794 International Search Report and Written Opinion dated Apr. 14, 2025.

PCT/US2024/054794 Invitation to Pay Additional Fees dated Feb. 24, 2025.

PCT/US2024/054800 International Search Report and Written Opinion dated Apr. 14, 2025.

PCT/US2024/054800 Invitation to Pay Additional Fees dated Feb. 24, 2025.

PCT/US2025/018972 International Search Report and Written Opinion dated Jun. 20, 2025.

PCT/US2025/020723 International Search Report and Written Opinion dated Jun. 20, 2025.

PCT/US2025/026049 International Search Report and Written Opinion dated Jun. 20, 2025.

PCT/US2025/026052 International Search Report and Written Opinion dated Jun. 20, 2025.

Tang, Yaya. et al. Advances in mesenchymal stem cell exosomes: a review. Stem cell Research and therapy 12(1):71, 1-12 (2021).

U.S. Appl. No. 17/420,500 Office Action dated Jun. 4, 2025.

U.S. Appl. No. 17/427,192 Office Action dated Jun. 20, 2025.

U.S. Appl. No. 17/432,138 Office Action dated Jun. 11, 2025.

U.S. Appl. No. 17/606,514 Office Action dated Jun. 25, 2025.

Yang, Yanmeng. et al. Secretive derived from hypoxia preconditioned mesenchymal stem cells promote cartilage regeneration and mitigate joint inflammation via extracellular vesicles. Bioactive Materials 27:98-112 (2023).

Zhu, Ling-Ping. et al. Hypoxia-elicited Mesenchymal Stem Cell-derived Exosomes Facilitates Cardiac Repair Through Mir-125b-mediated Prevention of Cell Death in Myocardial Infarction. Theranostics 8(22):6163-6177 (2018).

* cited by examiner

FIG. 6A                    FIG. 6B

METHOD FOR TREATING OSTEOARTHRITIS WITH MESENCHYMAL STEM CELL EXOSOMES

This is a national phase application filed under 35 U.S.C. § 371 of International Application No. PCT/US2020/017341, filed on Feb. 7, 2020 and entitled "METHOD FOR TREATING OSTEOARTHRITIS WITH A COMBINATION OF MESENCHYMAL STEM CELL EXOSOMES, SYNOVIAL MESENCYMAL STEM CELLS, AND SCAFFOLDS," which claims the benefit of U.S. Provisional Application No. 62/908,853, filed on Oct. 1, 2019 and U.S. Provisional Application No. 62/802,310, filed on Feb. 7, 2019, applications which are incorporated herein by reference in their entirety.

I. BACKGROUND

Osteoarthritis (OA) is a disorder of any join in the body that leads to symptoms such as inflammation, pain, and limited function. It is also the most common chronic illness in the United States. Most arthritis occurs in the knee or hip joint, followed by the ankle and shoulder joint. In addition, arthritis of the fingers and base of the thumb is quite common.

OA is also called wear and tear arthritis, and it is by far the most common cause of arthritis. About a third of adults in the United States over 65 years have arthritis to the point of requiring regular medication. Symptoms include pain in a joint during or after movement, tenderness in the joint when pushed on, a crunching feeling or sound of bone rubbing on bone, and stiffness in the joint after periods of inactivity, such as sleeping or sitting.

The pathogenesis of knee OA have been linked to biomechanical and biochemical changes in the cartilage of the knee joint (e.g., the inability to withstand normal mechanical stresses, limited supply of nutrients and oxygen, inadequate synthesis of extracellular matrix components, increased synthesis of tissue-destructive proteinases, such as matrix metalloproteinases and aggrecanases, and overall apoptosis of chondrocytes). Recently, synovial inflammation has also been accredited as a factor limiting knee cartilage repair. Moreover, it correlates to clinical signs of knee OA, such as swelling of the knee and inflammatory pain. It is believed that synovial inflammation is a response of synovial macrophages to cartilage debris and catabolic mediators entering the synovial cavity.

Articular cartilage is both aneural and avascular. As such, cartilage is incapable of directly generating pain, inflammation, stiffness, or any of the symptoms that patients with OA typically describe. While the above is all known information, the exact causes of pain in OA are not entirely understood.

Therefore, what is needed is a method for restoring articular cartilage to a normal physiologic condition to stop synovial inflammation and, thus, eliminate the pain of OA.

II. SUMMARY

Disclosed are methods and compositions related to mesenchymal stem cell (MSC) exosome compositions for use treating diseases, disorders, and injuries affecting joints.

In one aspect, disclosed herein are methods of treating, inhibiting, reducing, ameliorating and/or preventing a disease, disorder, injury (such as, for example, osteoarthritis, juvenile arthritis, psoriatic arthritis, infectious arthritis, rheumatoid arthritis, ankylosing spondylitis, gout, bursitis, tendinosis, tendonitis, sprain, labral tear, tear of a tendon, and/or tear of a ligament) or symptoms thereof (such as, for example, pain, inflammation, and/or swelling) affecting one or more joints (such as, for example, the ankle, knee, hip, writs, elbow, shoulder, knuckle, and/or neck) in a subject comprising administering to a subject a therapeutically effective amount of a mesenchymal stem cell (MSC) exosome preparation.

Also disclosed herein are methods of any preceding aspect, wherein the MSC exosome preparation is administered to each joint effected by the disorder, disease, or injury.

In one aspect, disclosed herein are methods of any preceding aspect, wherein the MSC exosome preparation further comprises growth factors (such as, for example, prostaglandin E2 (PGE2), transforming growth factor $\beta1$ (TGF-$\beta1$), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-$\alpha$ receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-$\alpha$ (TGF-$\alpha$) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF), and/or hormones including estrogen, and thyroid hormones) obtained from MSC.

Also disclosed herein are methods of any preceding aspect, wherein the MSC exosomes are administered via injection, MSC exosome carrying scaffold, hydrogel, and/or topical cream or salve.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 6A shows a radiograph of the Right Elbow shows Kellgren-Lawrence Grade Three changes of the Radio-ulnar joint and the humeral-ulnar joints.

FIG. 6B shows radiographs of the Left Elbow are Normal.

IV. DETAILED DESCRIPTION

Figure 1:
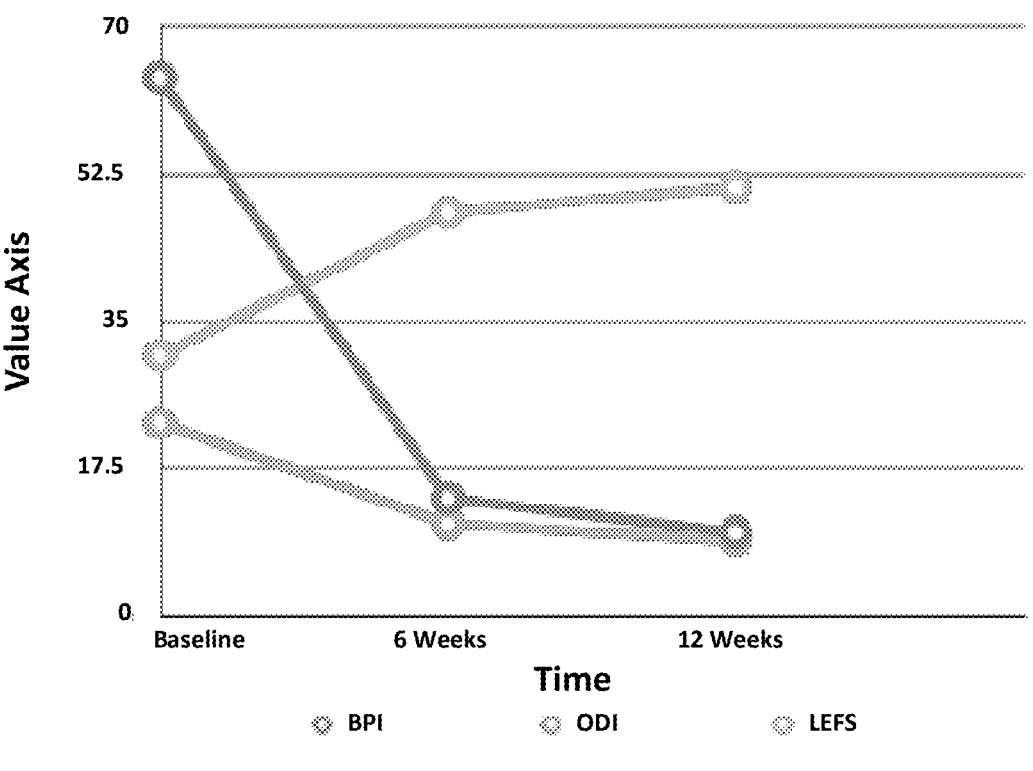
FIG. 1 shows a lower BPI and ODI=improvement, a higher LEFS score=improvement.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "subject" is defined herein to include animals such as mammals, including, but not limited to, primates (e.g., humans), cows, horses, pigs, sheep, goats, dogs, cats, rabbits, rats, mice and the like. In some embodiments, the subject is a human.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intraarticular, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intrasynovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily, or the dose may be proportionally reduced as indicated by the exigencies of the therapeutic situation.

A "decrease" can refer to any change that results in a smaller gene expression, protein production, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease, disorder, injury, or condition, or an underlying cause of a disease or condition. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain (i.e., nociception) relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular MSC exosome (with or without growth factors) referred to herein as an extracellular vesicle isolate product (EVIP) is disclosed and discussed and a number of modifications that can be made to a number of molecules including the EVIP are discussed, specifically contemplated is each and every combination and permutation of EVIP and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. Methods of Treating Osteoarthritis

In contrast to articular cartilage, the synovium and joint capsule are richly innervated and are likely the primary source of the pain in OA. The synovial reaction in OA includes synovial hyperplasia, fibrosis, thickening of the synovial capsule, activated synoviocytes and, in some cases, lymphocytic infiltrate (B- and T-cells, as well as plasma cells). The synovium is of obvious relevance as one of the most densely innervated structures of the joint. Synovial causes of pain include irritation of sensory nerve endings within the synovium from osteophytes and synovial inflammation that is due, at least in part, to the release of prostaglandins, leukotrienes, proteinases, neuropeptides, and cytokines. Pro-inflammatory examples include Interleukins 1, 6, and 8 along with various tumor necrosis factors. A semi-quantitative measure of synovitis from the infrapatellar fat pad is associated with pain severity. Any decrease in synovitis is associated with a decrease in OA pain severity.

Despite the fact that bone marrow is considered a well-accepted source of MSCs, various studies have reported that MSCs can be isolated from various adult mesenchymal tissues, including synovium. Studies have shown that synovium-derived MSCs have great proliferation potential and multilineage differentiation potential in vitro. Studies have also compared human MSCs derived from bone marrow, synovium, periosteum, adipose tissue, and muscle and determined that synovium-derived MSCs have greater expansion and chondrogenic ability in vitro than MSCs from other tissues. This suggests that synovium-derived MSCs are superior as a source for cartilage regeneration.

Studies have shown that synovial MSCs can be detached from the synovium using a brushing technique, resulting in a marked increase in the numbers of synovial MSCs found in the synovial fluid.

In one aspect, disclosed herein are methods of treating, inhibiting, reducing, ameliorating and/or preventing a disease, disorder, injury (such as, for example, osteoarthritis, juvenile arthritis, psoriatic arthritis, infectious arthritis, rheumatoid arthritis, ankylosing spondylitis, gout, bursitis, tendinosis, tendonitis, sprain, labral tear, tear of a tendon, and/or tear of a ligament) or symptoms thereof (such as, for example, pain, inflammation, and/or swelling) affecting one or more joints (such as, for example, the ankle, knee, hip, writs, elbow, shoulder, knuckle, and/or neck) in a subject comprising administering to a subject a therapeutically effective amount of a mesenchymal stem cell (MSC) exosome preparation.

In one aspect, disclosed herein are methods of treating, inhibiting, reducing, ameliorating and/or preventing a disease, disorder, injury (such as, for example, osteoarthritis, juvenile arthritis, psoriatic arthritis, infectious arthritis, rheumatoid arthritis, ankylosing spondylitis, gout, bursitis, tendinosis, tendonitis, sprain, labral tear, tear of a tendon, and/or tear of a ligament) or symptoms thereof (such as, for example, pain, inflammation, and/or swelling) affecting one or more joints (such as, for example, the ankle, knee, hip, writs, elbow, shoulder, knuckle, and/or neck) in a subject, wherein the MSC exosome preparation (also referred to herein as EVIP) further comprises growth factors (such as, for example, prostaglandin E2 (PGE2), transforming growth factor $\beta1$ (TGF-$\beta1$), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-$\alpha$ receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-$\alpha$ (TGF-$\alpha$) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF), and/or hormones including estrogen, and thyroid hormones) obtained from MSC.

It is understood and herein contemplated that the disclosed MSC exosome treatments may not be curative of a disease, disorder, injury, or condition to a joint and may reduce or inhibit the injury, disease, or disorder. In one aspect, the MSC exosome preparation decreases symptoms of a disease, disorder, and/or injury (such as, for example, pain, inflammation, and/or swelling) rather than being curative or repairing the disease, disorder, or injury. Thus, in one aspect, disclosed herein are methods of treating, inhibiting, reducing, preventing and/or ameliorating pain, inflammation, and/or swelling associated with a disease, disorder, and/or injury affecting one or more joints of a subject comprising administering to the subject any of the MSC exosome preparations disclosed herein (in some cases including MSC derived growth factors).

It is understood and herein contemplated that administration can be directly to one or more effected joints. As noted throughout, administration of the disclosed MSC derived exosomes and/or growth factors can be any method know to those of skill in the art. Accordingly, disclosed herein are methods of treating, inhibiting, reducing, ameliorating and/or preventing a disease, disorder, injury (such as, for example, osteoarthritis, juvenile arthritis, psoriatic arthritis, infectious arthritis, rheumatoid arthritis, ankylosing spondylitis, gout, bursitis, tendinosis, tendonitis, sprain, labral tear, tear of a tendon, and/or tear of a ligament) or symptoms thereof (such as, for example, pain, inflammation, and/or swelling) affecting one or more joints (such as, for example, the ankle, knee, hip, writs, elbow, shoulder, knuckle, and/or neck) in a subject comprising administering to a subject a therapeutically effective amount of a mesenchymal stem cell (MSC) exosome preparation, wherein the MSC exosomes are administered via injection, MSC exosome carrying scaffold, hydrogel, and/or topical cream or salve. As the field of tissue engineering progresses, the need for novel scaffold structures and reproducible fabrication techniques has become of paramount importance. The use of biodegradable polymers, such as poly lactic acid (PLA), has become widespread, but the manner in which these polymers are processed, and the additives used at the time of manufacture, allows the final properties of the scaffold to be tailored.

Poly-hydroxyl acids, such as PLA and poly lactic-co-glycolic acid (PLGA), have been extensively used for tissue engineering procedures, as these materials bulk-degrade by hydrolysis, providing a controllable drug release and degradation profile to match tissue in-growth. With careful use of molecular weights, cross links and side chains, materials can be produced with tailor-made properties making them ideal for use in tissue engineering matrices. Furthermore, poly-hydroxyl acid materials also have a long history of in vivo usage as degradable sutures, drug delivery devices and biodegradable surgical components.

Existing scaffold types include high-pressure, $CO_2$ foamed scaffolds, injectable scaffolds, and novel custom scaffolds. These can be further modified using growth factors, zonation of materials, and plasma polymerization deposition. While the scaffold enhances residence of the synovial MSCs into being adjacent to the articular cartilage, this can be augmented by the addition of cytokines. For instance, PLGA with transforming growth factor-β3 enhances MSC differentiation into chondrocytes, while implantation of PLGA with stromal-derived factor-1α (SDF-1α) results in repair of the articular cartilage. Thus, implantation of PLGA combined with various cytokines enhances more efficient differentiation of synovial MSCs into articular cartilage. This technique provides concentrated MSC growth factors and RNA to the synovial MSCs located in the peri-articular scaffold to maximize differentiation into chondrocytes.

By way of example, some embodiments of the invention include a method for treating osteoarthritis, the method comprising a one-step arthroscopic procedure to restore arthritic articular cartilage to a normal physiologic condition. Specifically, the method may comprise detaching synovial mesenchymal stem cells (MSCs) from the synovium using a brush device; covering the articular cartilage with a scaffold; and placing concentrated MSC exosomes into the affected joint, such as the knee joint, to stimulate the differentiation of the synovial MSCs into articular cartilage cells.

In embodiments, the brush may be an arthroscopic brush specifically designed to be used in conjunction with a particular joint.

When the scaffold is placed arthroscopically into the joint, such as the knee, to cover the articular cartilage, the intraarticular floating MSCs may attach to the peri-articular scaffold. Placing the MSC exosomes into the joint may provide growth factors and various RNAs to stimulate the differentiation of the synovial MSCs into chondrocytes. As a result, the damaged arthritic articular cartilage may be restored.

C. Mesenchymal Stem Cells

As noted throughout, the treatment compositions disclosed herein can utilize exosomes and/or growth factors derived from mesenchymal stem cells (MSCs). While existing autogenous and allogeneic MSCs contained within bone marrow, bone marrow concentrate, synovia-derived mesen-chymal stem cells (MSCs), or adipose-derived stromal vascular fraction (SVF) or various post-natal products from umbilical cord, placenta or amnion, expanded MSC cultures are currently being used to treat wounds, orthopedic pathology, and spine pathology; the existing treatments do not contain large amounts of MSC secretomes (including, but not limited to growth factors, cytokines, chemokines, exosomes, extracellular vesicles, and/or extracts). Additionally, despite evidence in the art that treatments comprising stem cells (including injectable treatments) can help prevent aging and treat scarring, uneven pigmentation, existing skin products, such as creams, lotions, serums, make-up, and the like, while including ingredients that potentially help treat and strengthen the skin, other topical products do not penetrate the epidermis and more importantly do not include human MSCs, or MSC-derived growth factors and proteins. In fact, prior to the present disclosure an active MSC growth factor product that can be used for these applications has not been developed. Thus, in one aspect, disclosed herein are MSC secretome compositions (including, but not limited to MSC growth factor, MSC exosome, MSC extracts and/or extracellular vesicle comprising compositions) for use in the treatment of wounds, orthopedic disorders, orthopedic injuries, ophthalmology, spinal injury, or spinal disorders, said treatment compositions comprising (i) a growth factor powdered additive comprising a mesenchymal stem cell (MSC) derived preparation and (ii) a pharmaceutically acceptable carrier.

As noted above, MSC are multipotent cells that have the ability to differentiate into a multitude of cell types including myocytes, chondrocytes, adipocytes, and osteoblasts. Typically, these cells can be found in the placenta, umbilical cord blood, adipose tissue, bone marrow, or amniotic fluid, including perivascular tissue. As used herein, "MSC" refers to non-terminally differentiated cells including but not limited to multipotential stem cell, multipotential stromal cell, stromal vascular cells, pericytes, perivascular cells, stromal cells, pluripotent cells, multipotent cells, adipose-derived fibroblast-like cells, adipose-derived stromal vascular fraction, adipose-derived MSC, bone marrow-derived fibroblast-like cells, bone marrow-derived stromal vascular fraction, bone marrow-derived MSC, tissue-derived fibroblast-like cells, adult stem cells, adult stromal cells, keratinocytes, and/or melanocytes.

It has been long recognized that MSC, in addition to their differentiation potential, have the immunomodulatory abilities resulting in the expression of many different cytokines and growth factors. As used herein, a "MSC preparation" or "MSC secretome composition" refers to a composition comprising MSC growth factors, MSC exosomes, extracellular vesicles, or acellular extracts of MSCs or MSC lysates obtained from human MSCs, fibroblast-like cells, and non-human animal MSCs including, but not limited to MSCs from horses, cows, pigs, sheep, non-human primates, dogs, cats, rabbits, rats, and mice. In embodiments, the MSCs may be derived from the patient to which the composition will be applied (autologous) or derived from another individual (allogeneic). The MSCs may be culture expanded to collect the conditioned media or to increase the quantity of cells for the lysate or used freshly prior to incorporation into the composition of the present disclosure.

The MSC secretome compositions (including, but not limited to MSC growth factor, MSC exosome, MSC extracts and/or extracellular vesicle comprising compositions) may comprise about 0.00001 to about 20 wt. %, such as from about 0.01 to about 10 wt. %, of a mesenchymal stem cell (MSC) extract, MSC exosome, or MSC growth factor preparation. The MSC preparation may comprise either MSC conditioned media or MSC lysate from cell culture expanded MSCs. In some embodiments, the composition may further comprise from about 0.01 to about 10 wt. % of a cell-free medium conditioned by growth of MSCs or MSC lineage cells, wherein the cells are cultured under normal hyperoxyic culturing conditions or under artificial wound healing conditions.

As disclosed herein the MSCs used to produce the disclosed MSC additives (including growth factor secretome composition either frozen or powdered additives) can be selectively stimulated to produce MSC growth factors, secretomes, cytokines, chemokines, mesenchymal stem cell proteins, peptides, glycosaminoglycans, extracellular matrix (ECM), proteoglycans, secretomes, and exosomes. As used herein, MSC growth factors include but are not limited to prostaglandin E2 (PGE2), transforming growth factor $\beta1$ (TGF-$\beta1$), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-$\alpha$ receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-$\alpha$ (TGF-$\alpha$) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF), as well as hormones including estrogen, and thyroid hormones.

In one aspect, the MSC preparation (such as, for example, a MSC secretome composition) comprises MSC growth factors, MSC exosomes, and/or cellular extracts of MSCs or MSC lysates obtained from MSCs cultured under standard hyperoxyic culturing conditions (for example, 21% oxygen) or MSCs cultured under artificial wound healing conditions (such as, for example, 0.1% to about 5% oxygen in the presence of inflammatory cytokines, angiogenic factors, and reduced glucose).

As disclosed herein artificial wound healing conditions simulate growth conditions in real wounds where there is a reduction in nutrient supply and reduction of waste removal that is usually caused by a disruption in local blood circulation. This creates a harsh environment for cells until new blood vessels are created and blood circulation is restored. Accordingly, artificial wound healing conditions used to culture MSCs can include one or more of the following growth conditions reduction in glucose availability, reduction in oxygen tension, reduction in pH, and increased temperature.

In one aspect, the glucose availability can be reduced relative to normal control. Modified culture media to reduce glucose, but not damage the cells can be between 0 and 50% reduction in glucose, more preferably between about 5% and 40% reduction in glucose. For example, MSC artificial wound healing culture conditions can comprise glucose reduction of about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% such as a glucose reduction from about 5% to about 15%, from about 10% to about 20%, from about 15% to about 25%, from about 20% to about 30%, or from about 25% to about 35%.

In one aspect, oxygen tension can be reduced to oxygen levels to hypoxic conditions. Normal atmospheric oxygen is approximately 21% and any reduction is considered hypoxic. Thus, in one aspect, MSCs can be cultured at between 0.0% and 20.9% oxygen, from about 0.1% to about 0.5% oxygen, from about 0.1% to about 2.0%, from about 0.1% to about 5.0% oxygen, from about 0.5% to 5.0%, from about 1.0% to about 10% oxygen, about 5.0% to about 10.0% oxygen; and from about 10.0% to about 15.0% under artificial wound healing conditions. Preferably during MSC would healing culture conditions oxygen tension is between about 0.5% and 20.5% oxygen, such as, for example, 0, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.7, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, or 20.5% oxygen.

The pH can also be reduced under artificial wound healing conditions. Physiologic pH is maintained very tightly and is usually very close to a neutral pH=7.2±0.2 (7.0-7.4). However, in a wound the acidic environment can have a pH=6.2±0.2 (i.e., a pH from 6.0 to about 6.4). Thus, under artificial wound healing culture conditions, pH can be from about 6.0 to about 7.4, for example, from 6.0 to about 6.4, from about 6.2 to about 6.4, from about 6.2 to about 6.6, from about 6.4 to about 6.6, from about 6.4 to about 6.8, or from about 6.6 to about 7.0, such as 6.0, 6.1, 6.2, 6.3, 6.4, 6.5, 6.6, 6.7, 6.8, 6.9, 7.0, 7.1, 7.2, 7.3 or 7.4.

Under artificial wound healing culture conditions, the temperature of the culture environment may be raised to simulate temperature increases at the site of a wound. Physiologic homeostasis temperature is maintained at 37° C. (98.6° F.). A slight increase or decrease can cause significant changes to cellular metabolism. By increasing the temperature above 37° C. to any temperature up to about 40° C. (104° F.) can create an "feverous" environment. Thus, in on aspect, the artificial wound healing culture conditions for the MSCs can comprise from about 35° C. to about 39° C., from about 35° C. to about 36° C., from about 36° C. to about 37° C., from about 37° C. to about 38° C., from about 38° C. to about 39° C., from about 39° C. to about 40° C. In one aspect, the temperature of the artificial wound healing culture can be 35.0, 35.1, 35.2, 35.3, 36.4, 35.5, 35.6, 35.7, 35.8, 35.9, 36.0, 36.1, 36.2, 36.3, 36.4, 36.5, 36.6, 36.7, 36.8, 36.9, 37.0, 37.1, 37.2, 37.3, 37.4, 37.5, 37.6, 37.7, 37.8, 37.9, 38.0, 38.1, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, or 40.0° C.

In one aspect, the MSC secretome compositions (including, but not limited to MSC growth factor, MSC exosome, MSC extracts and/or extracellular vesicle comprising compositions) can further comprise a protective coating (such as, for example, a cryoprotectant oligosaccharide and a protein solution) to reduce degradation of the growth factors. It is understood and herein contemplated that the protective coating can be engineered as a polymer. "Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer.

It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc. In one aspect, the gel matrix can comprise copolymers, block copolymers, diblock copolymers, and/or triblock copolymers.

In one aspect, the protective coating can comprise a biocompatible polymer. In one aspect, biocompatible polymer can be crosslinked. Such polymers can also serve to slowly release the adipose browning agent and/or fat modulating agent into tissue. As used herein biocompatible polymers include, but are not limited to polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), polyhydroxyacids such as poly(lactic acid), poly (gly colic acid), and poly (lactic acid-co-glycolic acid); polyhydroxyalkanoates such as poly3-hydroxybutyrate or poly4-hydroxybutyrate; poly-caprolactones; poly(orthoesters); polyanhydrides; poly (phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof. Biocompatible polymers can also include polyamides, polycarbonates, polyalkylenes, polyalkylene glycols, polyalkylene oxides, polyalkylene terepthalates, polyvinyl alcohols (PVA), methacrylate PVA (m-PVA), polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly (ortho esters), poly(ethylene amines), poly(caprolactones), poly(hydroxybutyrates), poly(hydroxyvalerates), polyanhydrides, poly(acrylic acids), polyglycolides, poly(urethanes), polycarbonates, polyphosphate esters, polyphospliazenes, derivatives thereof, linear and branched copolymers and block copolymers thereof, and blends thereof.

In some embodiments the protective coating comprises carbohydrate construction of monosaccharides as well as carbohydrate polymers such as disaccharides or polysaccharides including but not limited to non-reducing poly or disaccharides as well as any combination thereof. Examples of carbohydrates that can be used in the protective coating comprise Glucose, Aldoses (D-Allose, D-Altrose, D-Mannose, etc.), Glucopyranose, Pentahydroxyhexanal, α-D-Glucopyranosyl-D-glucose, α-D-Glucopyranosyl-dihydrate, Polymer of β-D-Glycopyranosyl units, β-D-Fructofuranosyl α-D-glucopyranoside (anhydrous/dihydrate), β-D-Galactopyranosyl-D-glucose, α-D-Glucopyranosyl-α-D-glucopyranoside (anhydrous/dihydrate), Galactose, Pentoses (Ribose, xylose, lyxose), Dextrose, Dodecacarbon monodecahydrate, Fructose, Sucrose, Lactose, Maltose, Trehalose, Agarose, D-galactosyl-β-(1-4)-anhydro-L-galactosyl, Cellulose, Polymer of β-D-Glycopyranosyl units, and Starch, as well as, Polyhydric alcohols, Polyalcohols, Alditols, Erythritol, Glycitols, Glycerol, Xylitol, and Sorbitol.

In some embodiments the protective coating contains biocompatible and/or biodegradable polyesters or polyanhydrides such as poly(lactic acid), poly(glycolic acid), and poly(lactic-co-glycolic acid). The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide5 collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. In one aspect, the polymer comprises at least 60, 65, 70, 75, 80, 85, 89, 90, 91, 92, 93, 94, 95, 96, 97, 98, or 99 percent acetal pendant groups.

The triblock copolymers disclosed herein comprise a core polymer such as, example, polyethylene glycol (PEG), polyvinyl acetate, polyvinyl alcohol, polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like.

Examples of diblock copolymers that can be used in the protective coatings disclosed herein comprise a polymer such as, example, polyethylene glycol (PEG), polyvinyl acetate, polyvinyl alcohol (PVA), polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA).

In one aspect, the protective coating contains (i.e., the encapsulated, the encapsulated compositions can further comprise lecithin or hydrolyzed lecithin as a carrier or as encapsulation material. As used herein, lecithin and/or hydrolyzed lecithin coatings include coatings comprising phosphatidyl choline, phosphatidyl inositol, phosphatidyl ethanolamine, phosphatidylserine, and phosphatidic acid. Sources of the lecithin can be pnat or animal sources.

In one aspect, any of the polymers, monosaccharides, disaccharides, or polysaccharides used to form the protective coating formed by placing the MSC additive in a encapsulating solution can be at an appropriate concentration for form the protective coating. For example, polymers, monosaccharides, disaccharides, or polysaccharides can be at any concentration between 0.01 mM and 10.0M concentration, for example, from about 0.01M to about 0.1M, from about 0.1 mM to about 1.0M, from about 1.0M to about 10.0M. Exemplary concentrations include 0.01, 0.02, 0.03, 0.04, 0.05, 0.06, 0.07, 0.08, 0.09, 0.1, 0.2, 0.3, 0.4, 0.4, 0.6, 0.7, 0.8, 0.9, 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, 325, 350, 375, 400, 450, 500, 600, 700, 800, 900 mM, 1, 1.1, 1.2, 1.3, 1.4, 1.5, 1.6, 1.7, 1.8, 1.9, 2, 3, 4, 5, 6, 7, 8, 9, 10M.

Figure 2:
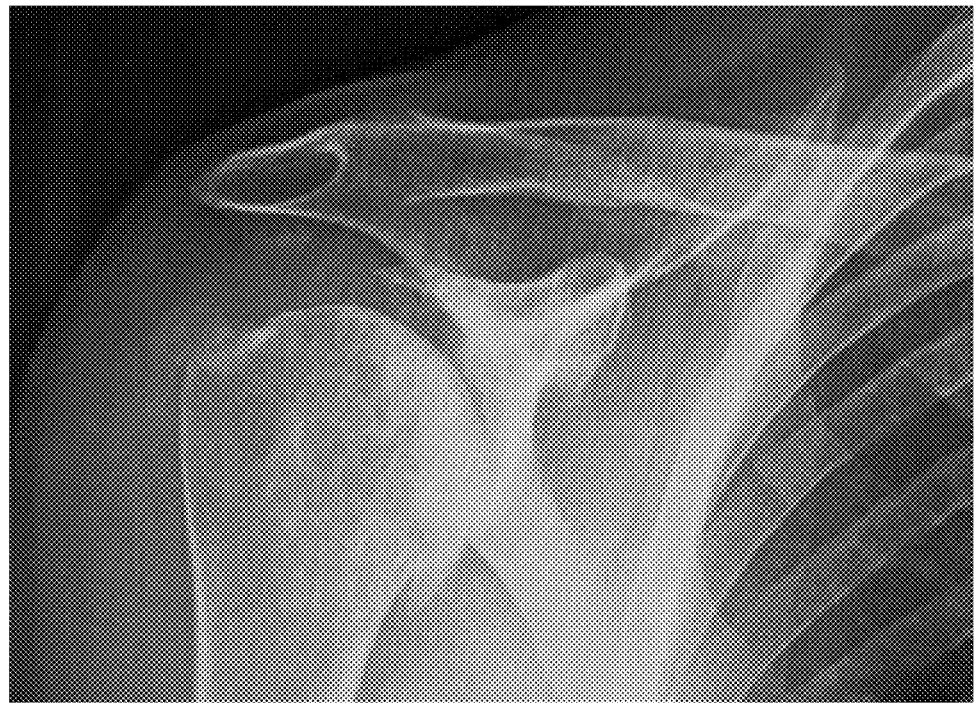
FIG. 2 shows Pre-procedure radiograph of shoulder showing Kellgren-Lawrence grade four osteoarthritis of the gleno-humeral joint.

As shown in FIGS. 1 and 2, the exosomses and extracellular vesicles in the disclosed MSC secretome compositions have been produced.

In one aspect, it is understood and herein contemplated that one way to treat a wound is through administration of the MSC secretome compositions (including, but not limited to MSC growth factor, MSC exosome, MSC extracts and/or extracellular vesicle comprising compositions) subcutaneously, intramuscularly, intravenously, topically (such as, for example, through the use of salves, creams, and/or ointments), but also by impregnating stents, sponges, matrixes, scaffolds, bandages, dressing, sutures, grafts, surgical drapes, surgical adhesive, and/or staples with the MSC secretome compositions. Thus, in one aspect, disclosed herein are medicated stents, scaffolds, sponges, matrixes, adhesive bandages, wound dressings, grafts, surgical drapes, sutures, salves, creams, or wound adhesives comprising a therapeutically effective amount of the MSC secretome composition. The MSC secretome compositions (including, but not limited to MSC growth factor, MSC exosome, MSC extracts and/or extracellular vesicle comprising compositions), as noted above, can be administered topically and applied to the face, the neck, the hands, or any other desired part of the body. When applied to an adhesive bandage, wound dressing, grafts, surgical drape, suture, scaffold, matrix, sponge, or stent, the MSC secretome composition can be a applied as a powder.

In one aspect, the MSC secretome compositions (including, but not limited to MSC growth factor, MSC exosome, MSC extracts and/or extracellular vesicle comprising compositions) disclosed herein may comprise any known ingredients typically found in the wound healing fields, such as oils, waxes or other standard fatty substances, or conventional gelling agents and/or thickeners; emulsifiers; moisturizing agents; emollients; sunscreens; hydrophilic or lipophilic active agents, such as ceramides; agents for combating free radicals; bactericides; sequestering agents; preservatives; basifying or acidifying agents; fragrances; surfactants; fillers; natural products or extracts of natural product, such as aloe or green tea extract; vitamins; or coloring materials. Other ingredients that may be combined with the powder may include an antioxidant, which can be selected from a variety of antioxidants. Suitable antioxidants include vitamins, such as Vitamin C (L-Ascorbate, Ascorbate-2 Phosphate magnesium salt, Ascorbyl Palmitate, Tetrahexyldecyl Ascorbate), Vitamin E (Tocotrienol), Vitamin A (retinol, retinal, retinoic acid, provitamin A carotenoids, such as beta-carotene), N-acetyl glucosamine, or other derivatives of glucosamine Other ingredients may include at least one essential fatty acid, such as $\Omega$-3, $\Omega$-6, and $\Omega$-9 polyunsaturated fatty acids, such as linoleic acid (LA), gamma-linoleic acid (GLA), alpha-linoleic acid (ALA), dihomo-y-linolenic acid (DGLA), arachidonic acid (ARA), and others. The fatty acids may be derived from various sources including evening primrose oil, black currant oil, borage oil, or GLA modified safflower seeds. Other ingredients may include a platelet rich fibrin matrix, at least one ingredient to support ECM production and production of hyaluronic acid, such as N-acetyl glucosamine or other derivatives of glucosamine, ultra-low molecular weight (ULMW) hyaluronic acid, chondroitin sulfate, or keratin sulfate.

It is understood and herein contemplated that the MSC secretome compositions disclosed herein can provide wound healing rejuvenation, augmentation, and improved or restored skin tissue. The composition may also be used as an injectable in the treatment of joint arthritis and degenerated spinal discs. Moreover, embodiments of the composition may not require the inclusion of additional growth factors or hormones, such as insulin, insulin-like growth factors, thyroid hormones, fibroblast growth factors, estrogen, retinoic acid, and the like. In some aspect, the disclosed stem cell growth factor compositions can comprise additional active ingredients including, but not limited to antibiotics, anti-acne agents, liposomes, antioxidants, platelet-rich fibrin matrixes, analgesic, anti-inflammatories, as well as, additional growth factors, such as insulin, insulin-like growth factors, thyroid hormones, fibroblast growth factors, estrogen, retinoic acid, and the like. Such additional active ingredients can be mixed with the stem cell growth factor and extracellular vesicle compositions disclosed herein as well as MSC conditioned media, MSC lystates, and MSC-derived produces and then thawed or dissolved, mixed, or suspended in a mixture of emulsifying lanolin alcohols, waxes, and oils or a mixture of petrolatum or mineral oil, a quaternary ammonium compound, a fatty alcohol, and a fatty ester emollient, or lotions that are substantially similar in composition.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Intra-Articular Injection of an Extracellular Vesicle Isolate Product to Treat Hip Labral Tears Diarthrodial joints, such as the knee, hip, and shoulder consist of articular cartilage, a synovial capsule, and a fibrocartilaginous structure to increase the stability of the joint. The knee has both a medial and lateral meniscus. The patient's shoulder and hip each have a labrum which increases the concavity of the glenoid and acetabulum. These fibrocartilaginous structures all have a nerve supply and when torn, can be very painful. These structures have a limited blood supply and when damaged, have minimal capacity to heal. These structures can tear with an acute injury or by a chronic degenerative process. The acetabular labrum creates a fibrocartilaginous seal around the osseous acetabulum. The labrum increases the depth, surface area, volume, congruity, and stability of the hip joint. The labrum has been shown to increase by an average of 22% to the articulating surface area of the hip joint. The labrum lowers the stress on the articular cartilage by regulating fluid transport between the central and peripheral compartments and by distributing contact pressure across the articulating surfaces. This fluid seal is one of the most important function of the labrum, as it produces a negative intra-articular pressure, significantly increasing joint stability.

If the shape of the femoral head and acetabulum do not perfectly match, femoral-acetabular impingement can occur. This is a genetic condition that predisposes the hip labrum to traumatic injury. Hip labral tears are associated with certain activities such as gymnastics, running, jumping, tennis, soccer, and cycling. The diagnosis is suspected when hip ROM, especially forced flexion with internal rotation duplicates the groin pain the patient typically experiences. The diagnosis is confirmed with MRI scanning.

There is a paucity of non-operative treatments for hip labral tears. The most common and effective solution includes decreasing or avoiding activities that causes pain. Physical therapy has shown little efficacy. Surgical options are typically performed arthroscopically. The surgical options include either repairing the labral tear or, more commonly, resecting the torn labrum. Krych, et al, reported the results of hip arthroscopic treatment for labral tears. They reported 59 patients, the mean age was 46, and the mean follow up was 5 years. They reported a clinical failure rate of 45% due to repeat surgery in 20% and continued pain in 25%.

Published reports of using injections of autogenous bone marrow concentrate (BMC) with mesenchymal stem cells (MSC) to treat shoulder labral tears indicate safety and efficacy. The MSC is the only cell that can differentiate into a chondroblast, osteoblast, or fibroblast. It has historically been thought differentiation was the mechanism by which MSC injections treated joint pathology. It has become increasingly recognized the efficacy of using MSC injections to treat various conditions is due to their paracrine function of releasing anti-inflammatory growth factors (GF) and exosomes. These GFs and exosomes can be injected without any living cells. This case report will introduce the concept of using acellular bone marrow-derived MSC GFs and exosomes to treat hip labral tears. This is described as an extracellular vesicle isolate product (EVIP). The paper will discuss the rationale of why acellular will replace all current cellular biologic therapies, both autogenous and allogeneic for the treatment of various joint pathologies.

a) Materials and Methods

This is a case report of an EVIP injection for the treatment of a hip labral tear. A hip labral tear is characterized by a locking, clicking, or catching in the hip joint. Pain is felt in the groin or radiating into the trochanteric area. Patients complain of stiffness or limited hip range of motion. MRI scanning is used to diagnose a labral tear of the hip joint. The patient is a 50-year old, extremely active triathlete, personal trainer, and health instructor. Following several months of untreated groin pain, she presented on Jun. 11, 2019 with an increasing right groin and buttocks pain radiating into the upper leg. Her symptoms were exacerbated with activities requiring hip ROM. MRI scanning of the hip joint on Jun. 4, 2019 revealed a superior labrum tear, superior anterior labral fraying, tear of the gluteus minimus tendon, trochanteric bursal inflammation, and common hamstring tendinosis. The hip joint did not have osteoarthritis. She had been treated with NSAIDs, weekly active release, and chiropractic treatments. On physical examination she had an overall 20% loss of hip ROM. Forced internally rotation and flexion replicated and severely exacerbated her pain. The patient felt overall her right hip was less than 50% normal compared to the opposite hip. The patient was evaluated with a Brief Pain Inventory (BPI), a Lower Extremity Functional Index (LEFI), and an Oswestry Disability Index (ODI) prior to the injection and at follow-up.

(1) The Hip Injection

After counseling and consent, the patient on Jun. 11, 2019 underwent the hip injection. The right groin and buttocks area were sterilized with a betadine skin prep. A 20-gauge needle was placed through an anterior approach into the hip joint. Needle placement was verified by fluoroscopy. At this point, 2 cc of the frozen EVIP (ExoFlo-Direct Biologics, St. Louis MO) was thawed to room temperature and placed into the joint.

b) Clinical Results

The patient was put on restricted physical activity for 1 week following the procedure. Passive low-resistance range of motion was encouraged immediately. The patient returned to full activities at 10 days. Six weeks post-procedure, she was able in one day to run 7 miles, kayak 2 hours and swim 600 yards. She was able to sleep like a "rock" and wake up with no pain. The patient opines she has experienced an overall 75% improvement from her preprocedure hiplabral tear symptoms.

(1) Follow Up MRI Scan

A follow-up gadolinium arthrogram MRI scan of the right hip was performed on Aug. 28, 2019. The scan showed NO discrete labral tear. There was no evidence of tendinosis or interstitial tearing of the gluteus minimums tendon. There was no trochanteric bursal inflammation. The impression was a negative MRI of the right hip joint. Her clinical results from pre-procedure to 12-week FU are shown in both (FIG. 1) and (Table 1). They detail the improvement noted in her Brief Pain Inventory (a lower score is better), Oswestry Disability Index (a lower score is better), and her Lower Extremity Functional Score (a higher score is better).

TABLE 1

| Physical evaluation measurements with the percent improvement over the initial 12 weeks. | | | | |
| --- | --- | --- | --- | --- |
| | Baseline | 6 Weeks | 12 Weeks | Percent Improvement |
| BPI | 64 | 14 | 10 | 84% |
| ODI | 23 | 11 | 9 | 61% |
| LEFS | 31 | 48 | 51 | 61% | c) Discussion

The patient is an active 50 YO triathlete with a history of increasing pain from a documented hip labral tear. She underwent a single anterior hip injection of 2 cc of bone marrow-derived mesenchymal stem cell EVIP (ExoFlo-Direct Biologics, St. Louis MO) containing active growth factors and exosomes. Two weeks later, her labral tear symptoms were improved by 75%. This improvement has been maintained through three months. Her pre-injection arthrogram MRI documents a superior labrum tear, superior anterior labral fraying, tear of the gluteus minimus tendon, trochanteric bursal inflammation, and common hamstring tendinosis. The hip joint did not have osteoarthritis. Her post-injection arthrogram MRI documents no evidence of a labral tear. There was no evidence of tendinosis or interstitial tearing of the gluteus minimus tendon. There was no trochanteric bursal inflammation. The impression was a negative MRI of the right hip joint. She will continue to be closely monitored for two years.

The non-operative treatment for symptomatic labral tears is basically to avoid activities that cause pain. The surgical options are either arthroscopic removal or repair of the labrum. Published results indicate a 45% failure rate with arthroscopic hip labral surgery.

Based on understanding the biology of labral tears, non-operative treatment will be an injection of acellular MSC derived growth factors and especially exosomes. The exosome is a tiny 30 to 150 nanometer-sized (1 billionth of a meter) bi-phospholipid membrane-enclosed structure created by the endosomes. An MSC (12 to 18 microns) is 1,000 times larger than an exosome. The diameter of a hair is 80,000 nanometers. Exosomes contain growth factors, signaling lipids and micro, and messenger RNA. These paracrine factors can be placed into any joint in concentrations of 100,000 or more times that of any cellular MSC treatment. These growth factor proteins and exosomes function in a paracrine fashion to both, directly and indirectly, alter the inflammatory environment of a painful labral tear back to a normal non-painful physiologic environment and stimulate fibrocartilaginous healing.

The future acellular treatment for labral tears will involve a two-step process: first, highly concentrated anti-inflammatory bone marrow-derived MSC growth factors and exosomes are injected into the painful joint. Second, these growth factors and exosomes enter the recipient synovial MSCs to stimulate the production of new chondroblasts and anti-inflammatory secretomes, chemokines, and cytokines. These effects have been shown to heal fibrocartilaginous tears. This acellular biologic treatment can all be achieved with a single joint injection. The future of regenerative medicine in orthopedics and spine may well be the utilization of highly concentrated acellular MSC derived growth factors and especially exosomes.

Example 2: Intra-Articular Injection of an Extracellular Vesicle Isolate to Treat Shoulder Osteoarthritis in an Athlete Shoulder osteoarthritis (OA) has been demonstrated in cadaver and radiographic studies to affect up to 33% of patients over the age of 60. Patients that present with shoulder OA have pain, crepitus, loss of motion and decreased ability to place their hand at a desired point in space. Limiting the ability to place your hand where you desire severely impairs activities of daily living. The non-surgical treatments for shoulder OA, in an attempt to maintain range of motion, include shoulder exercises, the use of analgesics and non-steroidal anti-inflammatory medications. If these non-surgical treatments fail to relieve the OA impairment, then the default surgical treatment is total shoulder arthroplasty (TSA).

Recently it has become increasingly understood by researchers and physicians that the clinical efficacy of utilizing mesenchymal stem cells (MSCs) to treat osteoarthritis (OA). Additionally, it is becoming evident that the relief is not dependent on the cells differentiating into articular cartilage but entirely on their paracrine release of growth factors (GFs) and exosomes, with the cells possibly interfering with the healing process. Active growth factors and exosomes can function without the cells when delivered into an arthritic joint. This is a case report of an acellular MSC derived Extracellular Vesicle Isolate Product (EVIP) injection for the treatment of shoulder osteoarthritis. Shoulder OA is defined by pain and stiffness in the shoulder joint, worsened by exercise and decreased shoulder range of motion. This case report will introduce the concept of using EVIP containing active growth factors and exosomes to treat OA and the rationale of why acellular biologic treatments could replace current autogenous and allogeneic cellular biologic therapies.

a) Methods

The patient, a 57-year-old male athlete that is right hand dominant, presented with a greater than 14-year history of increasing bilateral shoulder pain right-side much worse than left side. Pre-procedure radiographs and MRI scanning were used to distinguish osteoarthritis of the glenohumeral joint from rotator cuff abnormalities. A previous MRI scan of the shoulder obtained on Jan. 5, 2006 (13 years before this procedure) revealed a Kellgren-Lawrence score of 4, which is bone-on-bone osteoarthritis of the glenohumeral joint.

The patient was further evaluated at each visit with a Physical examination of the shoulder and using QuickDASH (QD), a measure of shoulder function with lower scores being ideal; The Upper Extremity Functional Index (UEFI) with higher percentages being better scores; Brief Pain Inventory (BPI) with higher scores indicate higher pain, as well as a patient self-rated evaluation of overall shoulder improvement. These physical evaluation procedures were performed at three different clinic visits: Pre-procedure, and then at six weeks and twelve weeks post-procedure. On initial physical examination, there was observed an average 75% loss of internal, external and abduction of the right glenohumeral joint. All range of motion evaluations were associated with severe pain, crepitus and bone on bone clunking. Pre-procedural radiograph of the shoulder is shown in FIG. 2.

(1) Shoulder Injection

After counseling and consent the patient's right shoulder was prepared with betadine skin solution. A 20-gauge needle was placed through an anterior approach into the glenohumeral joint. The needle was placed against the humoral head within the shoulder joint capsule. Needle placement was verified by internal and external rotation of the humeral head causing the needle to move. A 2.0 cc preparation of the frozen EVIP (*ExoFlo—Direct Biologics*, St. Louis, MO) was thawed to room temperature and placed into the glenohumeral joint.

The patient was placed on restricted physical activity for 1 week following the procedure. Passive low-resistance range of motion was encouraged immediately. Two weeks after the procedure the patient returned to full activities.

b) Results

Figure 3:
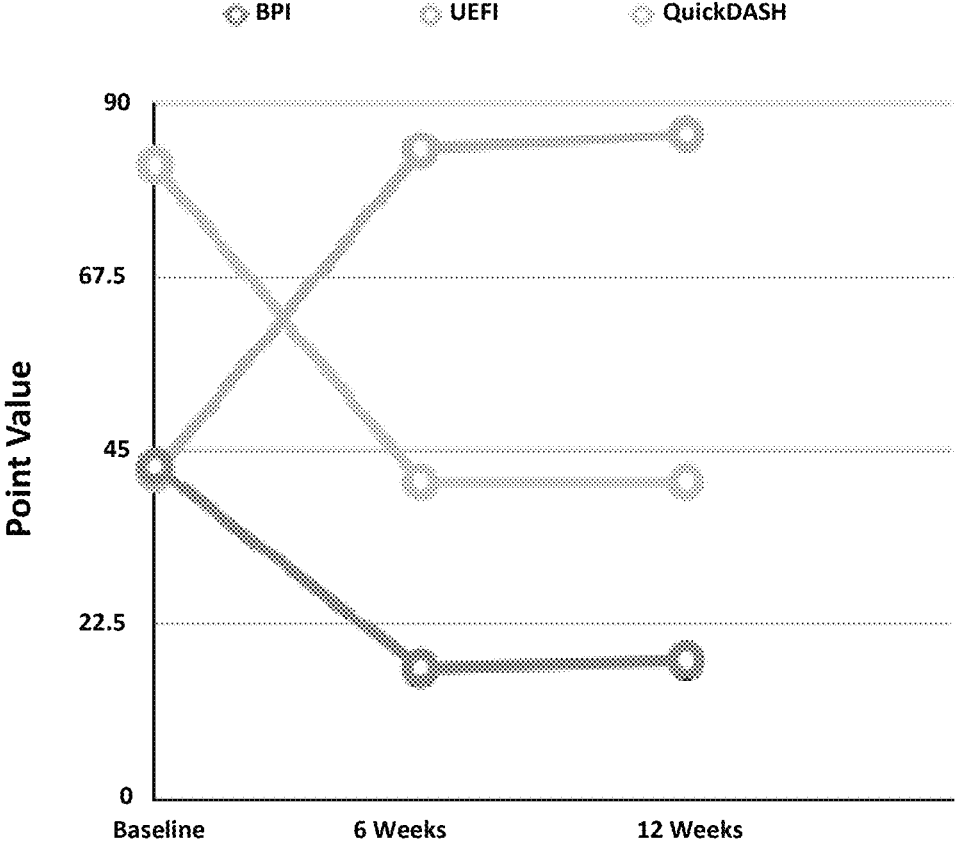
FIG. 3 shows A lower BPI and QuickDash=improvement, A higher UFEI score=improvement.

The patient's self-rated overall shoulder improvement was 75% from 2 weeks after the injection to the 12-week evaluation. The QuickDASH, The Upper Extremity Functional Index, and Brief Pain Inventory were all improved within 2 weeks and that improvement was maintained out to 12 weeks as shown in the graph in FIG. 3 and the values displayed in Table 2.

TABLE 2

Physical evaluation measurements with the percent
improvement over the initial 12 weeks.

| | Baseline | 6 Weeks | 12 Weeks | Percent Improvement |
|---|---|---|---|---|
| BPI | 43 | 17 | 18 | 58% |
| UEFI | 42 | 84 | 86 | 51% |
| QuickDASH | 82 | 41 | 41 | 50% |

Overall shoulder improvement was self-rated to be 75%. Post-procedure glenohumeral range of motion improved by 33% based on physical examination.

c) Discussion

The patient is a male 57-year-old active athlete that presented with a greater than 14-year history of increasing right dominant shoulder pain. He was diagnosed with Kellgren-Lawrence grade four bone on bone glenohumeral osteoarthritis without rotator cuff abnormalities. It is not anticipated to observe regeneration of the articular cartilage. Follow up x-rays will not change. He underwent a single injection of 2 cc of a bone marrow derived EVIP containing active growth factors and exosomes. The injection was performed without complications. Within two weeks the patient was 50% improved or more based on the BPI, UEFI and QD measurement scales. He rated his shoulder to overall be 75% improved. He had returned to full activities by two weeks. These results have been maintained out to 12 weeks. The patient will continue to be monitored at later timepoints. The pain relief observed is felt to be due to the decrease in inflammation of the synovial capsule.

Figure 4:
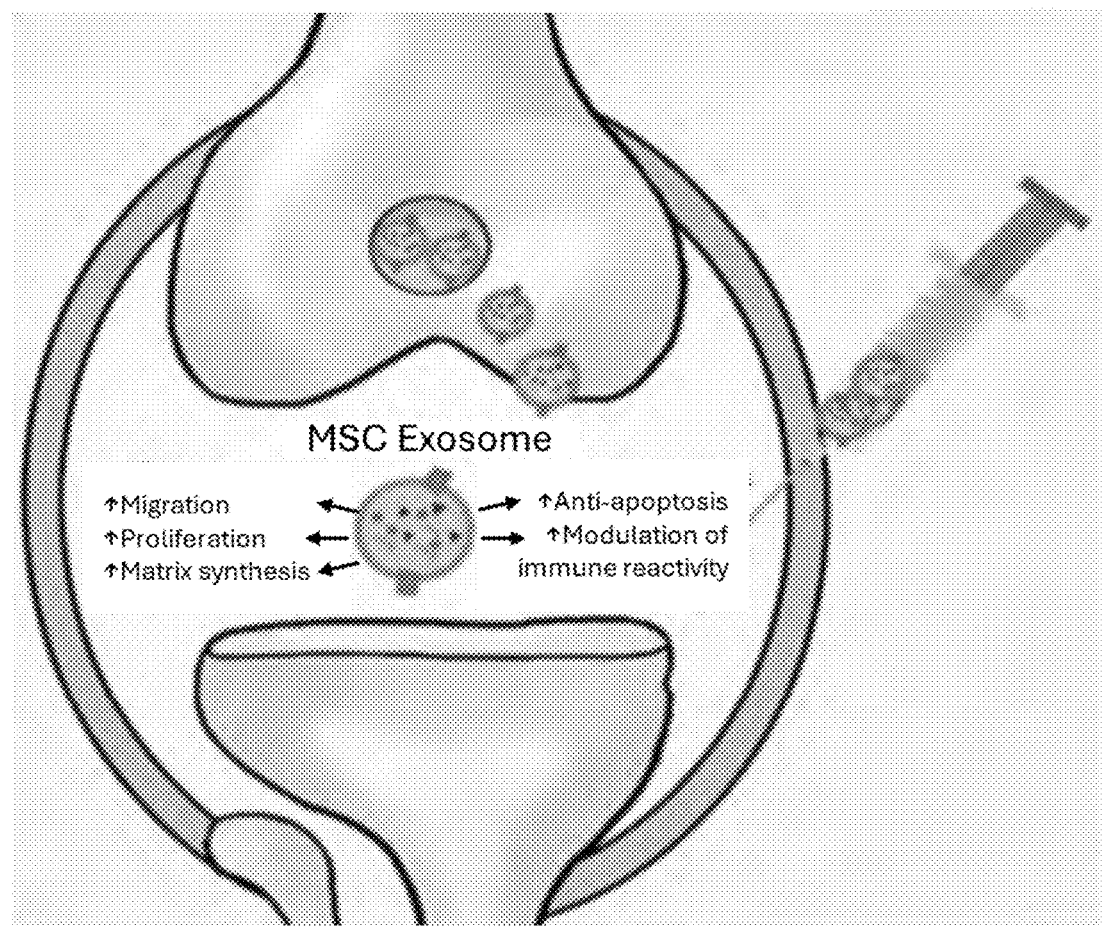
FIG. 4 shows a diagram of the MSC exosome treatment for OA.

The shoulder is a di-arthrodial joint with a synovial lining and a joint capsule. The synovial capsule contains numerous synovial MSCs (more than found in bone marrow or adipose). These MSCs have more chondrogenic potential than bone or adipose MSCs. During the development of OA, pro-inflammatory and catabolic growth factors are produced by these synovial MSCs. This creates a chronically inflamed painful and degenerative joint environment. Bone marrow concentrate (BMC) contains on average only about 2,500 MSCs per cc. Despite the incredibly small number of MSCs found in BMC; there is extensive literature reporting clinical efficacy in the use of BMC for the treatment of OA. This effect cannot be dependent upon BMC/MSC cell survival or differentiation. The efficacious effect must be from the release of acellular paracrine factors. The future of the biologic treatment of OA will be the utilization of acellular MSC derived growth factors and especially exosomes. The exosome is a tiny 30 to 150 nanometersized (1 billionth of a meter) bi-phospholipid membrane enclosed structure created inside the cell's cytoplasm. An MSC (12 to 30 microns) is ~1,000 times larger than an exosome. For reference, the diameter of a hair is 80,000 nanometers or 80 microns. Exosomes contain growth factors, signaling lipids and micro, and messenger RNA (miRNA and mRNA). The RNA contents in exosomes mediate most of their anti-inflammatory effects. The RNA is packaged into an exosome along with numerous growth factors naturally by the cell. These cell-derived paracrine factors can be placed into any joint in concentrations of 100,000 or more times that of any cellular MSC treatment and function in a paracrine fashion to, directly and indirectly, alter the inflammatory environment of any painful arthritic joint back to a normal non-painful homeostatic physiologic environment. FIG. 4 illustrates this process.

The future acellular treatment for OA will involve a two-front attack. First, highly concentrated anti-inflammatory MSC derived growth factors are injected into the arthritic joint. These growth factors will enter the nucleus of the recipient synovial MSC. The EVIP growth factors will stimulate transcription of mRNA containing cellular instructions to produce continuous anti-inflammatory and regenerative secretomes, chemokines, and cytokines. These are released from the recipient cells into the synovial fluid. Second, the highly concentrated exosomes from the EVIP will enter recipient cells to deliver their mRNA and miRNA. This delivered mRNA will directly undergo translation in the recipient synovial MSC ribosomes to produce an anti-inflammatory and regenerative secretome (growth factors, cytokines, chemokines and extracellular vesicles). These salubrious effects could last months or years. This acellular biologic treatment can all be achieved with a single arthritic joint injection and avoids the morbidity and cost of obtaining autogenous MSCs. The future of regenerative medicine in orthopedics and spine may well be the utilization of highly concentrated acellular MSC bone marrow derived growth factors and especially exosomes.

3. Example 3: Intra-Articular Injection of an Extracellular Vesicle Isolate Product to Treat Hip Osteoarthritis Hip osteoarthritis (OA) has demonstrated, in both cadaver and radiographic studies, to affect up to 55 million patients over the age of 60. Patients with hip OA have pain, crepitus, loss of motion, and decreased ability to weight bear or ambulate. Limiting the ability to ambulate severely impairs activities of daily living. The nonsurgical treatments forhip OA according to the American Academy of Orthopedic Surgeons (AAOS), include weight loss, gentle exercise, and the use of non-steroidal anti-inflammatory medications. The surgical treatment forhip OA is total hip arthroplasty (THA). The AAOS does not recommend hip arthroscopy or the use of any Hyaluronic Acid injections.

Over the last few years, it has become increasingly understood by researchers and clinicians that the clinical efficacy of utilizing mesenchymal stem cells (MSCs) to treat osteoarthritis (OA) is not dependent on the cells differentiating into articular cartilage but entirely on their paracrine release of growth factors (GFs) and exosomes. Living MSCs are not required to accomplish the release of GFs and exosomes into an arthritic joint. This case report will introduce the concept of using an acellular MSC derived extracellular vesicle isolate product (EVIP) containing active growth factors and exosomes to treat hipOAas well as the rationale of why acellular may replace all current cellular biologic therapies both autogenous and allogeneic presently in use.

a) Materials and Methods

This is a case report of an EVIP injection for the treatment of hip osteoarthritis. OA is defined by swelling, pain, and stiffness in the hip joint. Symptoms are typically worsened by weightbearing and ambulation. Radiographs and MRI scanning were used to grade osteoarthritis of the hip joint from one to four using the Kellgen-Lawrence scale.

The patient is a 63-year-old retired Chicago Fireman. He presented with increasing pain in the left groin and a progressive loss of ability to continue his daily health club fitness routine. He experienced a progressive loss of hip mobility. MRI scanning and radiographs of the left hip joint were compatible with Kellgren-Lawrence Grade 3 osteoarthritic changes of the left hip joint. On physical examination, he had an antalgic limp and a positive Trendelenburg sign. Passive ROM of the hip joint was associated with the reproduction of severe groin pain, crepitus, and a loss of internal rotation. The patient had a BMI of 27. NSAIDs had failed to provide adequate pain relief. The patient was seriously considering total hip arthroplasty. In an attempt to avoid surgery, he elected to have an injection of an EVIP containing active GFs and exosomes into his hip.

Figure 5:
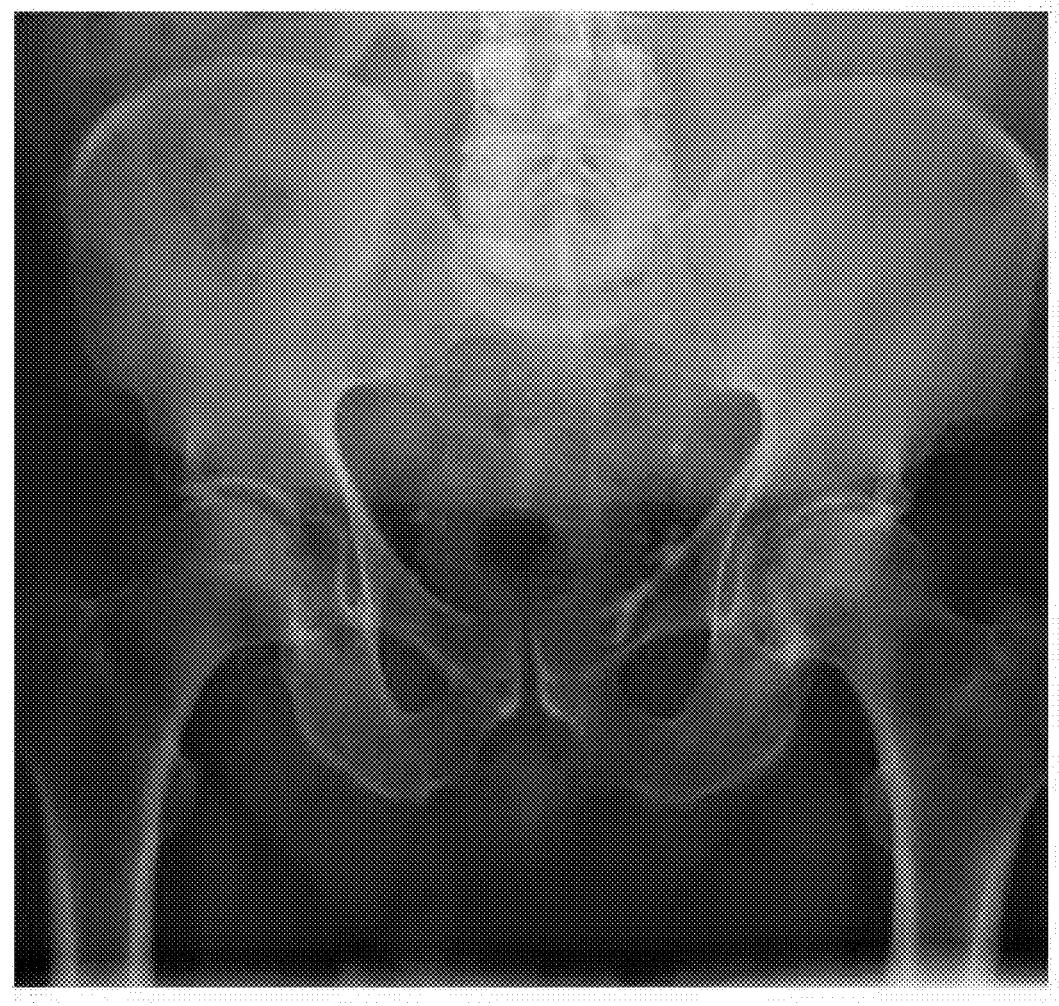
FIG. 5 shows a radiographs of a pelvis.

Radiographs of a pelvis are shown in FIG. 5. This x-ray shows a normal right hip and grade three OA hip on the left. The left hip was sterilized with betadine skin prep. A 20-gauge spinal needle was placed through an anterolateral approach into the hip joint. Needle placement was verified by fluoroscopy. At this point, 2 cc of the frozen EVIP (ExoFlo-Direct Biologics, St. Louis MO) was thawed to room temperature and placed into the joint. The patient was put on restricted physical activity for one week following the procedure. Passive low-resistance range of motion was encouraged immediately. The patient returned to full activities at two weeks.

Clinical Results

At the three-month follow-up, the patient had returned to his previous fitness routine without limitation. He is no longer limited in his exercise profile and has enjoyed the return of a functional pain-free hip ROM. He has returned to full activities without restrictions.

b) Discussion

The hip is a di-arthrodial joint with a synovial lining and a joint capsule. The synovial capsule contains numerous synovial MSCs (more than those found in bone marrow or adipose tissue). These MSCs have more chondrogenic potential than bone or adipose MSCs. During the development of OA, proinflammatory growth factors are produced by these synovial MSCs. This creates a chronically inflamed painful joint environment. Bone marrow concentrate (BMC) contains on average only about 2,500 MSCs per cc. Despite the incredibly small number of MSCs found in BMC; there is an extensive amount of literature reporting the clinical efficacy in animals and humans using BMC for the treatment of OA. This effect cannot be dependent upon BMC/MSC cell survival or differentiation. This efficaciousness must be from the release of acellular paracrine factors. The future of the biologic treatment of OA will be the utilization of acellular MSC derived growth factors and especially exosomes.

The exosome is a tiny 30 to 150 nanometer-sized (1 billionth of a meter) bi-phospholipid membrane-enclosed structure created by the Golgi body or apparatus. An MSC (12 to 18 microns) is 1,000 times larger than an exosome. The diameter of a hair is 80,000 nanometers. Exosomes contain growth factors, signaling lipids, and micro and messengerRNA. The RNA contents within exosomes mediate most of their anti-inflammatory effects. The RNA is placed into an exosome along with numerous peptide growth factors. These paracrine factors can be placed into any joint in concentrations of 100,000 or more times that of any cellular MSC treatment. These growth factor proteins and exosomes will function in a paracrine fashion to both directly and indirectly, alter the inflammatory environment of any painful arthritic joint back to a normal non-painful physiologic environment.

The future acellular treatment for OA will involve a two-front attack. First, highly concentrated anti-inflammatory MSC derived growth factors are injected into an arthritic joint. These growth factors will enter the nucleus of the recipient synovial MSC. The EVIP growth factors will stimulate transcription of mRNA containing instructions for the production of continuous anti-inflammatory secretomes, chemokines, and cytokines. These will be released from the recipient synovial MSC into the synovial fluid. Second, the highly concentrated exosomes from the EVIP will enter recipient synovial MSCs to deliver their mRNA. This mRNA will undergo direct translation in the recipient synovial MSC ribosomes to produce anti-inflammatory secretomes, cytokines, and chemokines.

These salubrious effects could last months or years. This acellular biologic treatment can all be achieved with a single arthritic joint injection, without requiring the morbidity and cost of obtaining autogenous MSCs. The future of regenerative medicine in orthopedics and spine may well be the utilization of highly concentrated acellular MSC derived growth factors and especially exosomes.

4. Example 4: Treatment of Elbow Arthritis with an Extracellular Vesicle Isolate Intra-Articular Injection Primary osteoarthritis (OA) of the elbow is an uncommon condition associated with a genetic predisposition. This occurs predominantly within the ulno-humeral joint of the dominant extremity of patients who engage in heavy sport or labor. Posttraumatic elbow OA is by far more common. A variety of traumatic insults may ultimately result in specific forms of posttraumatic OA to the elbow. The most common complaints of patients with either primary or posttraumatic arthritis of the elbow are pain and/or loss of motion. Loss of extension and pronation can be compensated more easily than loss of flexion and supination.

Nonoperative management remains the mainstay of initial treatment for elbow OA. This typically includes elbow sleeves, nonsteroidal anti-inflammatory medications, and intra-articular corticosteroid injections. Avoidance of aggressive terminal flexion and extension activities can result in substantial relief of pain (weight-lifting, boxing, etc.). A course of supervised rehabilitation by a certified therapist is reserved typically for patients presenting with an acute-on-chronic presentation of symptoms with an associated effusion and limitations in motion.

Surgical management is indicated for patients with severe elbow pain or significant loss of mobility with resultant impairment of upper extremity function and limitation with daily activities. Advances in elbow arthroscopy have resulted in favorable outcomes and have totally replaced any open surgical debridement. Arthroscopic debridement of the elbow, particularly in a younger patient population, has reasonable results with improvements in pain and range of motion. It is important to note the published procedures are performed by surgeons with substantial experience with safe, meticulous techniques in elbow arthroscopy. Total elbow arthroplasty is most appropriate for the low-demand, elderly patient (>60-year-old) with inflammatory, posttraumatic, or primary elbow arthritis. Total elbow arthroplasty is rarely applied in the setting of elbow OA in a younger and typically male population.

There is a huge void between non-operative and operative treatment of elbow OA. This is a case report of a young very active Chiropractor with OA of the elbow. She was treated with a single intra-articular injection of a bone marrow derived mesenchymal stem cell (MSC) extracellular vesicle isolate containing active growth factors and exosomes.

a) Materials and Methods:

The patient is a very active healthy 60-year old practicing Chiropractor. She initially injured her dominant right elbow at the age of 16 in a severe water-skiing accident. She suffered a complete dislocation of the elbow with her ulna and radius located posterior to the humerus. There was no neurovascular injury. The elbow was reduced under general anesthesia. After recovery she lacked 15° of full extension and 10° of full flexion. There was no reduction in supination or pronation. She suffered a second injury at the age of 58 resulting in a complete radial head dislocation. Following this injury, she developed traumatic arthritis of the radial capitellum joint with daily pain and joint swelling exacerbated with activities. Her ability to practice chiropractic care was severely limited. She regularly took NSAIDs and ice therapy after work. Her physical examination of the elbow revealed a 15° loss of elbow extension and 10° loss of flexion. She had a 10° loss of pronation and supination. There was one plus swelling of the elbow joint. Her radiographs reveal grade three Kellgren-Lawrence osteoarthritis of the elbow joint (FIGS. 6A and 6B).

(1) Elbow Injection:

After counseling and consent, the patient on Jun. 11, 2019 underwent an elbow injection. The right elbow joint area was sterilized with a betadine skin prep. A 20-gauge needle was placed through a lateral and medial approach into the elbow joint. At this point 3 cc of the frozen EVIP (ExoFlo-Direct Biologics, St. Louis MO) was thawed to room temperature and placed into the medial and lateral side of the elbow joint. The patient experienced no adverse reactions. The entire procedure took 15 minutes.

b) Results

Figure 7:
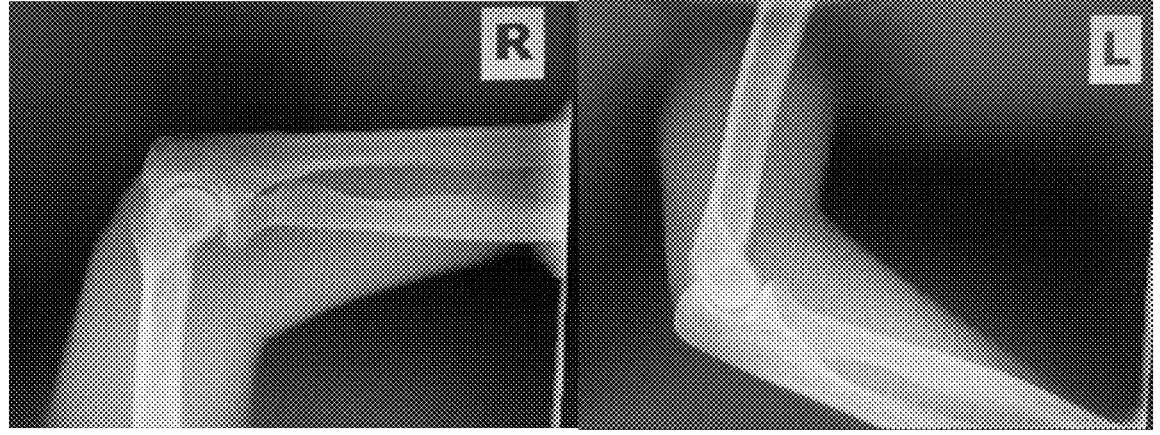
FIG. 7 shows range of motion in the elbow following EVIP administration.

Following the injection, the elbow joint became painful and swollen for several days. She was unable to work for a week. Her symptoms improved over the next 4 weeks. By 6 weeks post injection she felt her elbow was 50% better. This improvement has continued through 3 months and the elbow is now 70% improved from pre-injection. Elbow range of motion has not changed following the EVIP injection (Table 3 and FIG. 7).

TABLE 3

|  | Pre-injection | 6 Weeks | 3 months | Percent Improvement |
|---|---|---|---|---|
| ODI | 26 | 12 | 6 | 77% |
| UEFS | 24 | 42 | 54 | 56% |
| BPI | 22 | 14 | 8 | 64% | c) Discussion

This is a case study of a 60-year old active practicing chiropractor with a many year history of an increasingly symptomatic traumatic osteoarthritic dominant elbow. She suffered a severe posterior elbow dislocation at the age of 16. Her symptoms were greatly exacerbated by work to the point she was considering retirement. This was a major decision because she was in a solo practice with financial overhead. Her surgical option was total elbow arthroplasty. She would be unable to return to her chiropractic practice following this surgical procedure. The goal of the surgery was to attempt to improve her activities of daily living not a return to strenuous work. In an attempt to avoid surgery and continue to practice chiropractic she elected to try an elbow injection of the bone marrow derived MSC EVIP containing active growth factors and exosomes (ExoFlo-Direct Biologics, St. Louis MO). Three months following the injection her elbow is 70% improved and she is working full time.

The elbow is a di-arthrodial joint with a synovial lining and a joint capsule. The synovial capsule contains numerous synovial MSCs (more than found in bone marrow or adipose). These MSCs have more chondrogenic potential than bone or adipose MSCs. During the development of OA, pro-inflammatory growth factors are produced by these synovial MSCs. This creates a chronically inflamed painful joint environment. Bone marrow concentrate (BMC) contains on average only about 2,500 MSCs per cc. Despite the incredibly small number of MSCs found in BMC; there is extensive literature reporting clinical efficacy in animals and humans using BMC for the treatment of OA. This effect cannot be dependent upon BMC/MSC cell survival or differentiation. The efficacious effect must be from the release of acellular paracrine factors. The future of the biologic treatment of OA will be the utilization of acellular MSC derived growth factors and especially exosomes. The exosome is a tiny 30 to 150 nanometer-sized (1 billionth of a meter) bi-phospholipid membrane-enclosed structure created by the Golgi body or apparatus. An MSC (12 to 18 microns) is 1,000 times larger than an exosome. The diameter of a hair is 80,000 nanometers. Exosomes contain growth factors, signaling lipids and micro, and messenger RNA. The RNA contents in exosomes mediate most of their anti-inflammatory effects. The RNA is placed into an exosome along with numerous peptide growth factors. These paracrine factors can be placed into any joint in concentrations of 100,000 or more times that of any cellular MSC treatment. These growth factor proteins and exosomes will function in a paracrine fashion to, directly and indirectly, alter the inflammatory environment of any painful arthritic joint back to a normal non-painful physiologic environment.

The future acellular treatment for OA will involve a two-front attack. First, highly concentrated anti-inflammatory MSC derived growth factors are injected into the arthritic joint. These growth factors will enter the nucleus of the recipient synovial MSC. The EVIP growth factors will stimulate transcription of mRNA containing instructions for the production of continuous anti-inflammatory secretomes, chemokines, and cytokines. These will be released from the recipient synovial MSC into the synovial fluid. Second, the highly concentrated exosomes from the EVIP will enter recipient synovial MSCs to deliver their mRNA. This delivered mRNA will directly undergo translation in the recipient synovial MSC ribosomes to produce anti-inflammatory secretomes, cytokines, and chemokines. These salubrious effects could last months or years. This acellular biologic treatment can all be achieved with a single arthritic joint injection, not requiring the morbidity and cost of obtaining autogenous MSCs. The future of regenerative medicine in orthopedics and spine may well be the utilization of highly concentrated acellular MSC bone marrow derived growth factors and especially exosomes.

5. Example 5: Osteoarthritis Treatment by EVIP Administration

Extracellular Vesicle Isolate Product (EVIP) derived from bone marrow mesenchymal stem cells contains active Growth Factors (over 800) and Exosomes (over 10 Billion per cc). This is the first IRB sponsored report on the safety and efficacy of an EVIP injection to treat OA. Thirty-three former Navy Seals were injected with the EVIP for knee (n=58), shoulder (n=32), elbow (n=16), hip (n=12), ankle (n=8) or wrist (n=6) OA. At three-month follow-up, the average knee patient improved 70% in Brief Pain Inventory (BPI), 67% in Oswestry Disability Index (ODI) and 62% in Lower Extremity Functional Scale (LEFS), the average shoulder patient improved 68% in BPI, 82% in ODI, 74% in QD and 68% in UEFS, the average elbow patient improved 76% in BPI 81% in QD and 76% in UEFS, the average hip patient improved 70% in BPI, 72% in ODI and 64% in LEFS, the average ankle patient improved 70% in BPI, 72% in ODI and 64% in LEFS, and the average wrist patient improved 68% in BPI, 64% in QD and 74% in UEFS. All improvements were to a p<0.001. There were no complications and no patient was made worse from the EVIP injection. At 3-month follow-up the EVIP injection for OA appears safe and efficacious and should be considered prior to joint replacement.

a) EVIP Characterization:

The product is derived from the bone marrow of a 22 year-old female donor whose MSCs have been master banked and registered with the FDA. The end product from these cells contains over 800 different active growth factors and well over 30 billion exosomes per cc. The product is used in a frozen form. Sterilization is achieved through ultrafiltration, not radiation. Acellular exosomes, derived from bone marrow MSCs, provide a consistent product with extensive characterization which includes advanced particle analysis, proteomic evaluation, and USP<71> sterility assurance. Cytokine and growth factor identification and quantification are also performed. Think of acellular exosomes as a therapeutic quality product that is consistent, standardized, and quality tested regarding dose and activity.

(1) Patient Demographics:

The number of patients undergoing treatment for knee, shoulder, elbow, hip, ankle and wrist along with average BMI and average age are shown in Table 4.

Injection Technique: All the injected joints were sterilized with betadine skin prep. Under fluoroscopy a 20-gauge needle was placed into the arthritic joint. Needle placement was verified under fluoroscopic control. At this point, 2 cc of the frozen EVIP (ExoFlo-Direct Biologics, St. Louis MO) was thawed to room temperature and placed into the joint. The entire procedure of injecting four joints per patient required 30 minutes on average.

Patients were not prescribed any pain medications. They were put on a restricted physical activity for 2 weeks following the procedure. Passive low-resistance range of motion was encouraged immediately. After two weeks, patients were allowed to return to full activity.

(2) Statistical Tests

Univariable data comparisons were analyzed by two-tailed Student's t-test with a 95% confidence interval ($\alpha$=0.05. Microsoft Excel). Multivariable data were evaluated by analysis of variance (ANOVA) using JMP 9 statistical analysis software (SAS Institute, Cary NC).

b) Results

Every patient was contacted 12 hours, 24 hours, 48 hours and at 2 weeks, 6 weeks and 3 months to discuss any and all side effects from the EVIP injection. There were no adverse-affects reported by any patient from the EVIP injection. No patient was made clinically worse from the EVIP injection.

TABLE 4

| Description of Patient Demographics | | | |
|---|---|---|---|
| | Shoulder | Hip | Knee |
| Number of patients | 32 | 12 | 58 |

BMI=Average 28.5, Range=23-35
Average age=48.8 years, Range=36-70
Knee=58, Shoulder=32, Elbow=16, Hips=12, Ankles=8, Wrist=6, Total number of joints injected=132

E. REFERENCES

Ball C M, Meunier M, Galatz L M, Calfee R, Yamaguchi K. Arthroscopic treatment of posttraumatic elbow contracture. *Journal of Shoulder and Elbow Surgery.* 2002; 11(6):624-629

Beitzel K, Solovyova O, Cote M P, Apostolakos J, Russell R P, McCarthy M B, et al. The future Role of Mesenchymal Stem Cells in the Management of shoulder Disorders. Arthroscopy. 2013; 29(10):1702-11.

Biswas D, Wysocki R W, Cohen M S: Primary and Secondary Arthritis of the Elbow. Arthritis. 2013, May 27

Black L L, Gaynor J, Adams C, Dhupa S, Sams A E, Taylor R, et al. Effect of intraarticular injection of autologous adipose-derived mesenchymal stem and regenerative cells on clinical signs of chronic osteoarthritis of the elbow joint in dogs. Vet Ther. 2008; 9:192-200.

Black L L, Gaynor J, Gahring D, et al. Effect of adipose-derived mesenchymal stem and regenerative cells on lameness in dogs with chronic osteoarthritis of the coxofemoral joints: a randomized, double-blinded, multicenter, controlled trial. *Vet Ther* 2007; 8:272-84.

Caplan A I, Correa D. The MSC: An injury drugstore. Cell Stem Cell. 2011 Jul. 8; 9(1):11-5.

Caplan A I, Dennis J E. Mesenchymal stem cells as trophic mediators. J Cell Biochem 2006; 98:1076-1084.

Centers for Disease Control and Prevention (CDC) Prevalence and most common causes of disability among adults—United States, 2005. *Morbidity and Mortality Weekly Report* 2009; 58(16):421-426.

Chang C H, Huo T F, Lin F H, et al. Tissue engineering based cartilage repair with mesenchymal stem cells in a porcine model. *J Orthop Res* 2011; 29:1874-80.

Chang Y, Wu K, Ham H. Exosomes and Stem Cells in Degenerative Disease Diagnosis and Therapy. Cell Transplantation, Apr. 25, 2018

Cheng L, Zhang K, Wu S, Cui M, Xu T. Focus on Mesenchymal Stem Cell-Derived Exosomes: opportunities and Challenges in Cell-Free Therapy. Stem Cells Int. 2017; 2017:6305295.

Chew E, Prakash R, Khan W, Mesenchymal Stem Cells in Human Meniscal Regeneration: A Systemic Review. Ann Med Surg. 2017; 24:3-7

Dwyer M K 1, Jones H L, Hogan M G, Field R E, McCarthy J C, Noble P C. The acetabular labrum regulates fluid circulation of the hip joint during functional activities. Am J Sports Med. 2014; 42(4):812-9.

Fan J., Varshney R R, Ren L., Wang D A. Synovium-Derived Mesenchymal stem cells: A new source for musculoskeletal regeneration. *Tissue Engineering Part B Review* 2009 March; 15(1):75-86.

Feng G et al. Transplantation of mesenchymal stem cells and nucleus pulposus cells in a degenerative disc model in rabbits: a comparison of 2 cell types as potential candidates for disc regeneration. *J Neurosurgery Spine* 2011; 14:322-9.

Freitag J, Bates D. Mesenchymal stem cell therapy in the treatment of Osteoarthritis: reparative pathways, safety, and efficacy: A Review. BMC Musculoskeletal Disorders. 2016; 17:230.

Frisbie D D, Smith R K W (2010) Clinical update on the use of mesenchymal stem cells in equine orthopaedics. *Equine Veterinary Journal,* 42:86-9.

Guerico A, Di Marco P, Casella S, et al. Production of canine mesenchymal stem cells from adipose tissue and their application in dogs with chronic osteoarthritis of the humeroradial joints. *Cell Biol Int* 2012; 36:189-94.

Harris J D. Hip labral repair: options and outcomes. Curr Rev Musculoskelet Med. 2016; 9(4):361-367.

Hiyama A, Mochida J, Iwashina T, Omi H, Watanabe T, Serigano K, Tamura F, Sakai D. Transplantation of mesenchymal stem cells in a canine disc degeneration model. J Orthop Res 2008; 26:589-600.

Kellgren J, Lawrence J. Radiological assessment of Osteo-Arthrosis. Ann Rheum Dis December 1957; 16(4):494-502.

Kelly E W, Bryce R, Coghlan J, Bell S. Arthroscopic debridement without radial head excision of the osteoarthritic elbow. Arthroscopy. 2007; 23(2):151-156.

Koga H., Muneta T., et al. Synovial Stem cells are Regionally Specified According to Local Microenvironments after Implantation for Cartilage Regeneration. Stem Cells 2007: 25: 689-96.

Krych A J, Kuzma S A, Kovachevich R, Hudgens J L, Levy B A. Modest Mid-term outcomes after Isolated Arthroscopic Debridement of Acetabular Tears. Knee Surg Sports Traumatol Arthrosc. 2014; 22(4):763-7.

Lee K B, Hui J H, Song I C, et al. Injectable mesenchymal stem cell therapy for large cartilage defects—a porcine model. Stem Cells 2007; 25:2964-71.

Li Z, Wang Y, Xiao K, Weng X. Emerging Role of Exosomes in the Joint Diseases. Cell Physiol Biochem. 2018; 47(5): 2008-2017.

Little C P, Graham A J, Carr A J. Total elbow arthroplasty: a systematic review of the literature in the English language until the end of 2003. Journal of Bone and Joint Surgery. 2005; 87(4):437-444

Mokbel A, El-Tookhy O, Shamaa A A, et al. Homing and efficacy of intra-articular injection of autologous mesenchymal stem cells in experimental chondral defects in dogs. Clin Exp Rheumatol 2011; 29:275-84.

Murphy J M, Fink D J, Hunziker E B, et al. Stem cell therapy in a caprine model of osteoarthritis. Arthritis Rheum 2003; 48:3464-74.

Nguyen D, Proper S I W, MacDermid J C, King G J W, Faber K J. Functional outcomes of arthroscopic capsular release of the elbow. Arthroscopy. 2006; 22(8):842-849.

Pettine K A, Murphy M B, Suzuki R K, Sand T T (2015) Percutaneous injection of Autologous bone marrow concentrate significantly reduces lumbar discogenic pain through twelve months. Stem Cells 33:146-56.

Pettine K P, Dordevic M. The Biologic Treatment of Osteoarthritis with Mesenchymal Stem Cell Exosomes: The Future is now. J Stem Cell Res Dev Ther. 2019; 1-5.

Pettine K P, Dordevic M. TibialMetaphyseal Injection with Bone Marrow Concentrate to Treat Knee Arthritis. American J Stem Cell Res Ther. 2018; 2(1):5-10

Pettine K P, Suzuki R. Autogenous Bone Marrow Concentrate for the treatment of osteoarthritis of the knee, hip and shoulder in former NFL players. J Stem Cell Res Ther. 2018; 4(1):9-13.

Philippon M J, Nepple J J, Campbell K J, Dornan G J, Jansson K S, LaPrade R F, et al. The hip fluid seal-part I: the effect of an acetabularlabral tear, repair, resection, and reconstruction on hip fluid pressurization. Knee Surg Sports Traumatol Arthrosc. 2014; 22(4):722-9.

Savoie F H, Nunley P D, Field L D. Arthroscopic management of the arthritic elbow: indications, technique, and results. Journal of Shoulder and Elbow Surgery. 1999; 8(3):214-219.

Seldes R M, Tan V, Hunt J, Katz M, Winiarsky R, Fitzgerald R H Jr. Anatomy, histologic features, and vascularity of the adult acetabular labrum. Clin Orthop Relat Res. 2001; 382:232-40.

Smith R K W, Korda M, Blunn G W, Goodship A E (2003) Isolation and implantation of autologous equine mesenchymal stem cells from bone marrow into the superficial digital flexor tendon as a potential novel treatment. Equine Veterinary Journal, 35:99-102.

Smith R K W. Mesenchymal Stem Cell Therapy in Equine Tendinopathy. Disabil Rehabil (2008) 30:20-22, 1752-1758.

Vangsness C T, Farr J, Boyd J, Dellaero. Adult human mesenchymal stem cells delivered via intra-articular injection to the knee following partial medial meniscectomy: a randomized, double-blind controlled study. JBJS. 2014:90-98.

Zhang S, Chuah S J, Lai R C, Hui J H P, Lim S K, Toh W S. MSC Exosomes Mediate Cartilage Repair by Enhancing Proliferation, Attenuating Apoptosis and Modulating Immune Reactivity. Biomaterials. 2018 February; 156: 16-27.

Zhao L, Kaye A D. Stem Cells for the Treatment of Knee Osteoarthritis: A Comprehensive Review. Pain Physician. 2018; 21:229-241.

What is claimed is:

1. A method of treating osteoarthritis in a subject in need thereof, the method comprising: administering to the subject a therapeutically effective amount of a mesenchymal stem cell (MSC) exosome composition comprising (i) MSC exosomes; (ii) an insulin-like growth factor (IGF) and (iii) vascular endothelial growth factor (VEGF).

2. The method of claim 1, wherein the osteoarthritis affects one or more joints, wherein the one or more joints comprise one or more of the ankle, knee, hip, wrist, elbow, shoulder, knuckle, and neck.

3. The method of claim 2, wherein the MSC exosome composition is administered to each joint affected by the osteoarthritis.

4. The method of claim 1, wherein the MSC exosome composition is administered via injection, the MSC exosome composition is administered with a scaffold, or the MSC exosome composition is administered in a hydrogel, topical cream, or salve.

5. The method of claim 1, further comprising preparing the MSC exosome composition prior to the administering, the preparing comprising: (a) culturing a bone marrow-derived mesenchymal stem cell (bmMSC) at about 0.1% to about 2% oxygen to generate a conditioned medium comprising the MSC exosome composition; and (b) isolating the MSC exosome composition.

6. The method of claim 5, wherein culturing the bmMSC occurs at a pH of about 6.2 to about 7.4.

7. The method of claim 5, wherein the bmMSC is a human bmMSC.

8. The method of claim 1, wherein the MSC exosome composition comprises saline.

9. The method of claim 1, wherein the MSC exosome composition comprises MSC exosomes having a size of about 35 to about 150 nm.

10. The method of claim 1, wherein the exosome composition comprises exosomes having a size of about 35 to about 150 nm.

11. The method of claim 1, wherein the exosome composition further comprises a therapeutically effective amount of hepatocyte growth factor (HGF), interleukin-4 (IL-4), interleukin-6 (IL-6), interleukin-10 (IL-10), bone morphogenetic protein 5 (BMP5), orepidermal growth factor (EGF), or a combination of two or more thereof.

12. The method of claim 1, wherein the exosome composition further comprises a a therapeutically effective amount of interleukin-4 (IL-4), interleukin-6 (IL-6), interleukin-10 (IL-10), IL-1 receptor antagonist, bone morphogenetic protein (BMP), granulocyte colony stimulating factor (G-CSF), or granulocyte macrophage colony stimulating factor (GM-CSF), or a combination of two or more thereof.

13. The method of claim 1, wherein the MSC exosome composition further comprises a cryoprotectant oligosaccharide and/or a biocompatible polymer.

14. The method of claim 1, wherein the MSC exosome composition further comprises a a therapeutically effective amount of bone morphogenetic protein (BMP).

15. The method of claim 1, wherein the MSC exosome composition further comprises a a therapeutically effective amount of macrophage colony stimulating factor (M-CSF).

16. The method of claim 1, wherein the MSC exosome composition further comprises a a therapeutically effective amount of transforming growth factor p1 (TGF-31).

17. The method of claim 1, wherein the MSC exosome composition further comprises a a therapeutically effective amount of granulocyte macrophage colony stimulating factor (GM-CSF).

18. The method of claim 1, wherein the MSC exosome composition further comprises a a therapeutically effective amount of interleukin-4 (IL-4), interleukin-10 (IL-10), or bone morphogenetic protein 5 (BMP5), or a combination of two or more thereof.

19. The method of claim 1, wherein the MSC exosome composition further comprises a a therapeutically effective amount of IL-1 receptor antagonist, fibroblast growth factor-1 (FGF 1), fibroblast growth factor-2 (FGF2), platelet derived growth factor (PDGF), macrophage colony stimulating factor (M-CSF), or granulocyte colony stimulating factor (G-CSF), or a combination of two or more thereof.

20. The method of claim 1, wherein the MSC exosome composition further comprises a a therapeutically effective amount of prostaglandin E2 (PGE2), transforming growth factor p1 (TGF-31), hepatocyte growth factor (HGF), stromal cell derived factor-1 (SDF-1), indoleamine 2,3-dioxygenase, interleukin-4 (IL-4), interleukin-6 (IL-6), interleukin-10 (IL-10), IL-1 receptor antagonist, soluble TNF-α receptor, fibroblast growth factor-1 (FGF1), fibroblast growth factor-2 (FGF2), bone morphogenetic protein (BMP), bone morphogenetic protein 5 (BMP5), epidermal growth factor (EGF), transforming growth factor-a (TGF-a), platelet derived growth factor (PDGF), macrophage colony stimulating factor (M-CSF), insulin, granulocyte colony stimulating factor (G-CSF), or granulocyte macrophage colony stimulating factor (GM-CSF), or a combination of two or more thereof.

\* \* \* \* \*